(12) United States Patent
Nitta

(10) Patent No.: US 10,982,255 B2
(45) Date of Patent: Apr. 20, 2021

(54) MICROCHIP FOR NUCLEIC ACID ANALYSIS

(71) Applicant: Sony Corporation, Tokyo (JP)

(72) Inventor: Nao Nitta, Tokyo (JP)

(73) Assignee: SONY CORPORATION, Tokyo (JP)

( * ) Notice: Subject to any disclaimer, the term of this patent is extended or adjusted under 35 U.S.C. 154(b) by 948 days.

(21) Appl. No.: 14/399,006

(22) PCT Filed: May 1, 2013

(86) PCT No.: PCT/JP2013/002906
§ 371 (c)(1),
(2) Date: Nov. 5, 2014

(87) PCT Pub. No.: WO2013/168395
PCT Pub. Date: Nov. 14, 2013

(65) Prior Publication Data
US 2015/0086992 A1    Mar. 26, 2015

(30) Foreign Application Priority Data

May 10, 2012 (JP) .............................. JP2012-108719

(51) Int. Cl.
*C12Q 1/68* (2018.01)
*G01N 33/84* (2006.01)
*C12Q 1/6816* (2018.01)
*B32B 37/18* (2006.01)

(52) U.S. Cl.
CPC ................ *C12Q 1/68* (2013.01); *B32B 37/18* (2013.01); *C12Q 1/6816* (2013.01); *G01N 33/84* (2013.01); *Y10T 156/10* (2015.01); *Y10T 436/143333* (2015.01)

(58) Field of Classification Search
CPC ................ C12Q 1/68; C12Q 2563/107; C12Q 2565/629; B32B 37/18
See application file for complete search history.

(56) References Cited

U.S. PATENT DOCUMENTS

| | | | | |
|---|---|---|---|---|
| 7,405,054 B1 * | 7/2008 | Hasenbank | ...... | G01N 33/54373 435/7.9 |
| 9,182,349 B2 * | 11/2015 | Nitta | .................. | G01N 21/6428 |
| 2001/0006786 A1 * | 7/2001 | Sato | ..................... | B01J 19/0046 435/6.11 |
| 2002/0160400 A1 * | 10/2002 | Lakowicz | ............ | C12Q 1/6818 435/6.11 |
| 2002/0168671 A1 * | 11/2002 | Burns | ............... | B01L 3/502738 435/6.11 |
| 2008/0125330 A1 * | 5/2008 | Cady | ................. | B01L 3/502707 506/17 |
| 2008/0164155 A1 * | 7/2008 | Pease | ................ | B01L 3/502715 205/777.5 |
| 2009/0137418 A1 * | 5/2009 | Miller | ..................... | B82Y 30/00 506/9 |
| 2011/0312036 A1 | 12/2011 | Kojima et al. | | |
| 2012/0225491 A1 * | 9/2012 | Ram | .................... | G01N 33/588 436/501 |
| 2012/0309084 A1 | 12/2012 | Watanabe et al. | | |
| 2013/0288351 A1 * | 10/2013 | Nitta | .................. | G01N 21/6428 435/287.2 |
| 2014/0038176 A1 | 2/2014 | Nitta | | |

FOREIGN PATENT DOCUMENTS

| | | | | |
|---|---|---|---|---|
| EP | 2639304 | | 9/2013 | |
| JP | 2009-150809 | | 7/2009 | |
| JP | 2009-150809 A | | 7/2009 | |
| JP | 2009-183179 | | 8/2009 | |
| JP | 2009-183179 A | | 8/2009 | |
| JP | 2011-160728 | | 8/2011 | |
| JP | 2012-024072 | | 2/2012 | |
| JP | WO2012-063441 | * | 5/2012 | ............. C12N 15/09 |
| JP | 2012-118051 | | 6/2012 | |
| JP | 2012-118051 A | | 6/2012 | |
| WO | 2010/065781 | | 6/2010 | |
| WO | WO2010-065781 | * | 6/2010 | ............. G01N 33/53 |
| WO | 2012/063441 A1 | | 5/2012 | |
| WO | WO-2012095935 A1 | * | 7/2012 | ......... G01N 21/6486 |

OTHER PUBLICATIONS

Rotaru A, Dutta S, Jentzsch E, Gothelf K, Mokhir A. Selective dsDNA-templated formation of copper nanoparticles in solution. Angew Chem Int Ed Engl. Aug. 2, 2010; 49(33):5665-7.*
English Translation of WO2012-063441, filed Nov. 4, 2011.*
Jia X, Li J, Han L, Ren J, Yang X, Wang E. DNA-hosted copper nanoclusters for fluorescent identification of single nucleotide polymorphisms. ACS Nano. Apr. 24, 2012; 6(4):3311-7. Epub Mar. 20, 2012.*
Lin YW, Huang MJ, Chang HT. Analysis of double-stranded DNA by microchip capillary electrophoresis using polymer solutions containing gold nanoparticles. J Chromatogr A. Oct. 3, 2003; 1014(1-2):47-55.*
Rucker VC, Foister S, Melander C, Dervan PB. Sequence specific fluorescence detection of double strand DNA. J Am Chem Soc. Feb. 5, 2003; 125(5):1195-202.*
Shiddiky, Muhammad JA, and Yoon-Bo Shim. Microchip and capillary electrophoresis using nanoparticles. Kumar CSSR. Microfluidic devices in nanotechnology: Applications. John Wiley and Sons, Hoboken, NJ, US, Wiley (2010): 213-253.*
Park T, Lee S, Seong GH, Choo J, Lee EK, Kim YS, Ji WH, Hwang SY, Gweon DG, Lee S. Highly sensitive signal detection of duplex dye-labelled DNA oligonucleotides in a PDMS microfluidic chip: confocal surface-enhanced Raman spectroscopic study. Lab Chip. Apr. 2005; 5(4):437-42. Epub Jan. 26, 2005.*
Wang J, Tian B, Sahlin E. Micromachined electrophoresis chips with thick-film electrochemical detectors. Anal Chem. Dec. 1, 1999; 71(23):5436-40.*

(Continued)

*Primary Examiner* — Teresa E Strzelecka
*Assistant Examiner* — Olayinka A Oyeyemi
(74) *Attorney, Agent, or Firm* — K&L Gates LLP

(57) ABSTRACT

There is provided a microchip including a reaction region and a detection region connected to the reaction region by a flow passage, the detection region including copper.

12 Claims, 56 Drawing Sheets

Specification includes a Sequence Listing.

(56) References Cited

OTHER PUBLICATIONS

Wang AJ, Xu JJ, Zhang Q, Chen HY. The use of poly(dimethylsiloxane) surface modification with gold nanoparticles for the microchip electrophoresis. Talanta. Mar. 15, 2006; 69(1):210-5. Epub Nov. 21, 2005.*
Zhou Z, Du Y, Dong S. Double-strand DNA-templated formation of copper nanoparticles as fluorescent probe for label-free aptamer sensor. Anal Chem. Jul. 1, 2011; 83(13):5122-7. Epub Jun. 13, 2011.*
Burns MA, Johnson BN, Brahmasandra SN, Handique K, Webster JR, Krishnan M, Sammarco TS, Man PM, Jones D, Heldsinger D, Mastrangelo CH, Burke DT. An integrated nanoliter DNA analysis device. Science. Oct. 16, 1998; 282(5388):484-7.*
Nilsson C, Birnbaum S, Nilsson S. Use of nanoparticles in capillary and microchip electrochromatography. J Chromatogr A. Oct. 19, 2007; 1168(1-2):212-24; discussion 211. Epub Jul. 20, 2007.*
Chandra, R., Taneja, P. and Ayyub, P., 1999. Optical properties of transparent nanocrystalline Cu2O thin films synthesized by high pressure gas sputtering. Nanostructured Materials, 11(4), pp. 505-512. (Year: 1999).*
Nair, M.T.S., Guerrero, L., Arenas, O.L. and Nair, P.K., 1999. Chemically deposited copper oxide thin films: structural, optical and electrical characteristics. Applied Surface Science, 150(1-4), pp. 143-151. (Year: 1999).*
Office Action issued in JP Application 2012108719, dated Jan. 19, 2016, 10 pages.
Rotaru, Alexandru. Selective dsDNA-Templated Formation of Copper Nanoparticles in Solution. Angew. Chem. Int. Ed. 2010, vol. 49, p. 5665-5667.
Japanese Office Action (with English translation) dated Jul. 26, 2016 in corresponding Japanese application No. 2012-108719 (10 pages).
V. Rostovtsev et al., "A Stepwise Huisgen Cycloaddition Process: Copper(I)-Catalyzed Regioselective Ligation" of Azides and Terminal Alkynes, Angew. Chem. Int. Ed. 2002, vol. 41, No. 14, pp. 2596-2599. (4 pages).
Okabe et al., "Direct Visualization of Copper-Metallothionein in LEC Rat Kidneys: Application of Autofluorescence Signal of Copper-Thiolate Cluster," The Journal of Histochemistry and Cytochemistry, vol. 44, No. 8, pp. 865-873, 1996. (9 pages).
Stillman, et al., "A luminescence probe for metallothionein in liver tissue: emission intensity measured directly from copper metallothionein induced in rat liver," Nov. 1989, vol. 257, No. 2, pp. 283-286. (4 pages).
Prutz et al., "Interaction of copper(I) with nucleic acids," International Journal of Radiation Biology, vol. 58, No. 2, 1990, pp. 215-234. (11 pages).
V. T. Bowen et al., "The Chemistry and Physiology of the Nucleus," Proceedings of the Symposium held Aug. 1951 by the Biology Department, Brookhaven National Laboratory. (11 pages).
Quaglia et al., "Copper-Metallothionein Autofluorescence," Image of the Month, Hepatology, vol. 50, No. 4, 2009, pp. 1312-1313. (2 pages).
M. Beltramini et al., "Luminescence Properties of Neurospora Copper Metallothionein," FEBS Letters, vol. 127, No. 2, May 1981, pp. 201-203. (3 pages).
B. K. Filshie et al., "Ultrastructure of the Copper-Accumulating Region of the *Drosophila* Larval Midgut," Tissue & Cell 1971 3 (1) pp. 77-102. (26 pages).
Hoppler et al., "Specification of a Single Cell Type by a *Drosophila* Homeotic Gene," Cell, vol. 76, pp. 689-702, Feb. 25, 1994. (14 pages).
M. Beltramini et al., "Copper Transfer Between Neurospora Copper Metallothionein and Type 3 Copper Apoproteins," FEBS Letters, vol. 142, No. 2, Jun. 1982, pp. 219-222. (4 pages).
Beltramini et al., "Spectroscopic Studies on Neurospora Copper Metallothionein," Biochemistry 1983, vol. 22, pp. 2043-2048. (6 pages).

Hoppler et al.. "Two different thresholds of wingless signalling with distinct developmental consequences in the *Drosophila* midgut," The EMBO Journal, vol. 14, No. 20, pp. 5016-5026, 1995. (11 pages).
M. Beltramini et al., "Metal Substitution of Neurospora Copper Metallothionein," Biochemistry 1984, vol. 23, pp. 3422-3427. (6 pages).
Brenner et al., "Calcium-Activated Potassium Channel Gene Expression in the Midgut of *Drosophila*," Comp. Biochem. Physiol. vol. 118B, No. 2, pp. 411-420, 1997. (10 pages).
McNulty et al., "Evidence that a copper-metallothionein complex is responsible for fluorescence in acid-secreting cells of the *Drosophila* stomach," Cell Tissue Res (2001) 304:383-389. (7 pages).
K. Munger et al., "(Cu,Zn)-Metallothioneins from Fetal Bovine Liver, The Journal of Biological Chemistry," vol. 260. No. 18, Issue of Aug. 25, 1985, pp. 10032-10038. (7 pages).
Jan A. Veenstra, "Peptidergic paracrine and endocrine cells in the midgut of the fruit fly maggot," Cell Tissue Res (2009) 336:309-323. (15 pages).
M. Beltramini et al., "Primary Structure and Spectroscopic Studies of Neurospora Copper Metallothionein," Environmental Health Perspectives, vol. 65, pp. 21-27, 1986. (7 pages).
J. Byrd et al., "Characterization of the Copper-Thiolate Cluster in Yeast Metallothionein and Two Truncated Mutants*," The Journal of Biological Chemistry, vol. 263, No. 14, Issue of May 15, 1988, pp. 6688-6694. (7 pages).
M. Beltramini et al., "Luminescence emission from Neurospora copper metallothionein," Biochem. J. (1989) 260, pp. 189-193. (5 pages).
S. Narula et al., "Establishment of the Metal-to-Cysteine Connectivities in Silver-Substituted Yeast Metallothionein," J. Am. Chem. Soc. 1991, vol. 113, pp. 9354-9358. (5 pages).
Presta et al., "Incorporation of Copper into the Yeast *Saccharomyces cerevisiae*. Identification of Cu(I)-Metallothionein in Intact Yeast Cells," Journal of Inorganic Biochemistry, 66, pp. 231-240, 1997. (10 pages).
Z. Gasyna et al., "Luminescence Decay from Copper(I) Complexes of Metallothionein," Inorganica Chimica Acta, vol. 153 (1988), pp. 115-118. (4 pages).
Fred E. Lytle, "Solution Luminescence of Metal Complexes," Applied Spectroscopy, Review Papers, vol. 24, No. 3, 1970, pp. 319-326. (8 pages).
J. H. Anglin, Jr., et al., "Fluorescence of Cu, Au and Ag Mercaptides," Photochemistry and Photobiology, 1971, vol. 13., pp. 279-281. (3 pages).
H. Kuiper et al., "Luminescence of the Copper-Carbon Monoxide Complex of Neurospora Tyrosinase," FEBS Letters, vol. 111, No. 1, Feb. 1980, pp. 232-234. (3 pages).
H. Kuiper et al., "Luminescence of carbon monoxide hemocyanins," Proc. Natl. Acad. Sci. USA, Biochemistry, vol. 77, No. 5, May 1980, pp. 2387-2389. (3 pages).
F. Sabin et al., "Photophysical Properties of Hexanuclear Copper( I) and Silver(1) Clusters," Inorg. Chem., vol. 31, 1992, pp. 1941-1945. (5 pages).
P. Ford et al., "Photochemical and Photophysical Properties of Tetranuclear and Hexanuclear Clusters of Metals with d10 and s2 Electronic Configurations," Acc. Chem. Res., vol. 26, 1993, pp. 220-226. (7 pages).
S. Narula et al., Copper- and Silver-Substituted Yeast Metallothioneins: Sequential H NMR Assignments Reflecting Conformational Heterogeneity at the C Terminus, Biochemistry 1993, vol. 32, pp. 6773-6787. (15 pages).
Poulson, D.F., "Physiological genetic studies on copper metabolism in the genus *Drosophila*," Abstracts of Papers Presented at the 1950 Meetings of the Genetics Society of America, Columbus, Ohio, Sep. 11-14, 1950, (p. 684). (3 pages).
M. Kamruzzaman et al., "Microfluidic chip based chemiluminescence detection of L-phenylalanine in pharmaceutical and soft drinks," Food Chemistry 135, 2012, pp. 57-62. (6 pages).
W. Kuhr et al., "Direct Detection of DNA with an Integrated Detector on a Microfluidic Chip," University of California Department of Chemistry. (2 pages).

(56) References Cited

OTHER PUBLICATIONS

Y. C. Chan et al., "Design and fabrication of an integrated microsystem for microcapillary electrophoresis," Journal of Micromechanics and Microengineering, vol. 13, 2003, pp. 914-921. (8 pages).

X. Zhang et al., "The interaction of taurine-salicylaldehyde Schiff base copper (II) complex with DNA and the determination of DNA using the complex as a fluorescence probe," Spectrochimica Acta Part A 77, 2010, pp. 1-5. (5 pages).

International Search Report issued in connection with International Patent Application No. PCT/JP2013/002906, dated Nov. 5, 2013. (4 pages).

Japanese Office Action dated Nov. 21, 2017 in corresponding Japanese Patent Application No. 2017-003720.

Kuhr, et al., Direction Detection of DNA With an Integrated Detector on a Microfluidic Chip, Digest of Papers, Microprocesses and Nanotechnology, '99.

Japanese Office Action dated May 15, 2018 in corresponding Japanese Application No. 2017-003720.

Kuhr, et al., Direct Detection of DNA with an integrated detector on a microfluidic chip, Digest of Papers, Microprocessess and Nanotechnology, 991999.

Rotaru, et al., Selective dsDNA-Templated Formation of Copper Nanoparticles in Solution, Angew. Chem. Int. Ed., 2010, 49, 5665-5667.

* cited by examiner

[Fig. 1A]
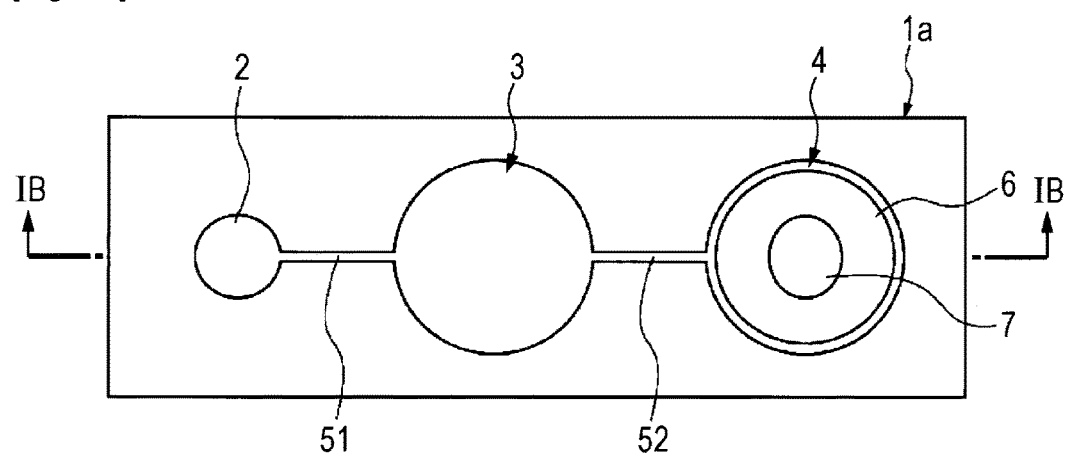
[Fig. 1B]
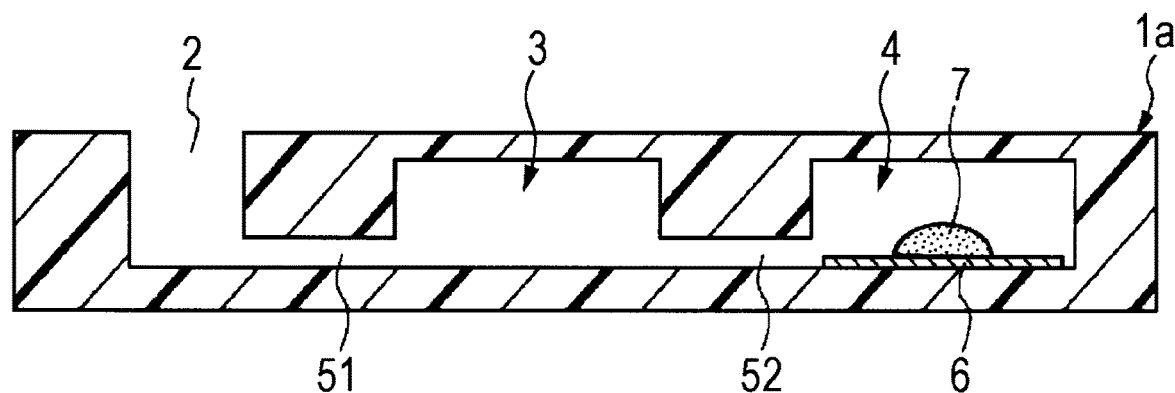

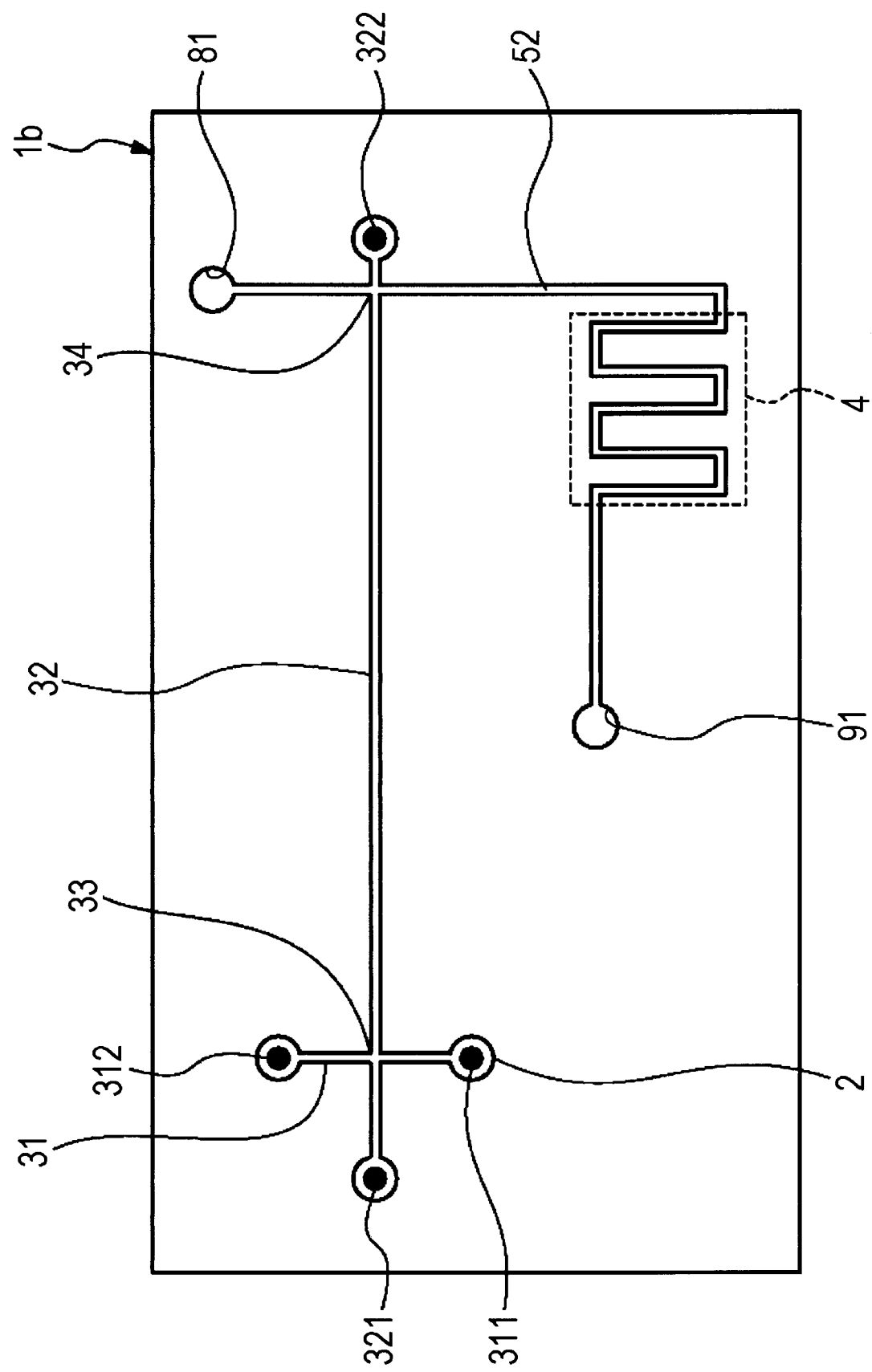
[Fig. 2]

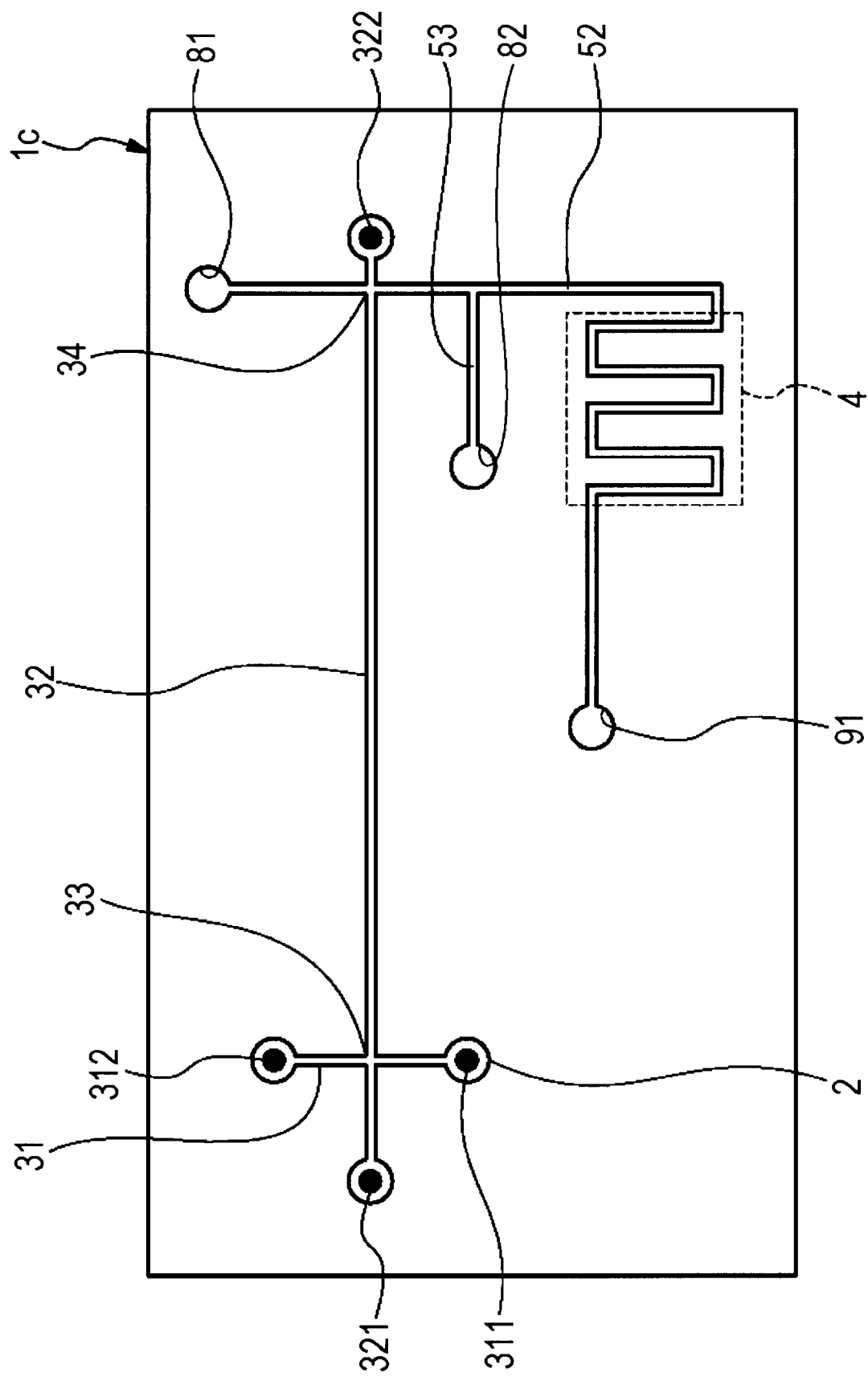
[Fig. 3]

[Fig. 4]
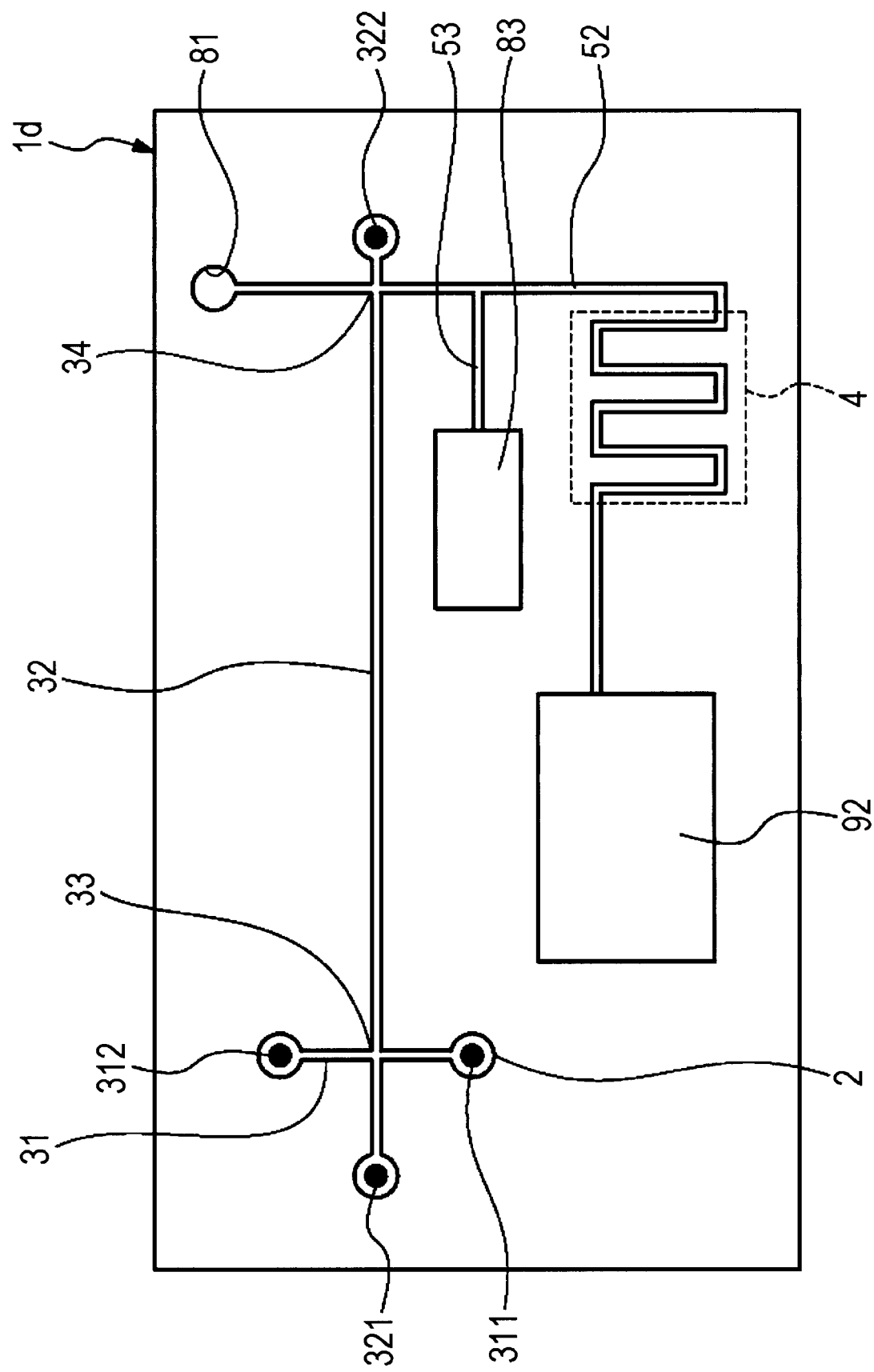

[Fig. 5A]
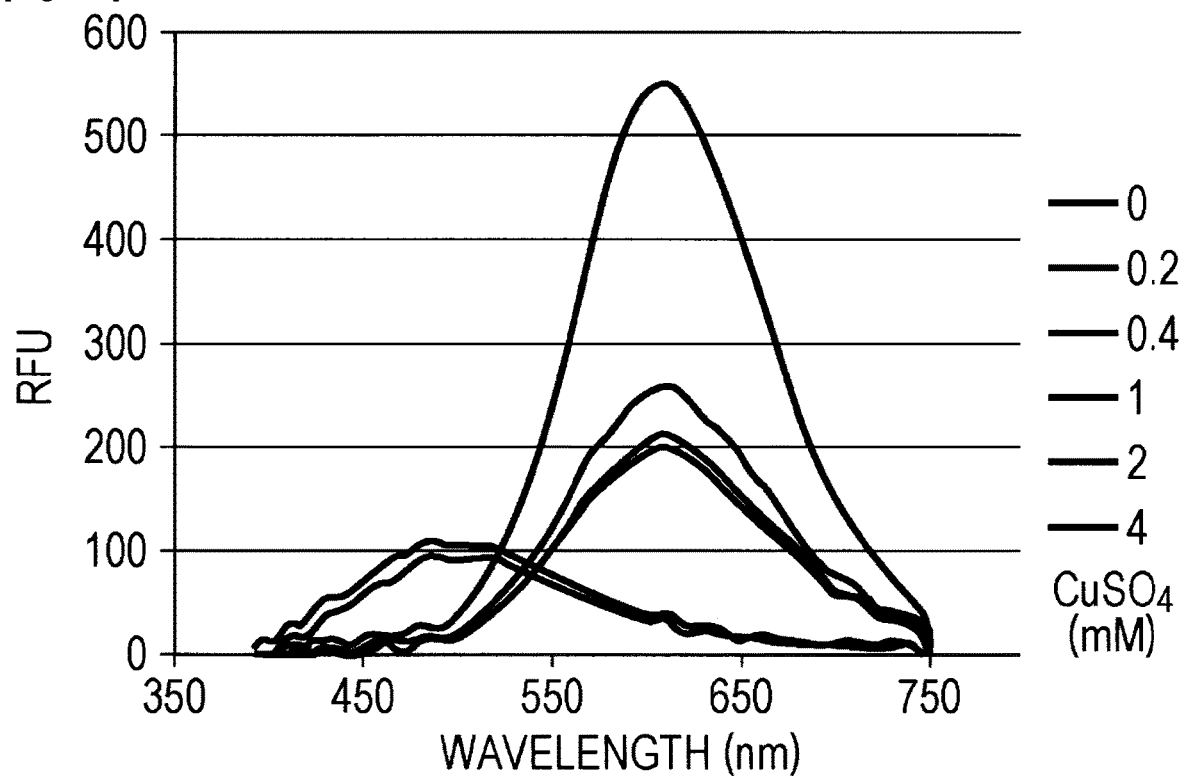
[Fig. 5B]
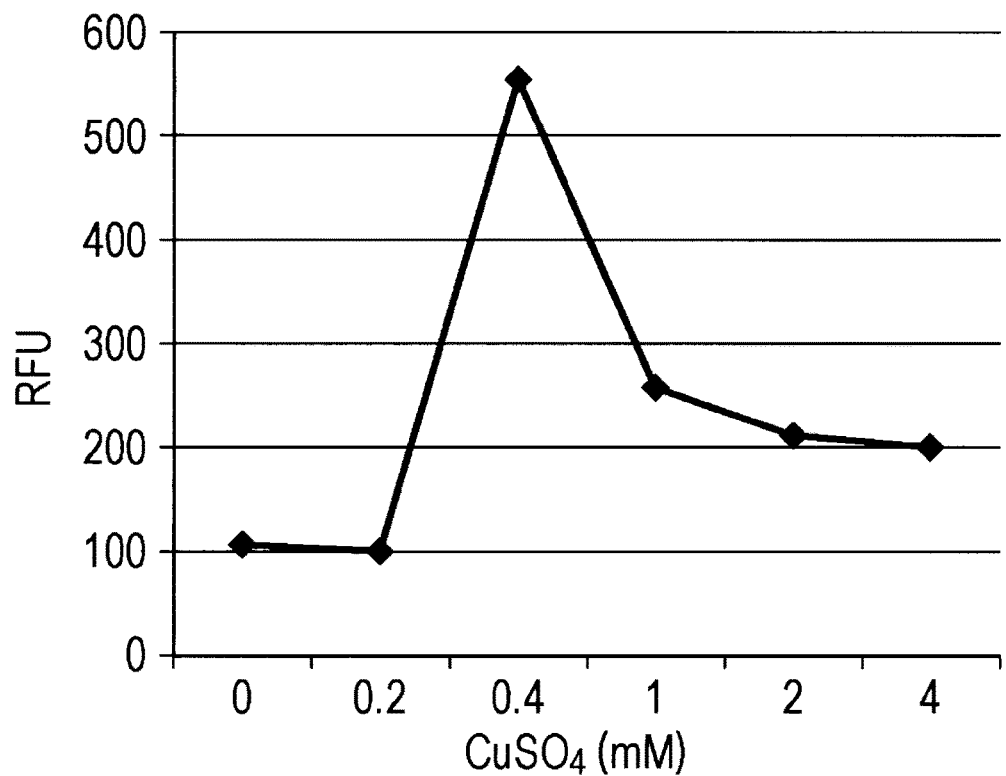

[Fig. 6A]
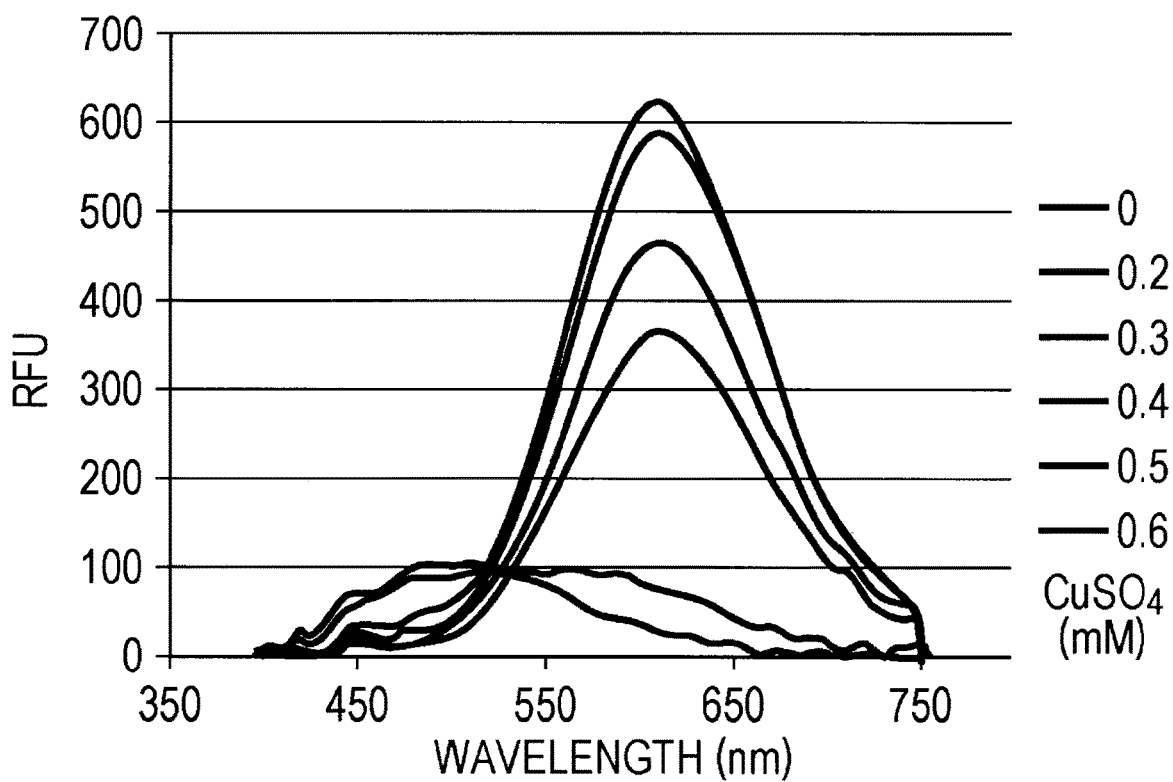
[Fig. 6B]
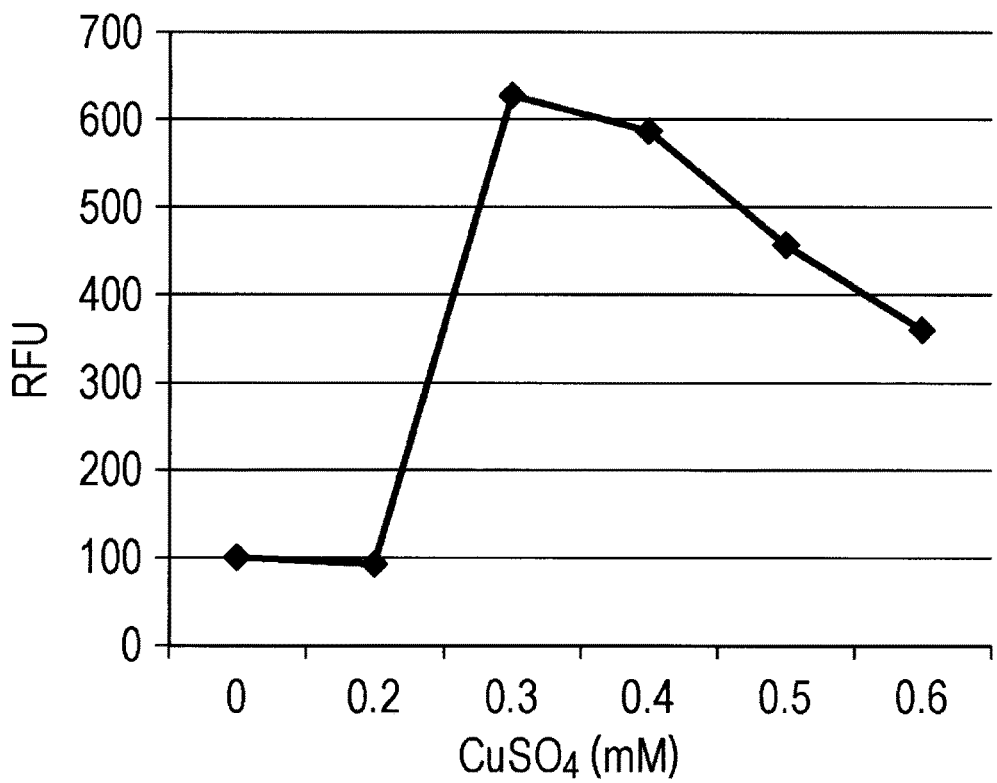

[Fig. 7A]
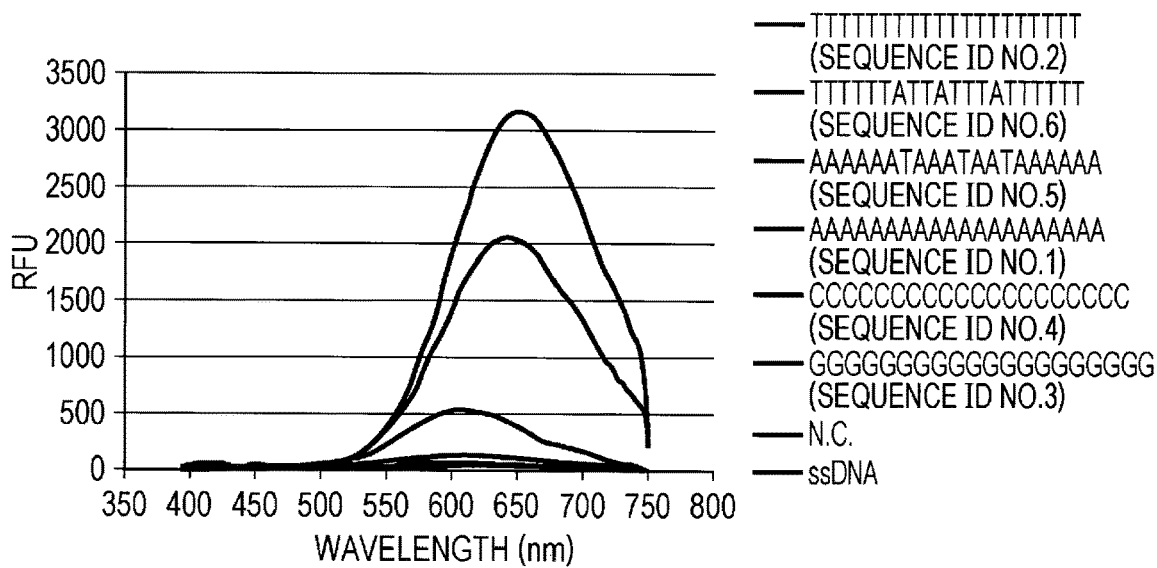
[Fig. 7B]
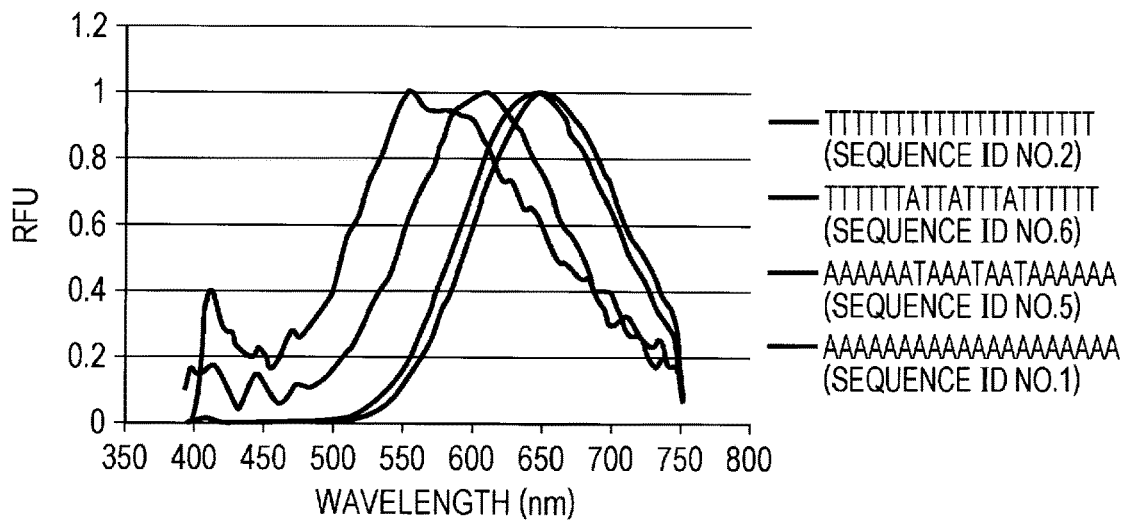
[Fig. 8A]
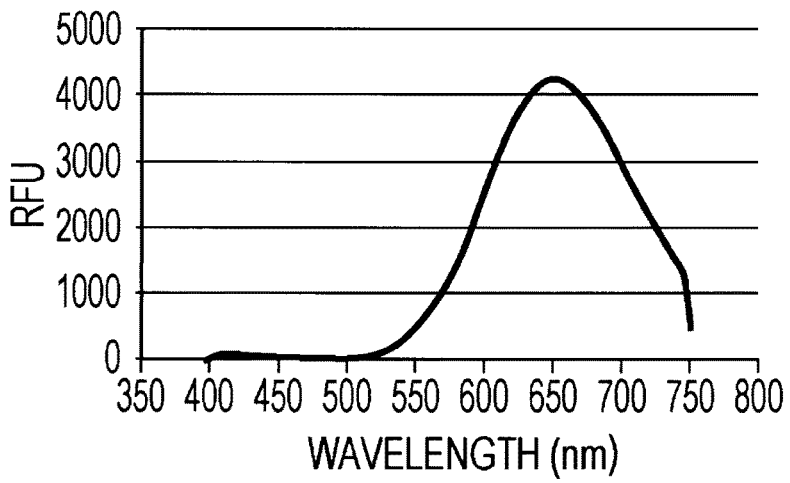

[Fig. 8B]
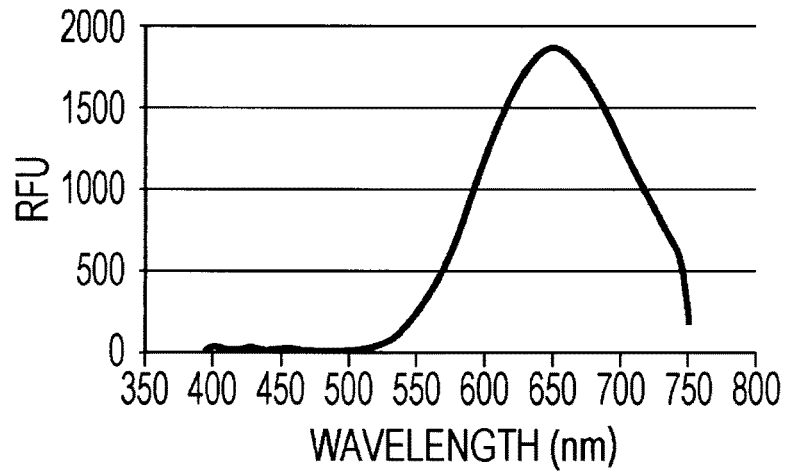
[Fig. 8C]
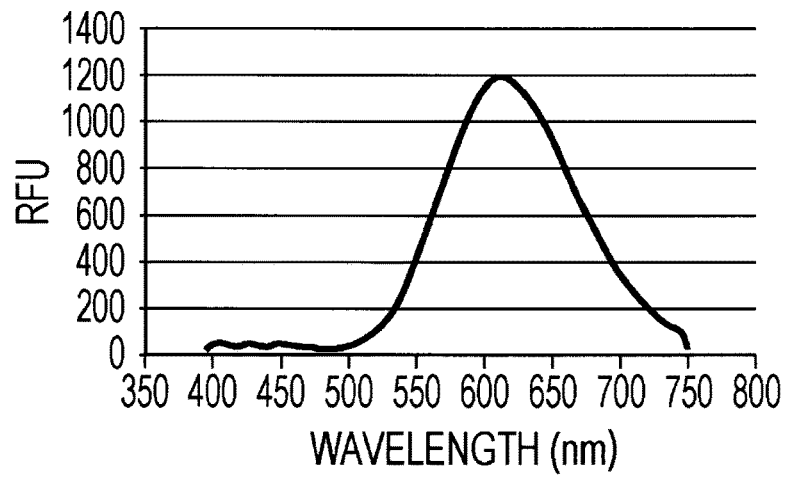
[Fig. 8D]
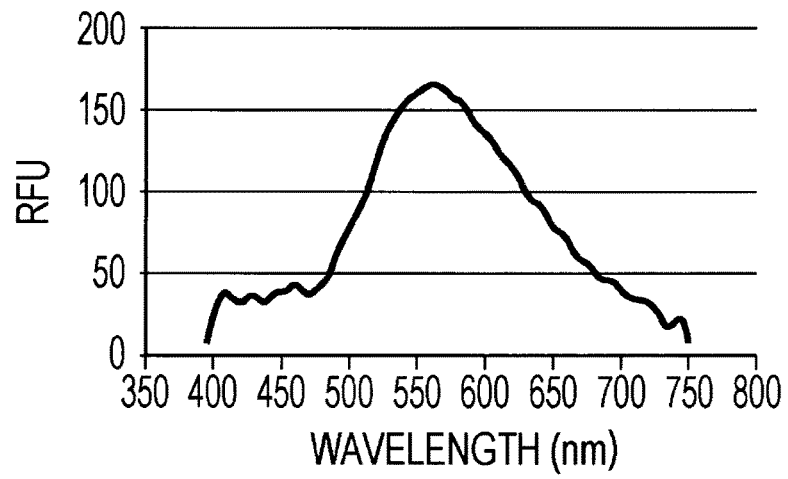

[Fig. 9]
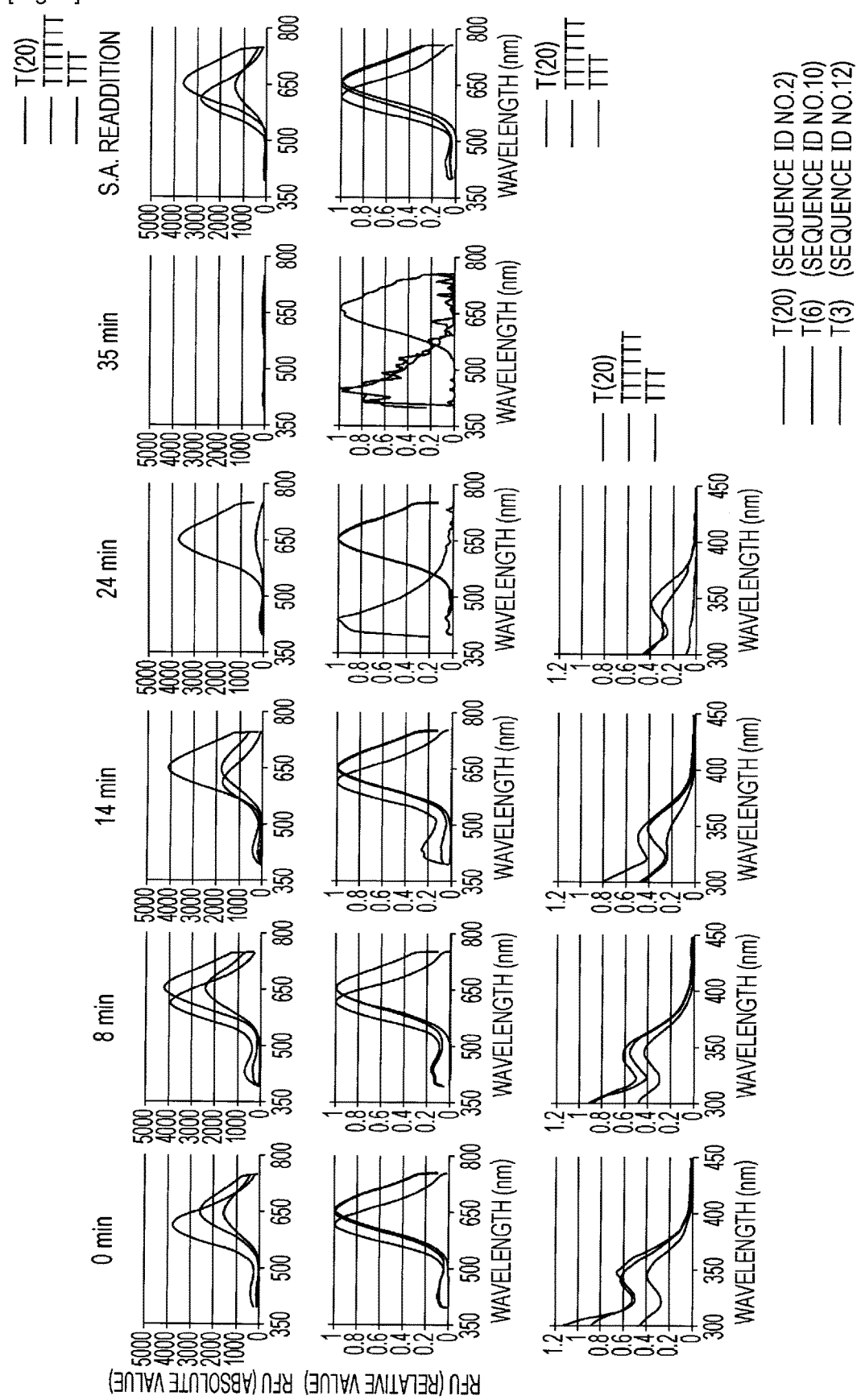

[Fig. 10A]
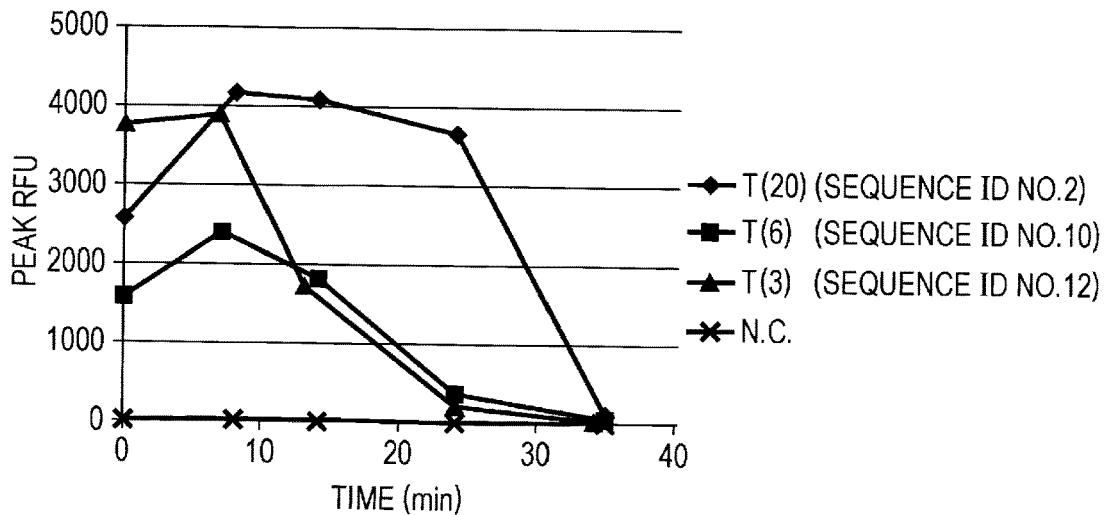
[Fig. 10B]
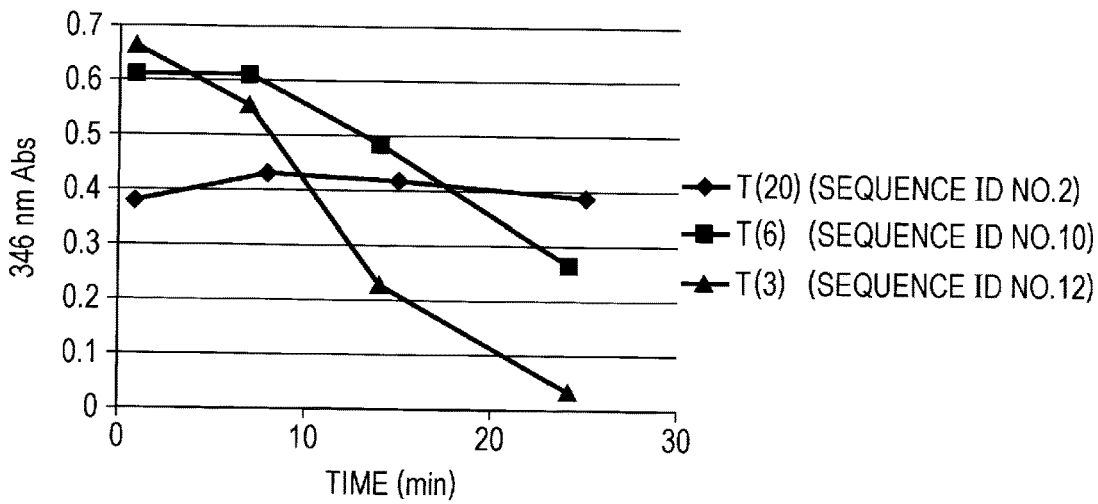
[Fig. 11A]
5'-TTTTT TTTTT TTTTT TTTTT-3' (SEQUENCE ID NO.2)
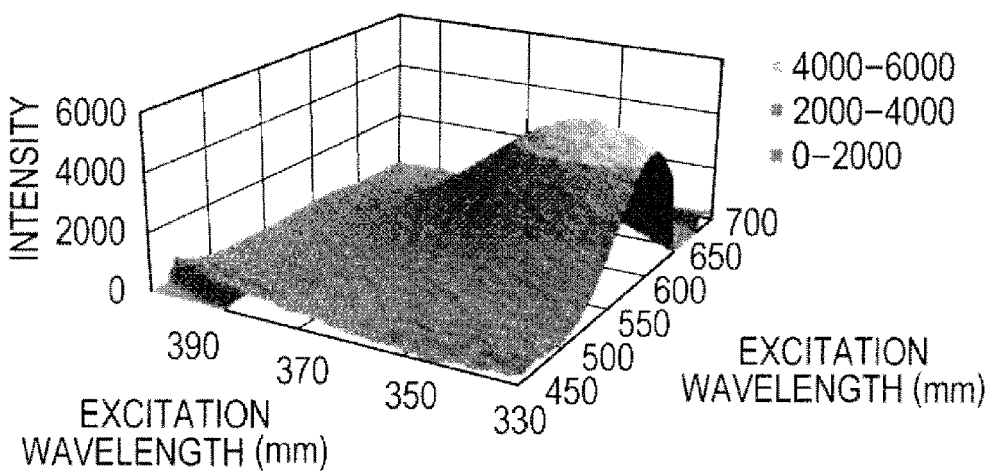

[Fig. 11B]
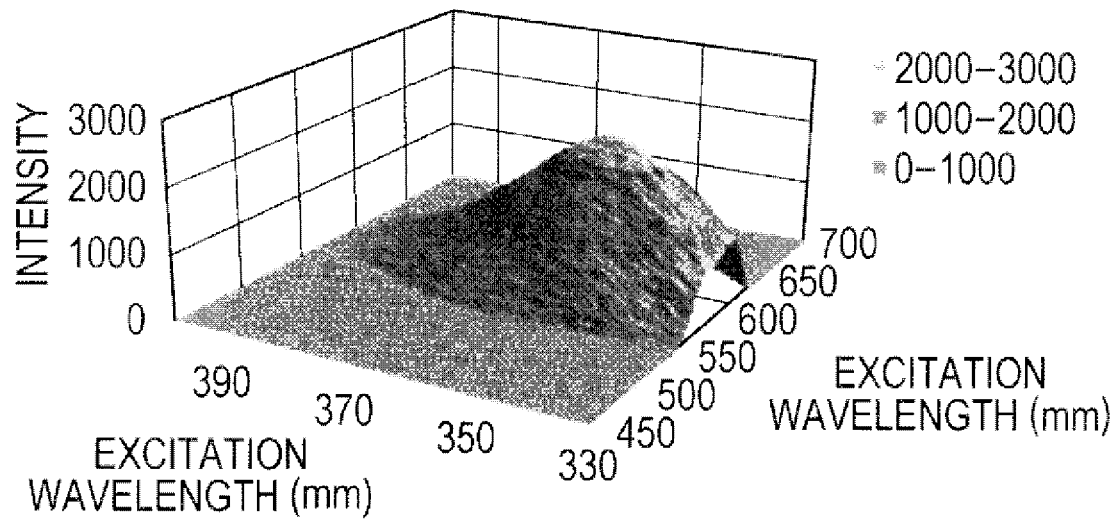
5'-TTTTT T-3' (SEQUENCE ID NO.10)
[Fig. 11C]
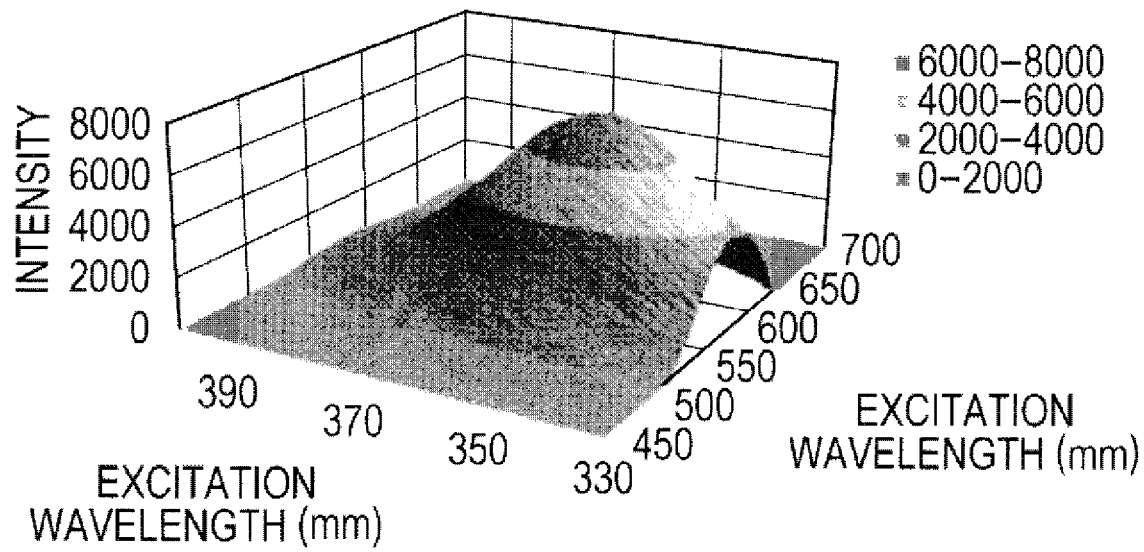
5'-TTT-3' (SEQUENCE ID NO.12)

[Fig. 12]
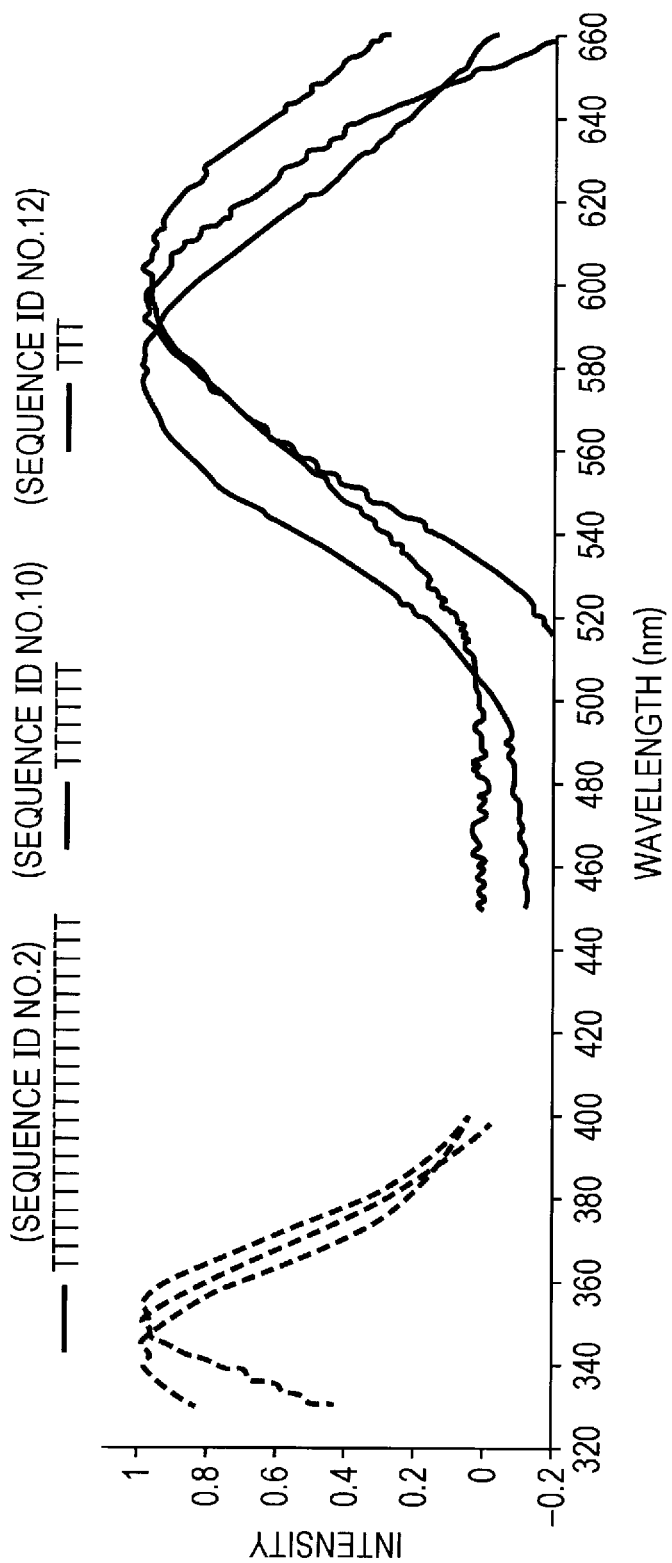

[Fig. 13A]
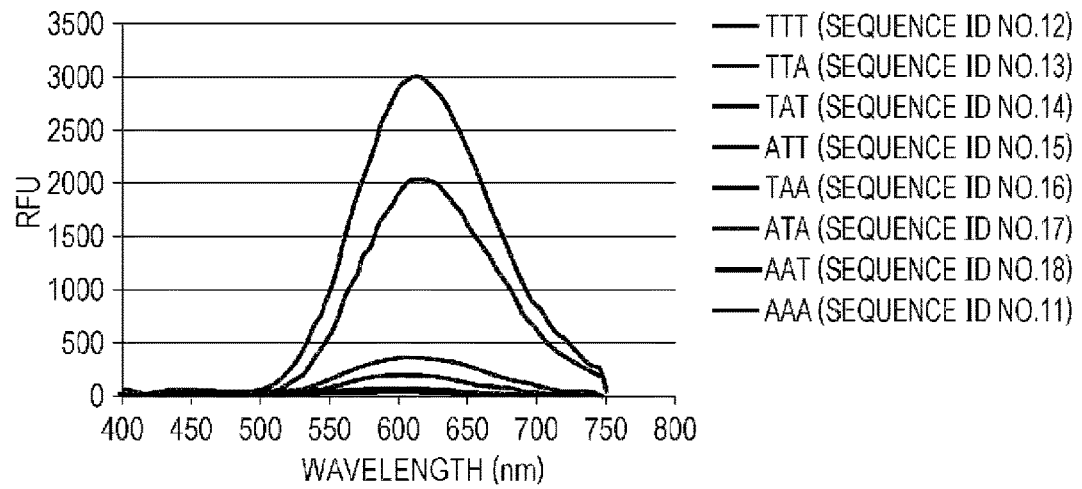
[Fig. 13B]
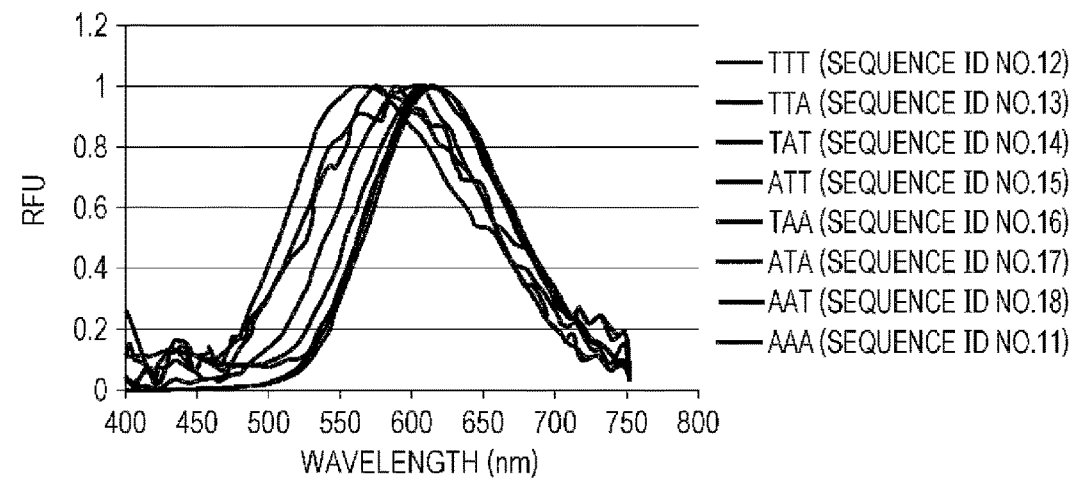
[Fig. 14A]
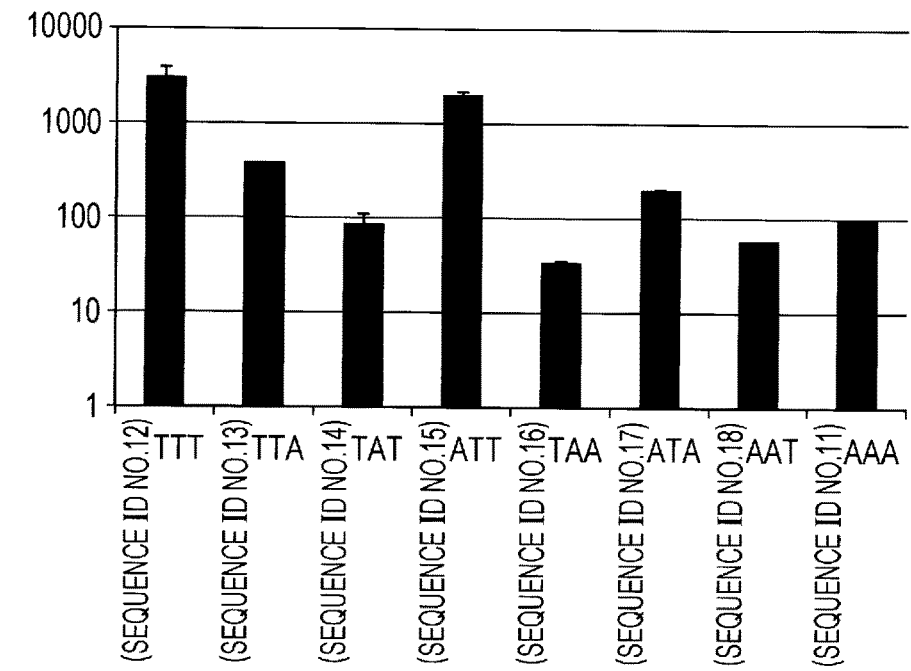

[Fig. 14B]
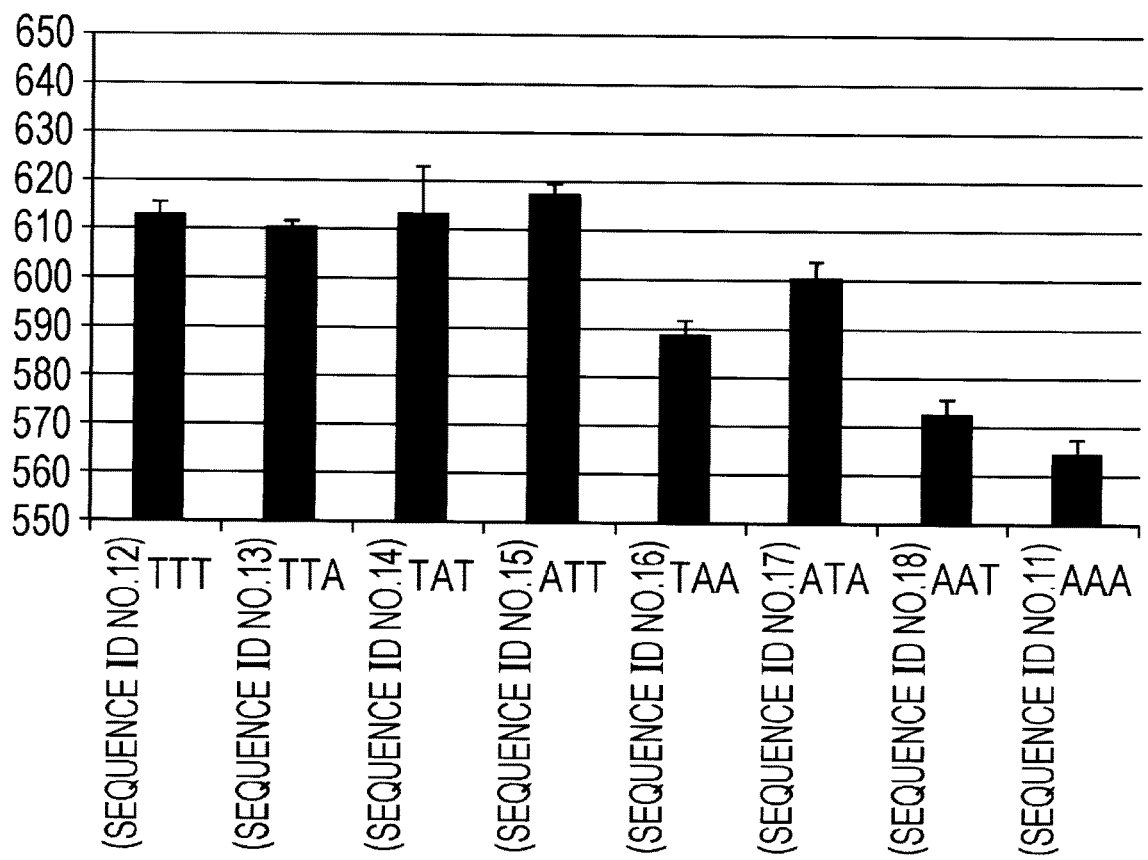
[Fig. 15A]
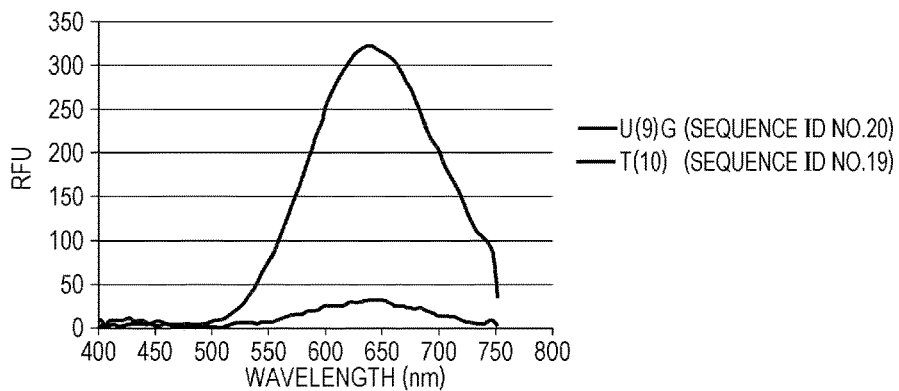
[Fig. 15B]
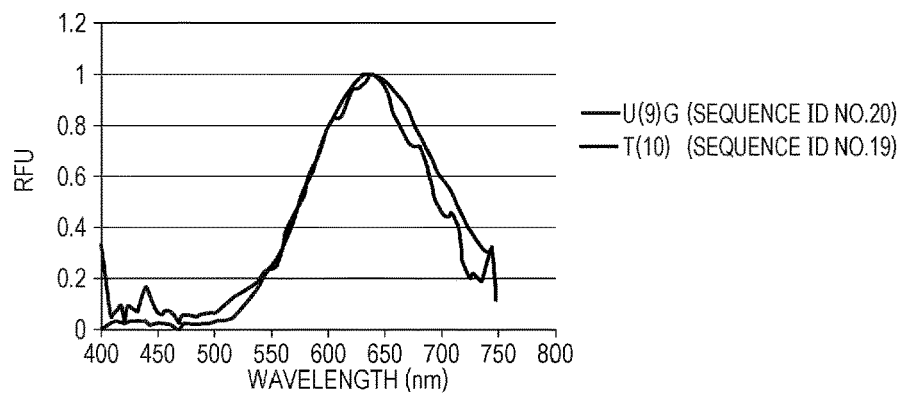

[Fig. 16]
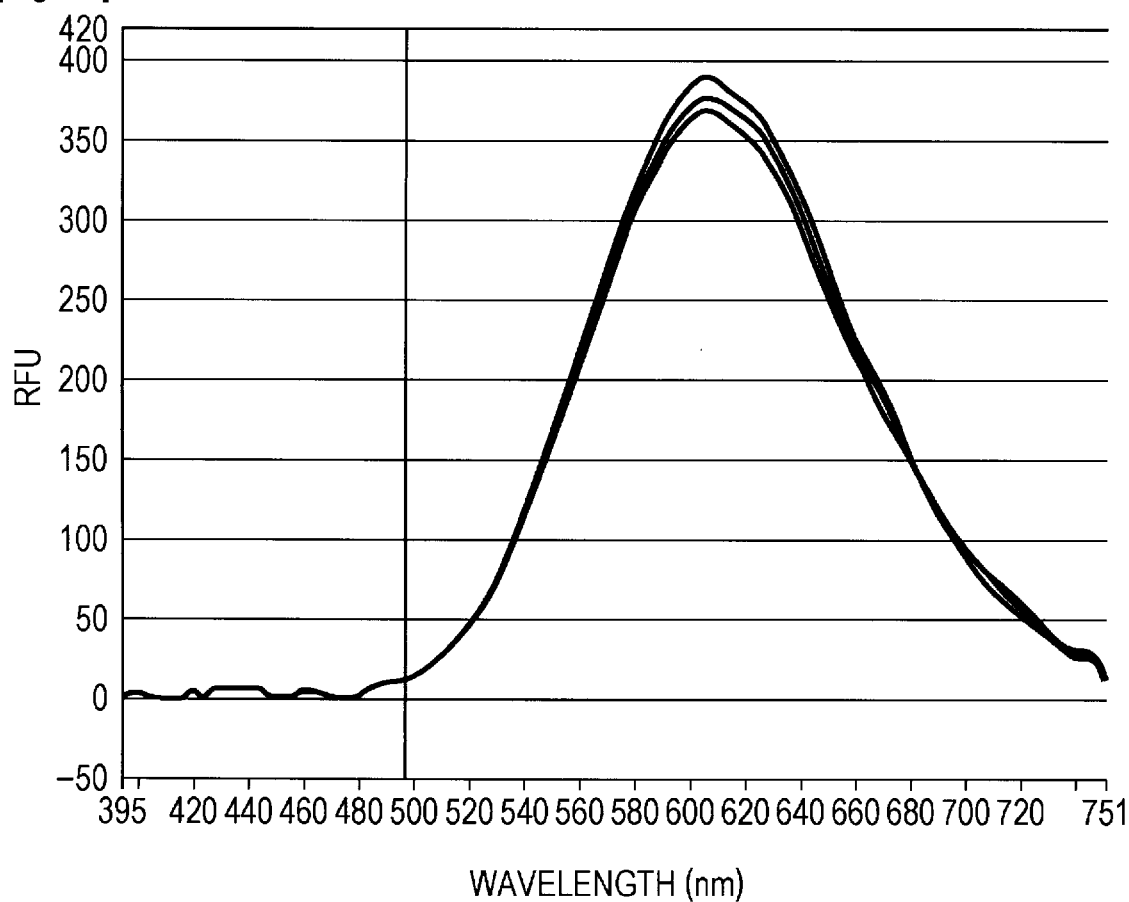
[Fig. 17]
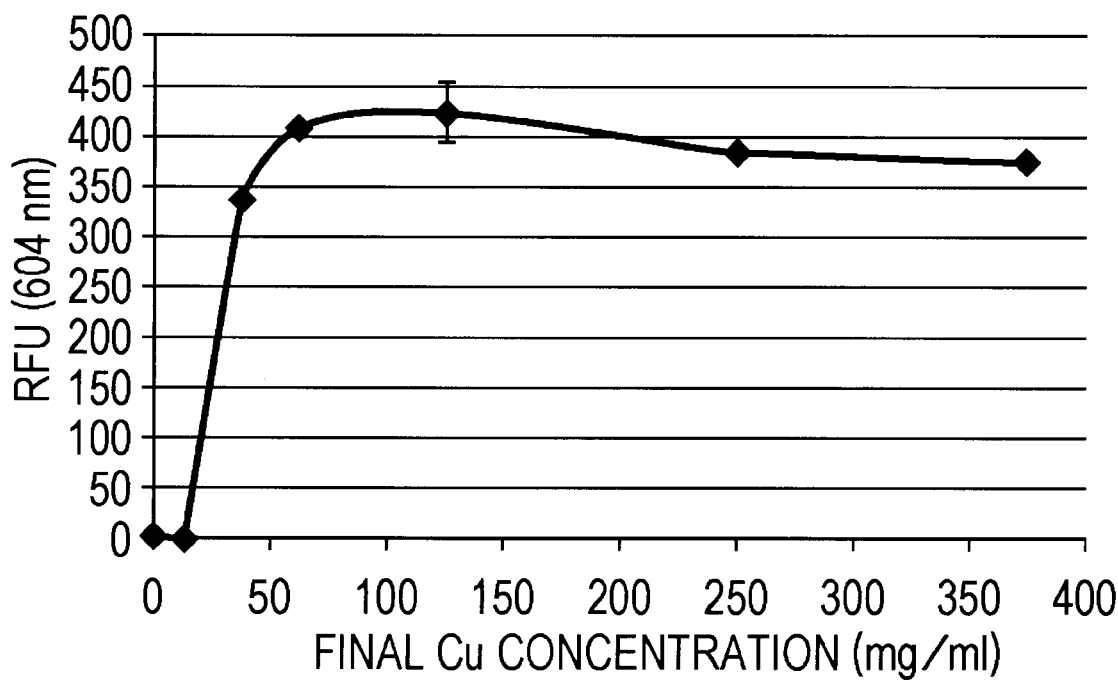

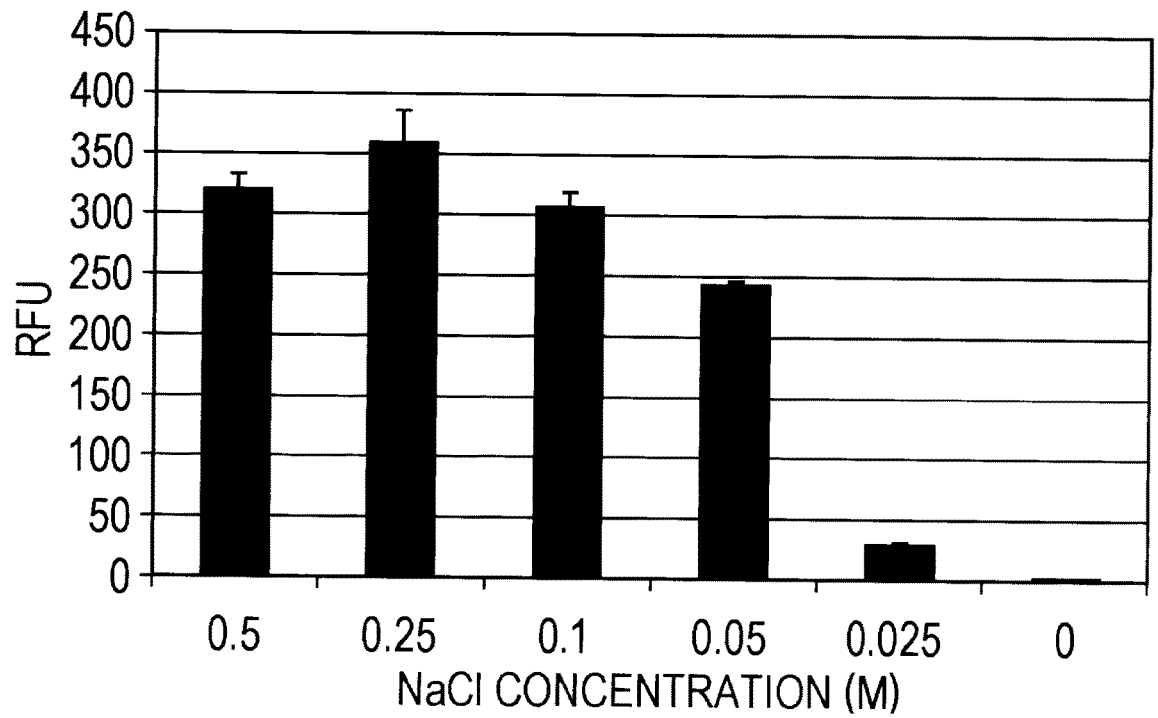
[Fig. 18A]
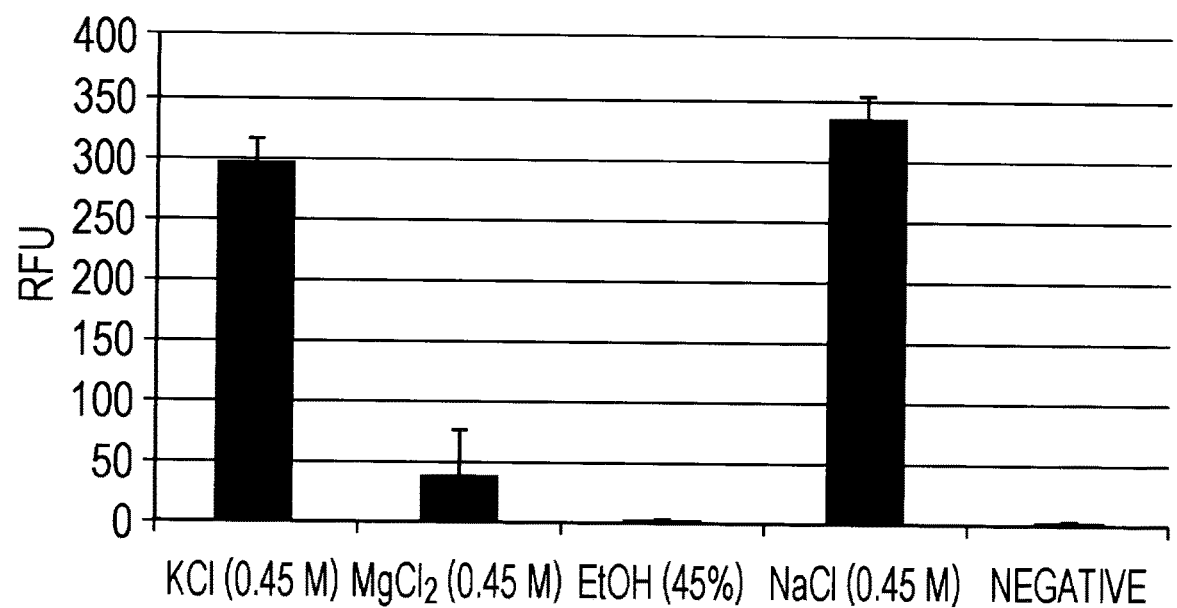
[Fig. 18B]

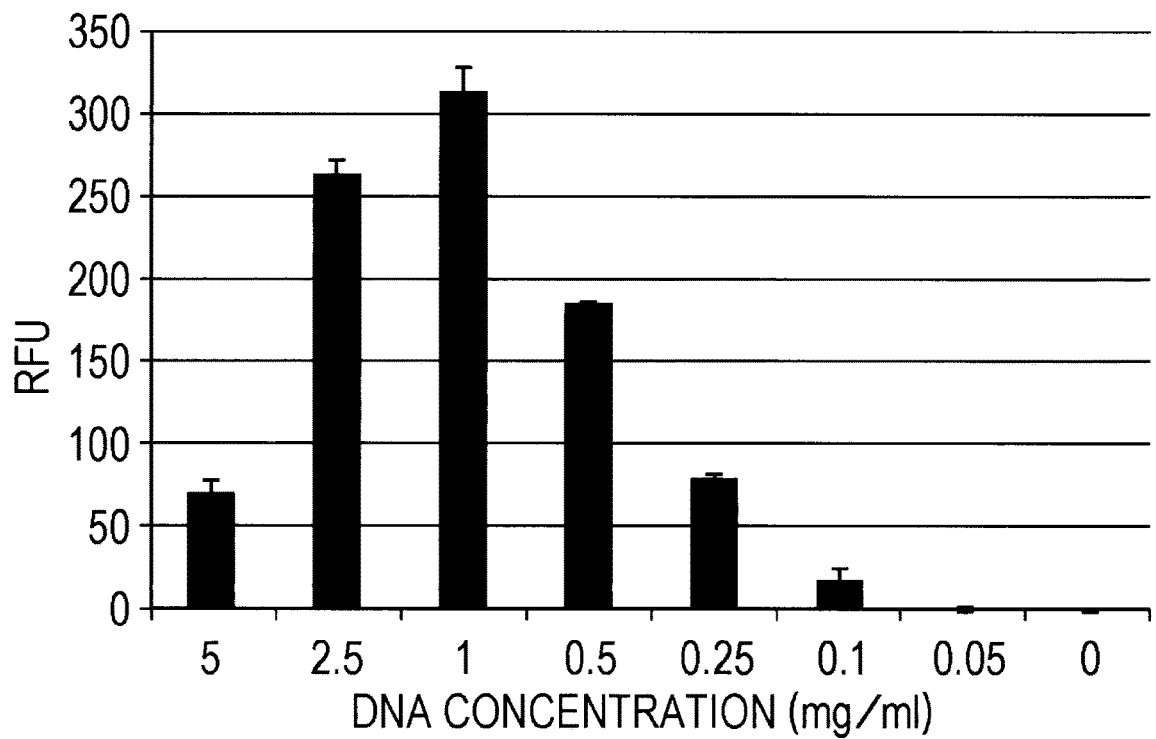
[Fig. 19A]
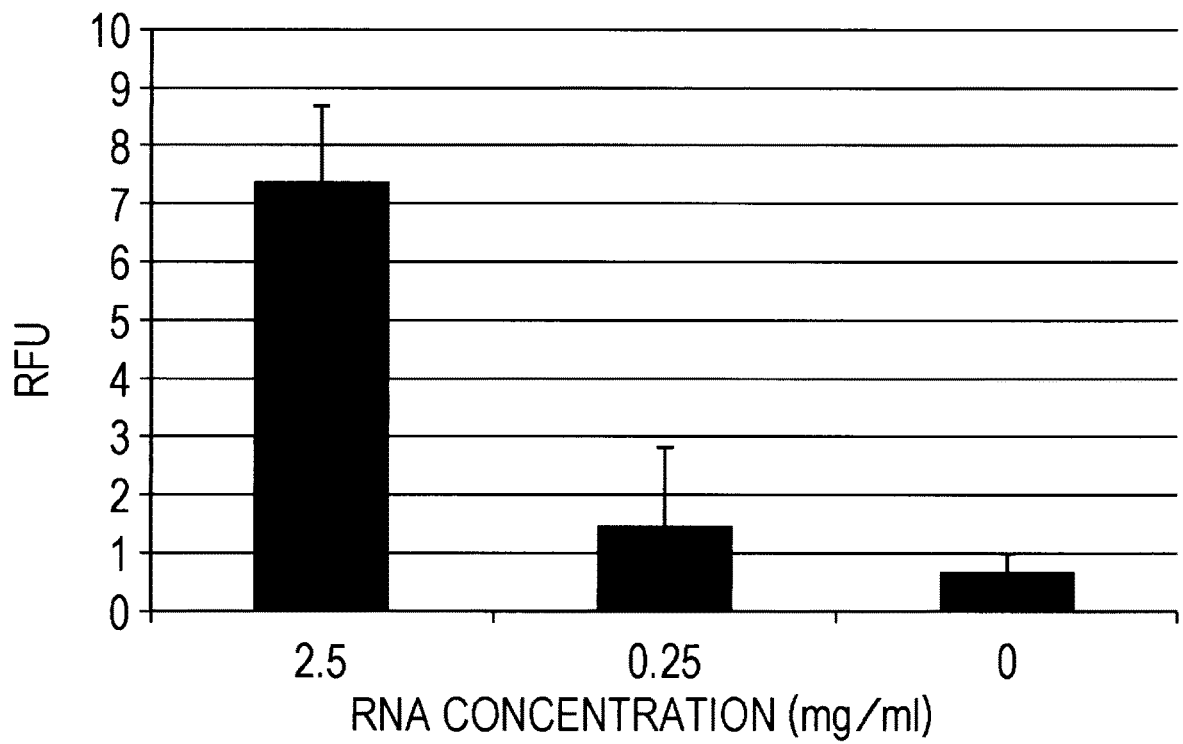
[Fig. 19B]

[Fig. 20A]
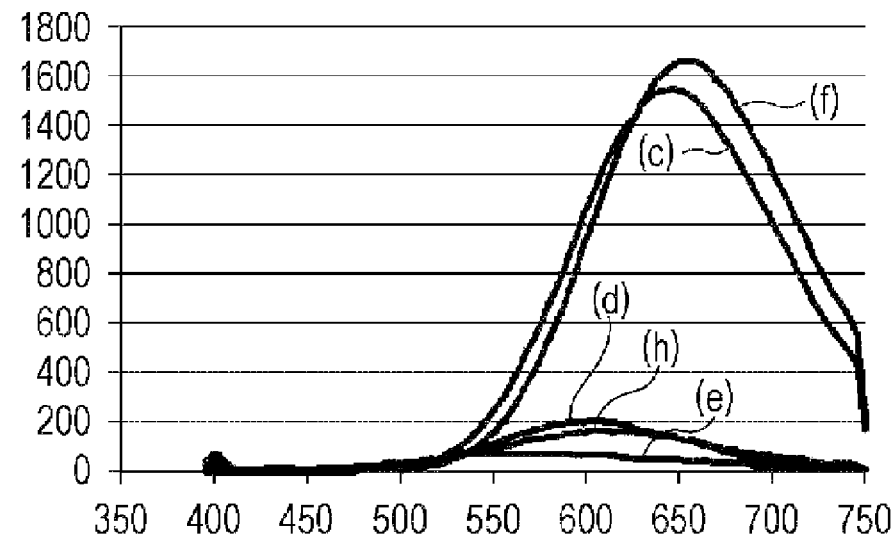
[Fig. 20B]
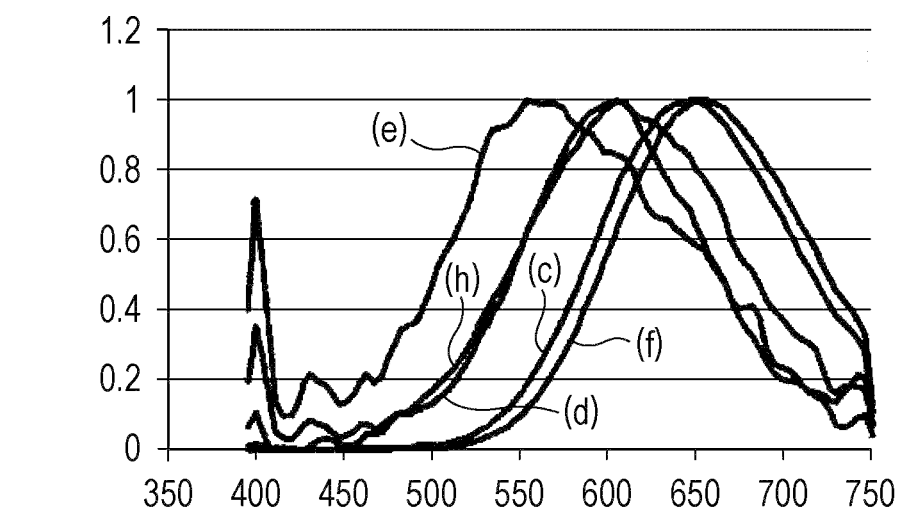
(c) SEQUENCE ID NO.6: 5'-TTTTTTATTATTTATTTTTT-3'
(d) SEQUENCE ID NO.5: 5'-AAAAAATAAATAATAAAAAA-3'
(e) SEQUENCE ID NO.1: 5'-AAAAAAAAAAAAAAAAAAAA-3'
(f) SEQUENCE ID NO.2: 5'-TTTTTTTTTTTTTTTTTTTT-3'
(h) SEQUENCE ID NO.9: 5'-AAAATTTTTTTTTTTTAAAA-3'

[Fig. 21C]
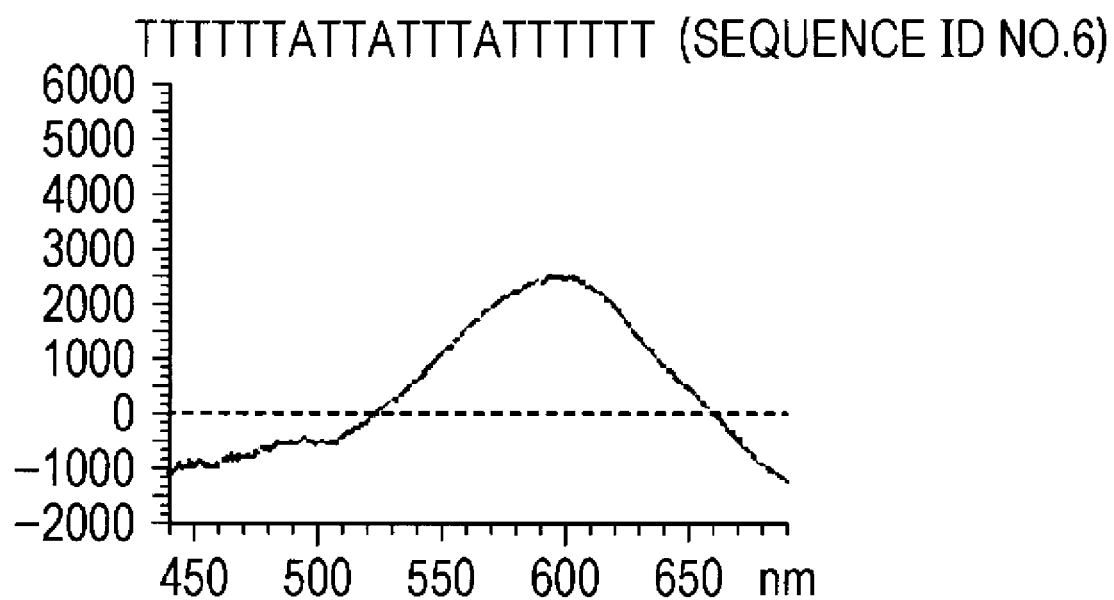
[Fig. 21D]
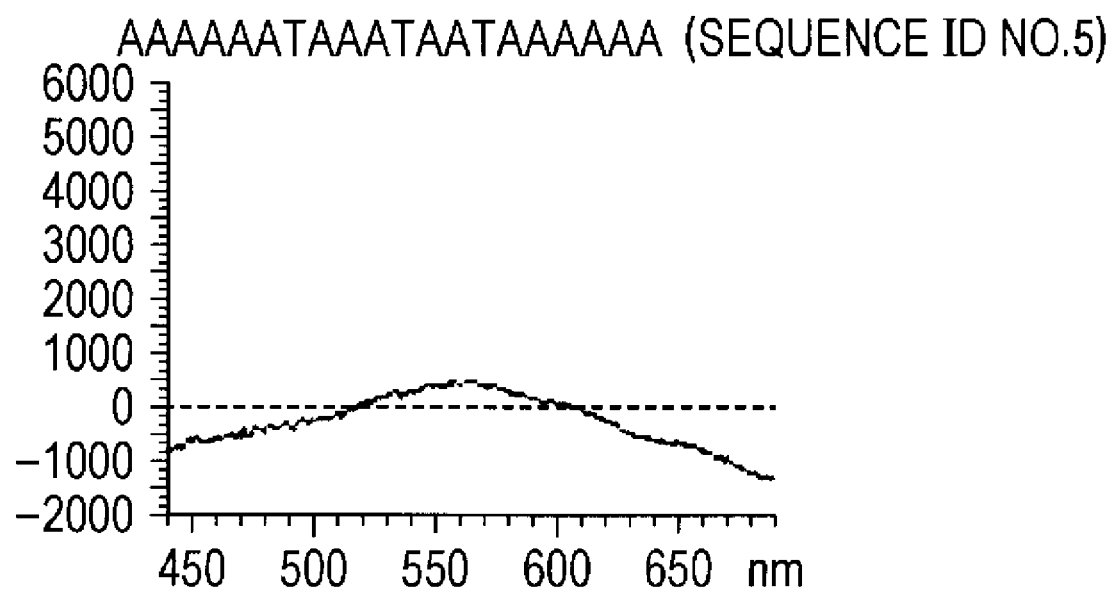

[Fig. 21E]
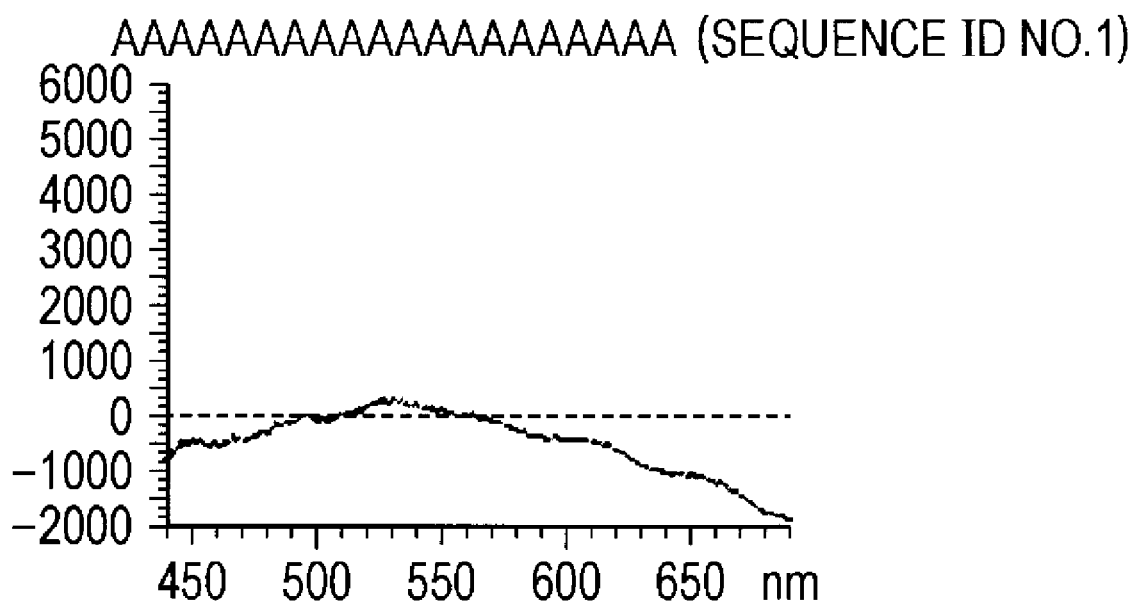
[Fig. 21F]
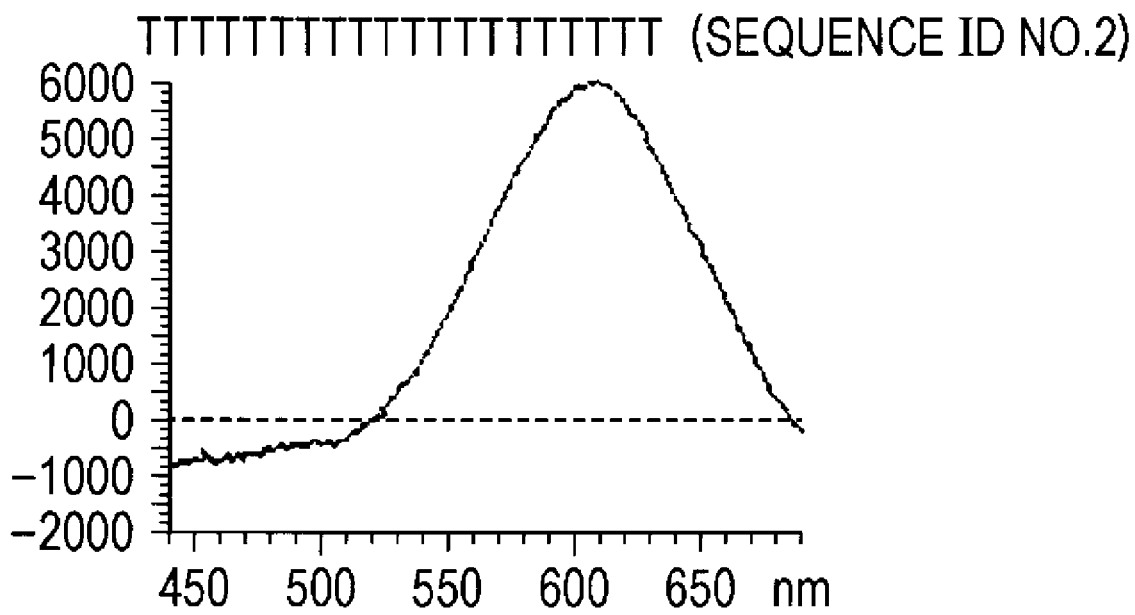

[Fig. 22A]
TTTTTTTTTTTTTTTTTTT (SEQUENCE ID NO.2)
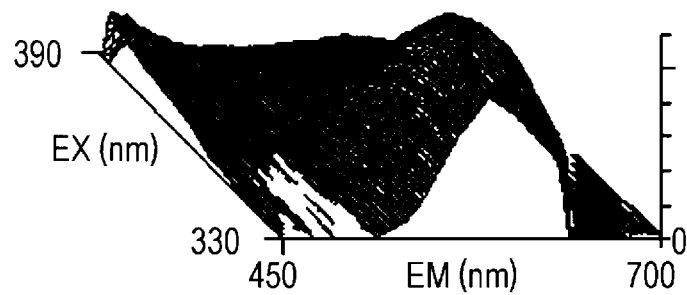
TTTTTTATTATTTATTTTTT (SEQUENCE ID NO.6)
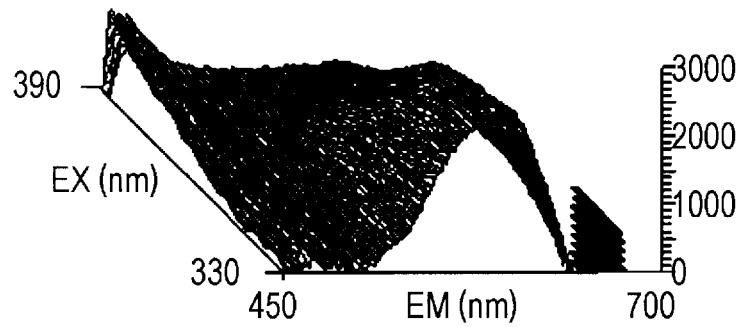
[Fig. 22B]
TTTTTTTTTTTTTTTTTTT (SEQUENCE ID NO.2)
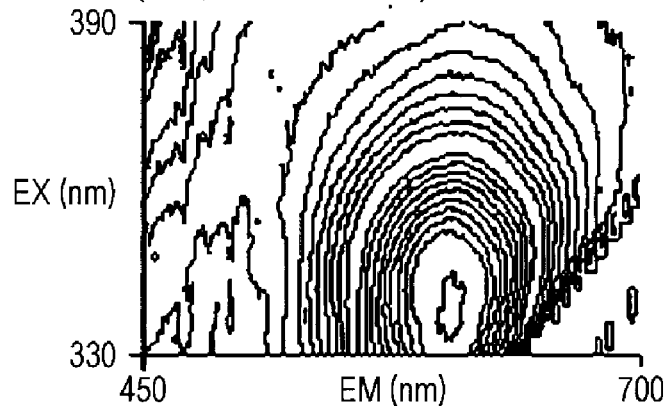
TTTTTTATTATTTATTTTTT (SEQUENCE ID NO.6)
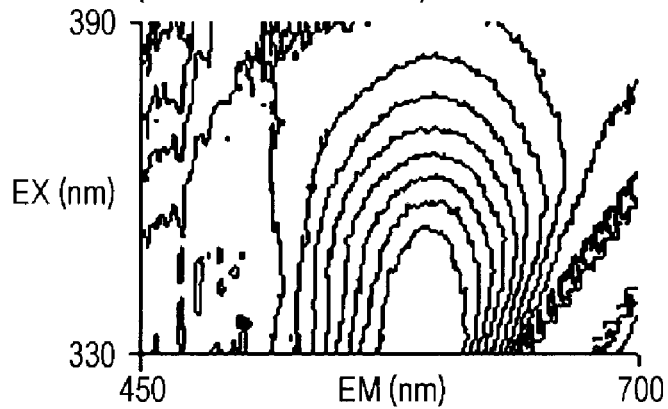

[Fig. 23]
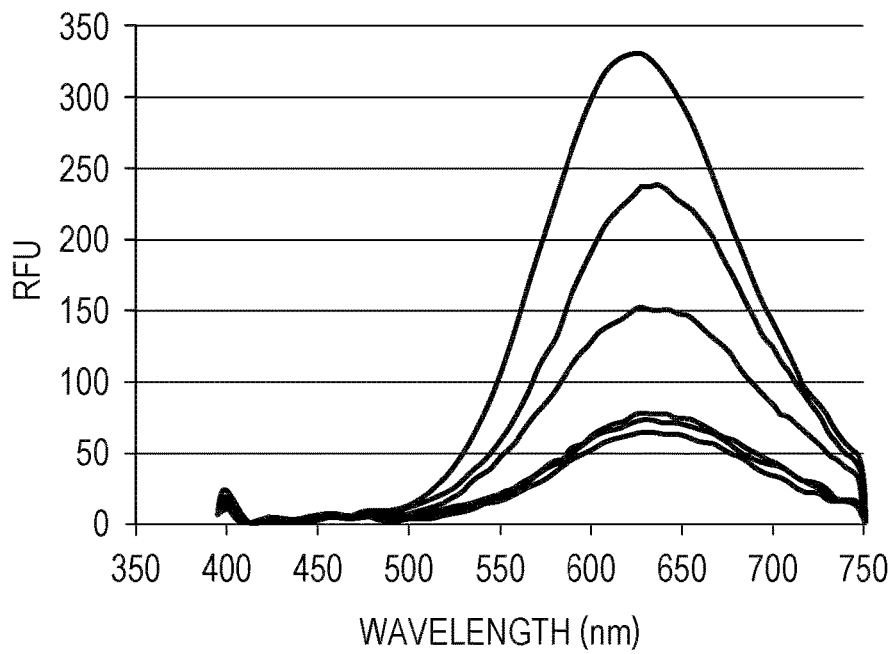
— CCCCTTTTTTTTTTTTCCCC  (SEQUENCE ID NO.21)
— CCCCCCCCTTTTTTTTTTTT  (SEQUENCE ID NO.22)
— TTTTTTTTTTTTCCCCCCCC  (SEQUENCE ID NO.23)
— CCTTTTTTCCCCTTTTTTCC  (SEQUENCE ID NO.24)
— CTTTCCTTTCCTTTCCTTTC  (SEQUENCE ID NO.25)
— CCTTCTTCTTCTTCTTCTTC  (SEQUENCE ID NO.26)
[Fig. 24A]
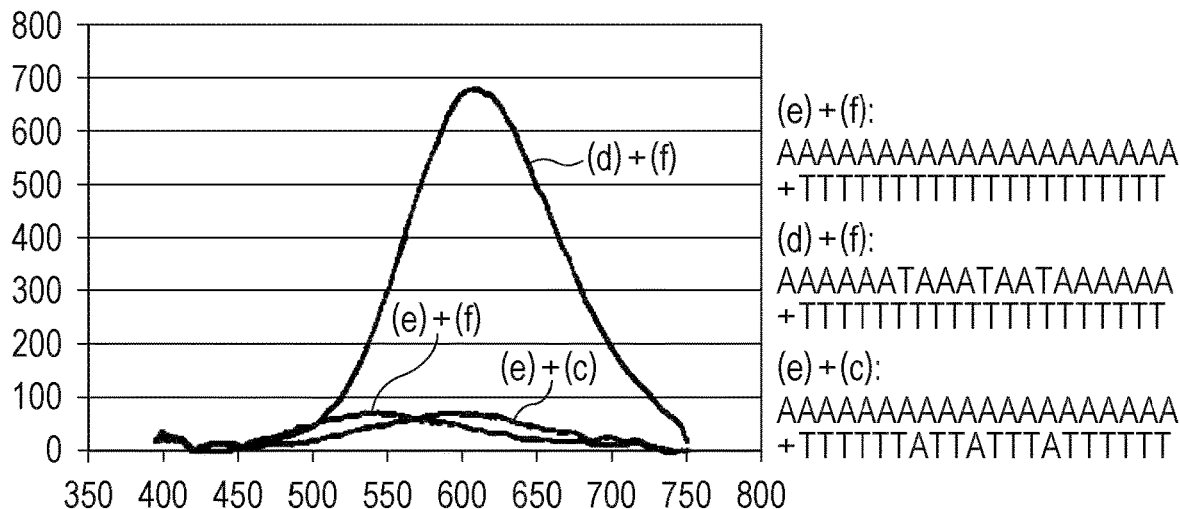

[Fig. 24B]
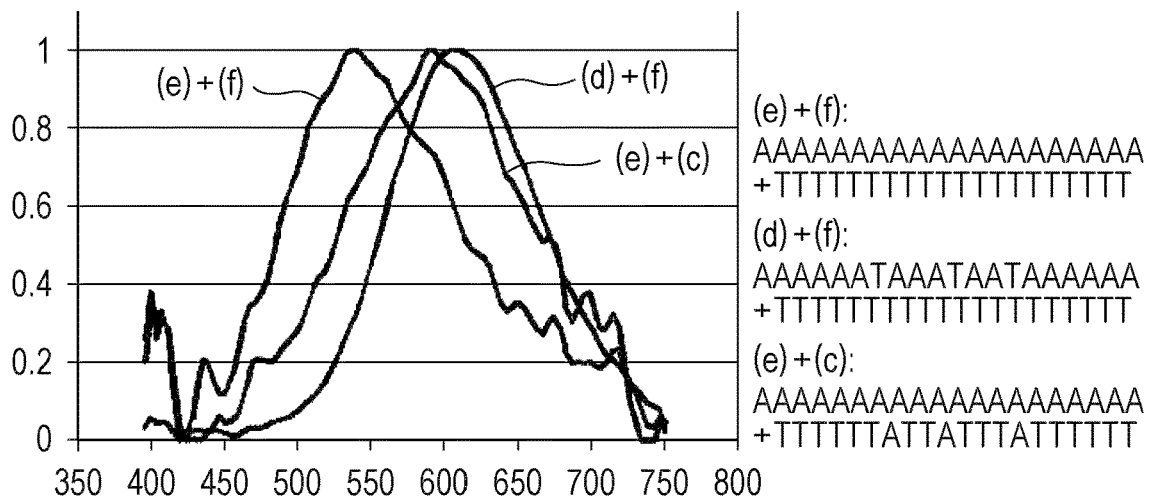
(c) SEQUENCE ID NO.6: 5'-TTTTTTATTATTTATTTTTT-3'
(d) SEQUENCE ID NO.5: 5'-AAAAAATAAATAATAAAAAA-3'
(e) SEQUENCE ID NO.1: 5'-AAAAAAAAAAAAAAAAAAAA-3'
(f) SEQUENCE ID NO.2: 5'-TTTTTTTTTTTTTTTTTTTT-3'
[Fig. 25A]
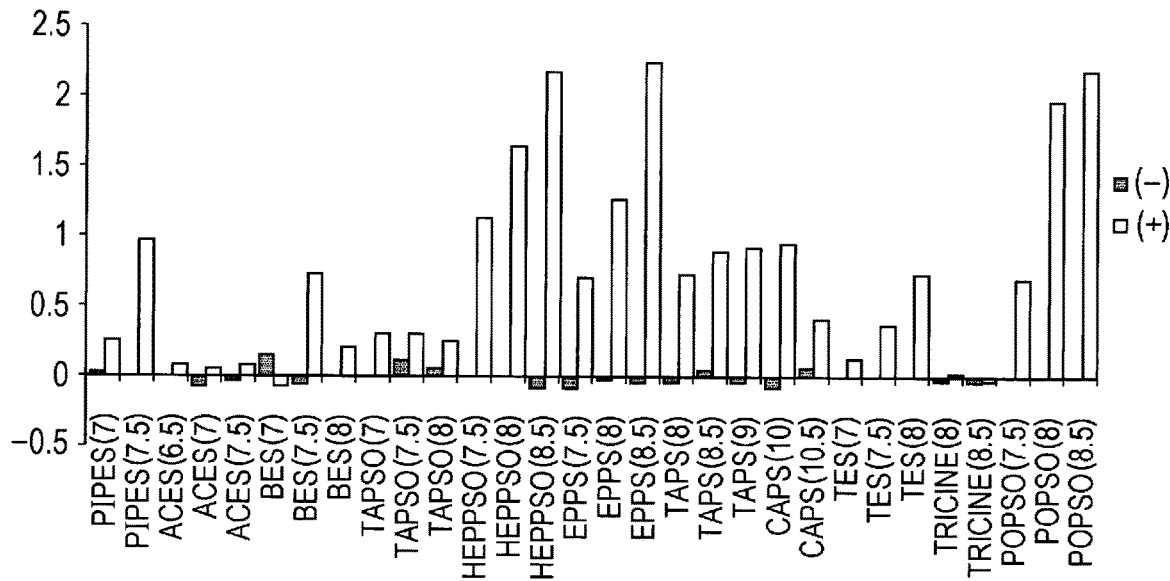

[Fig. 25B]
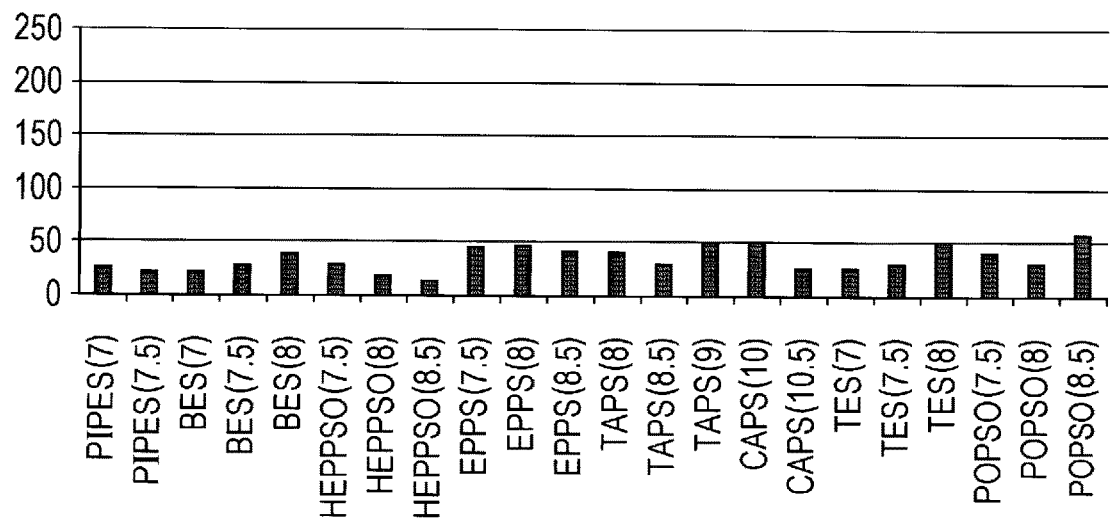
[Fig. 25C]
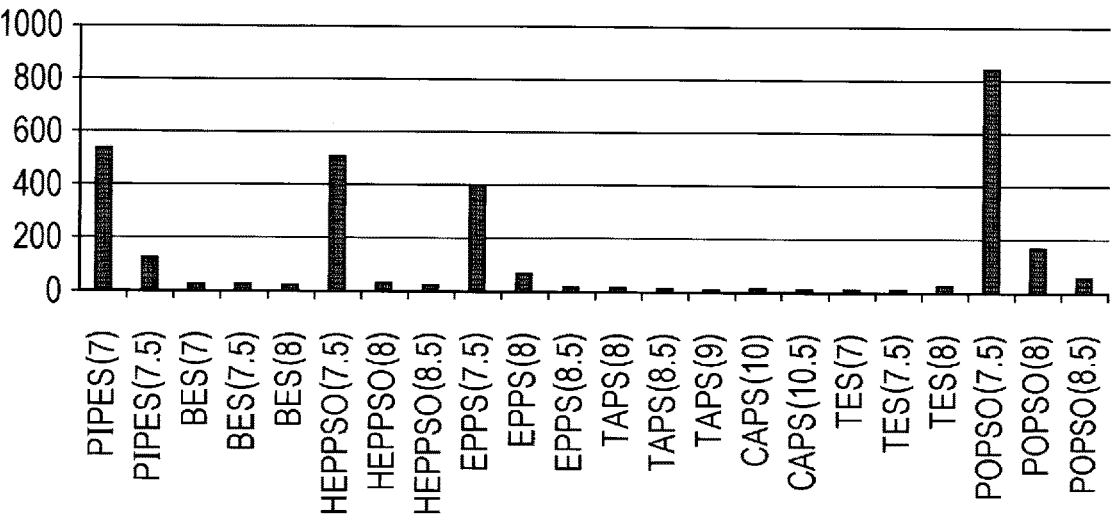
[Fig. 26A]
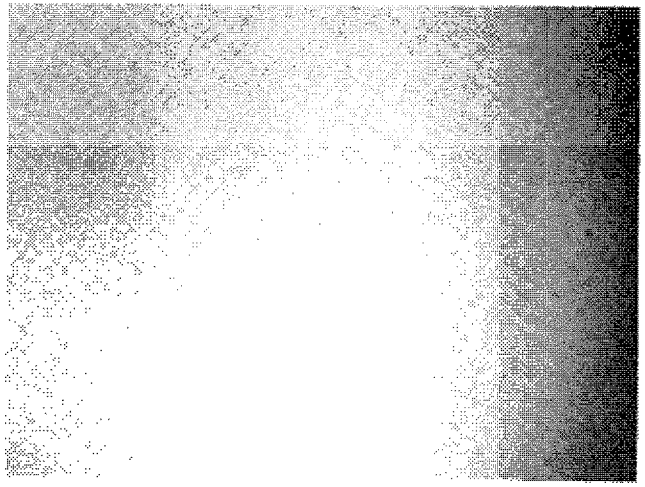

[Fig. 26B]
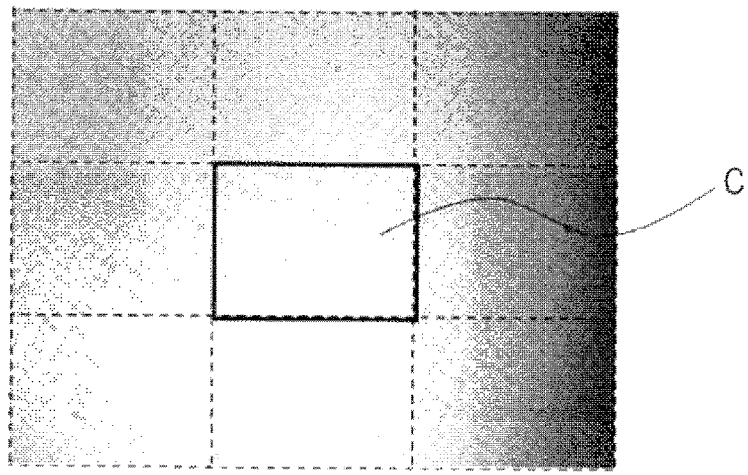
[Fig. 27A]
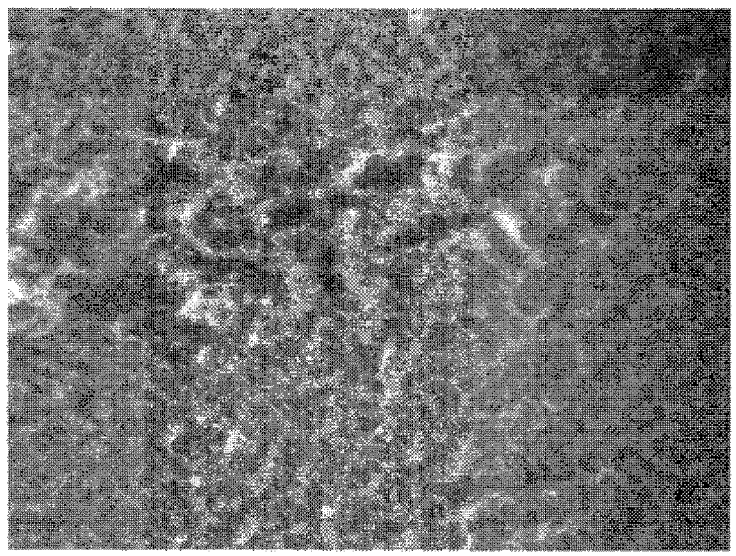
[Fig. 27B]
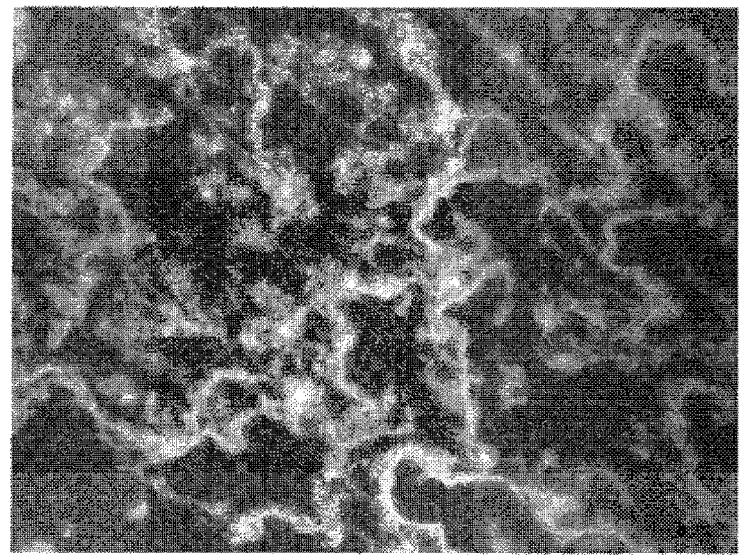

[Fig. 28]
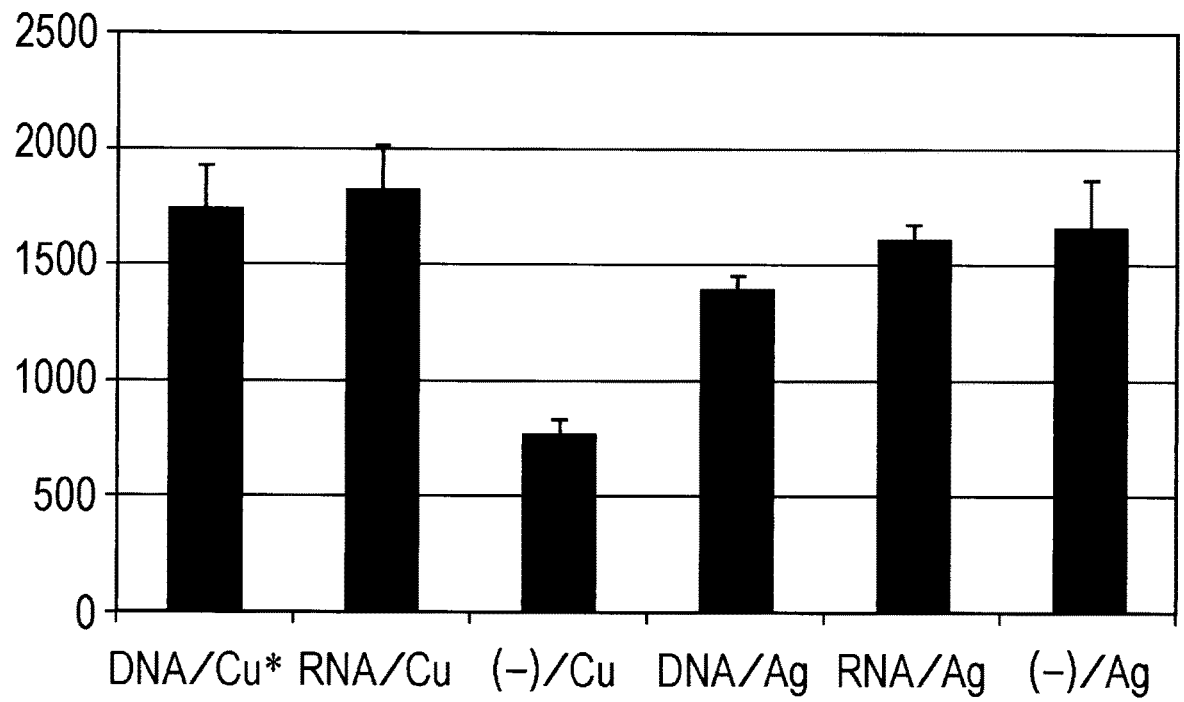
[Fig. 29]
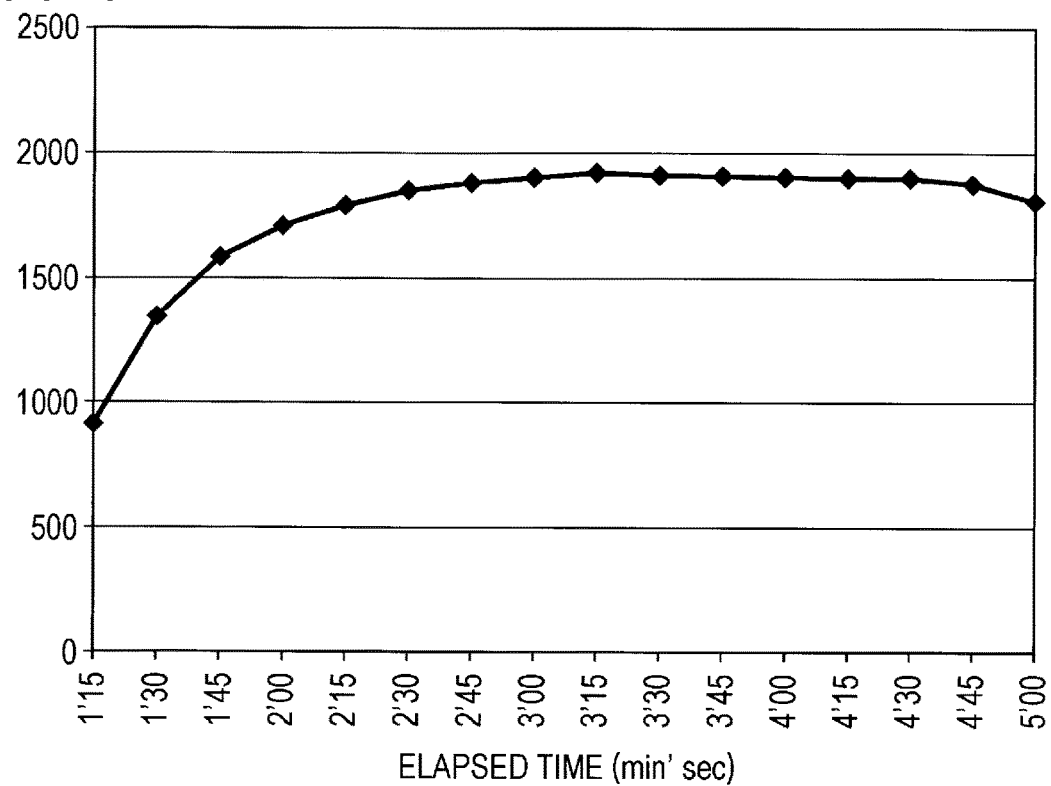

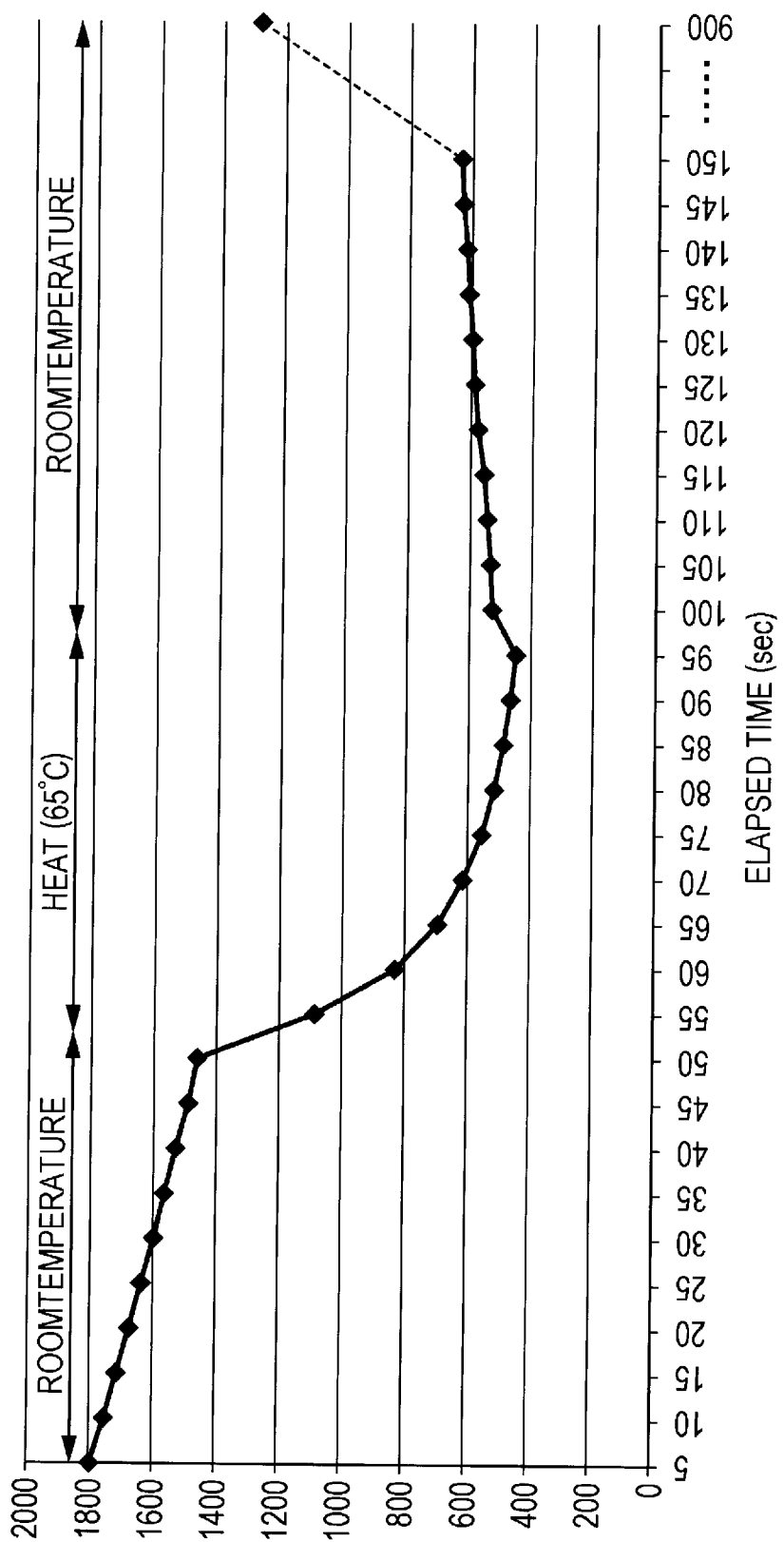
[Fig. 30]

[Fig. 31A]
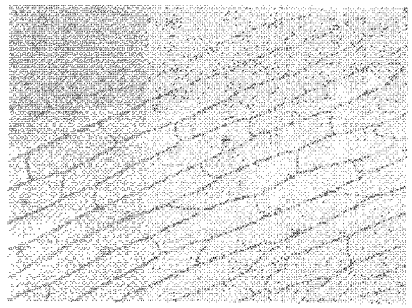
[Fig. 31B]
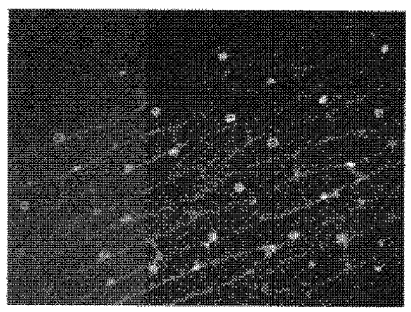
[Fig. 31C]
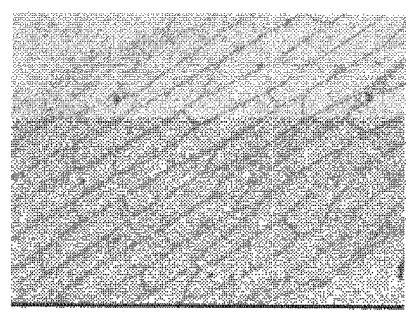
[Fig. 31D]
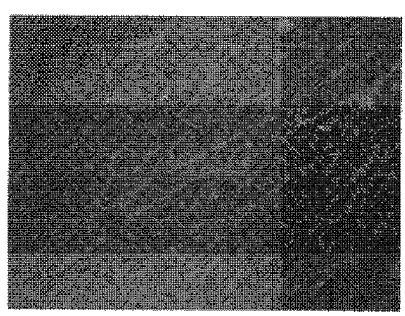
[Fig. 31E]
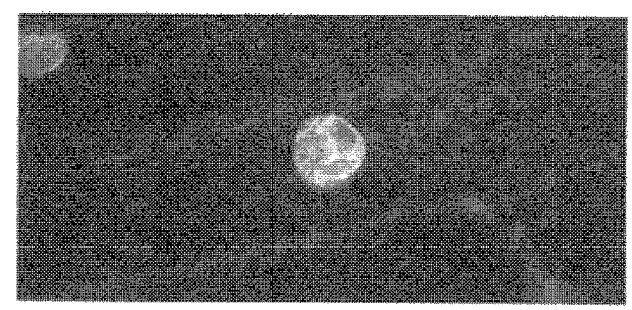

[Fig. 32A]
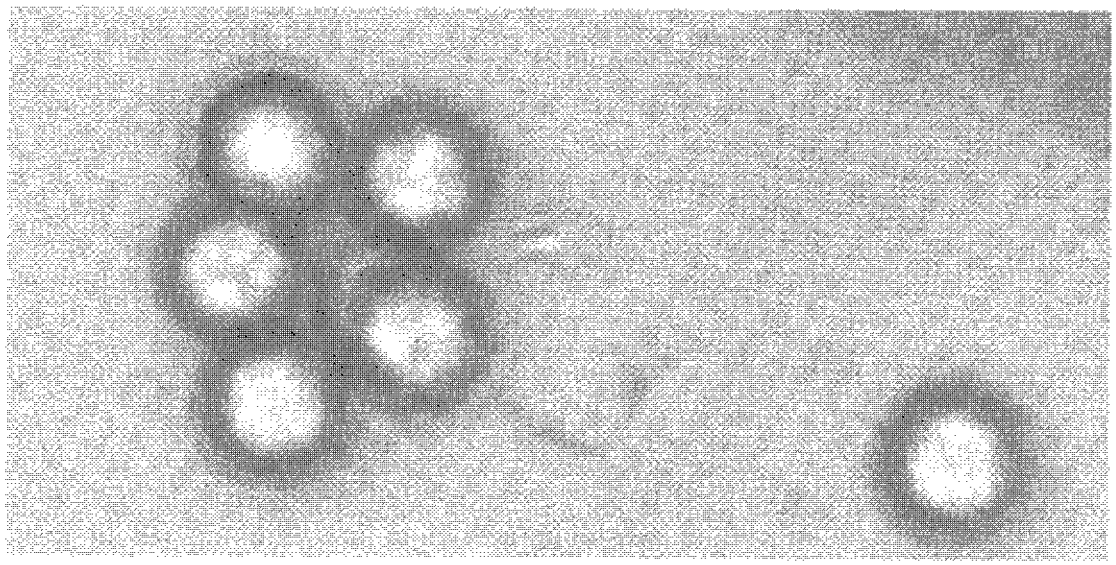
[Fig. 32B]
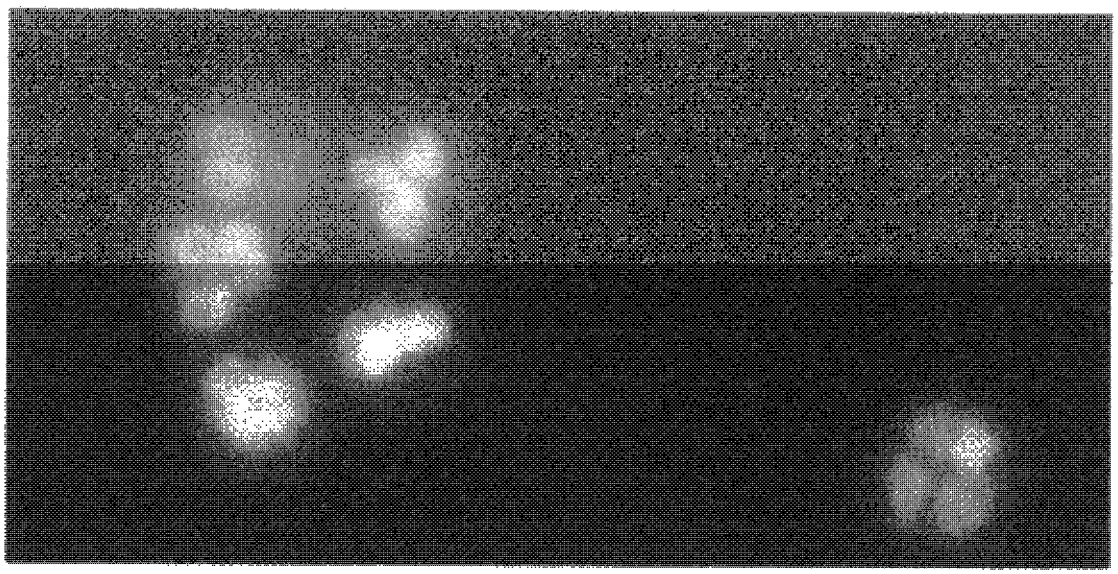
[Fig. 33A]

[Fig. 33B]
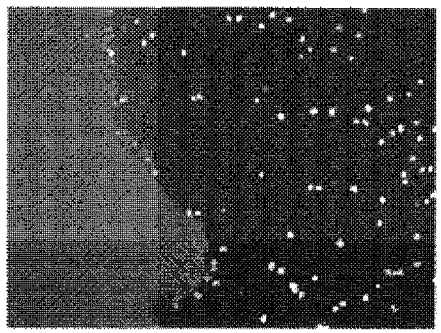
[Fig. 33C]
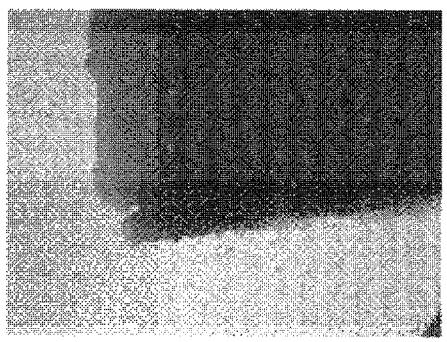
[Fig. 33D]
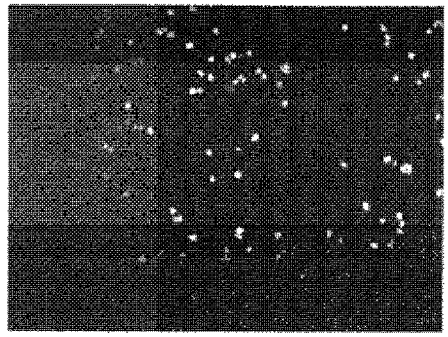
[Fig. 34A]
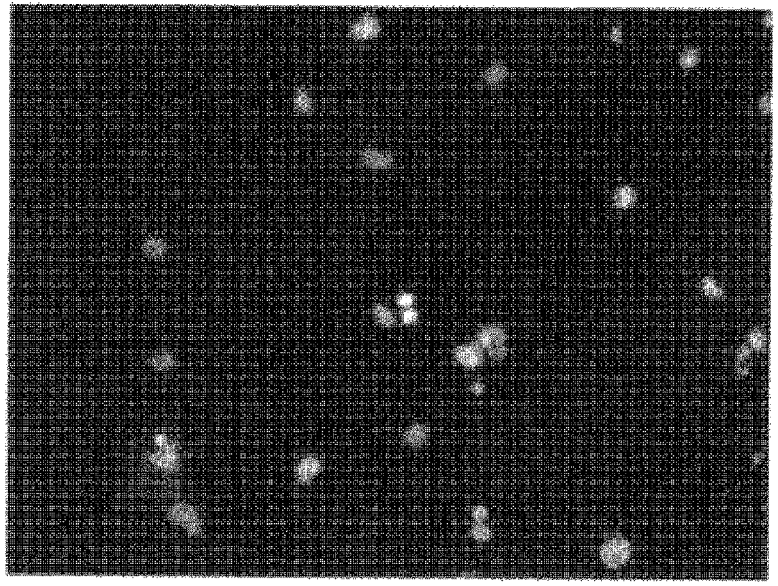

[Fig. 34B]
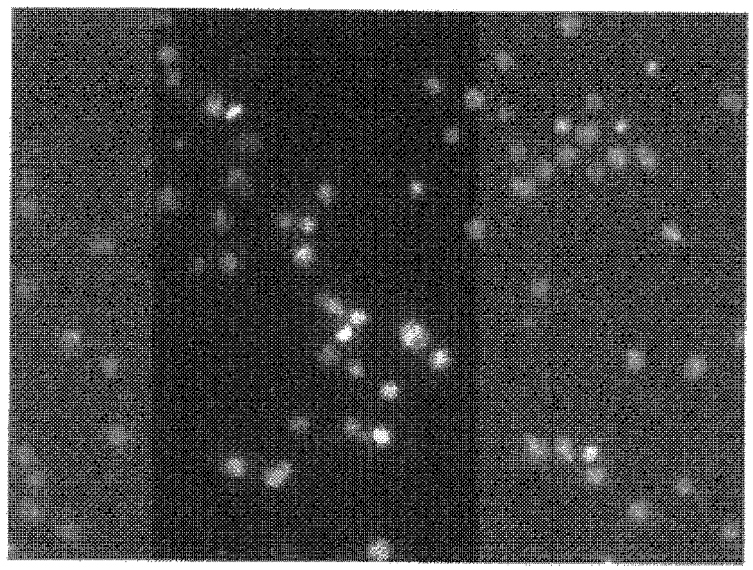
[Fig. 35A]
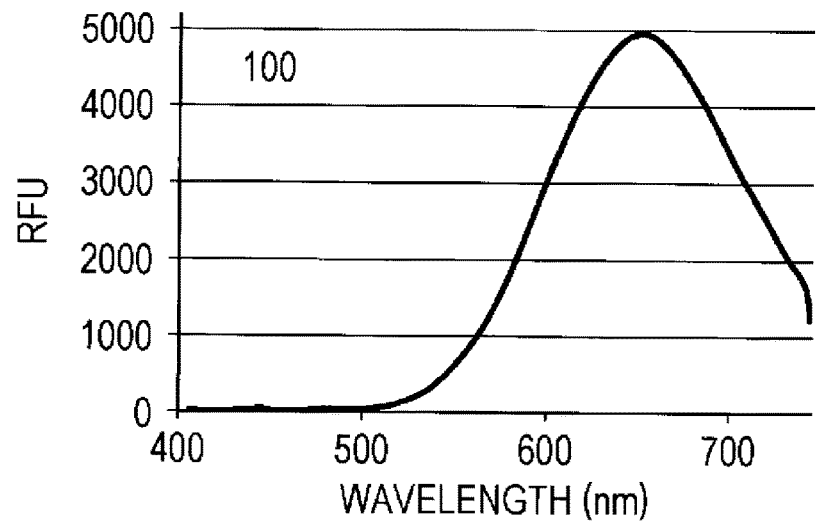
[Fig. 35B]
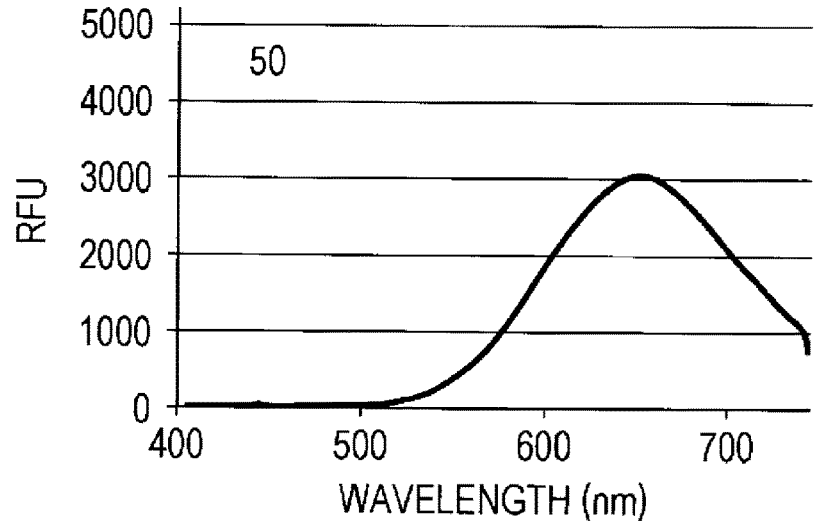

[Fig. 35C]
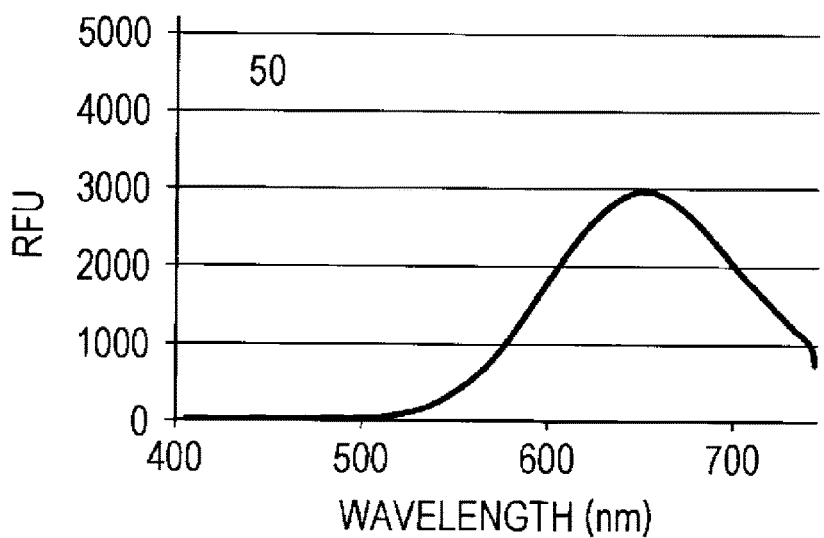
[Fig. 35D]
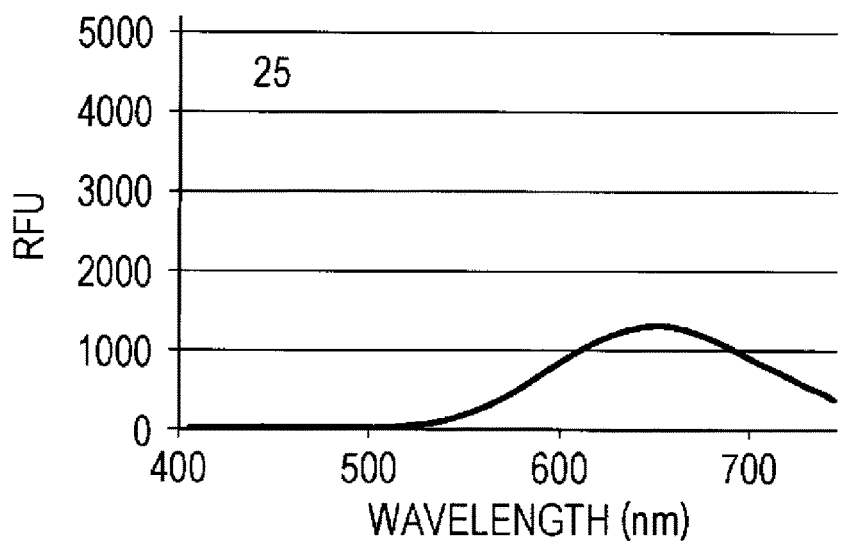
[Fig. 35E]
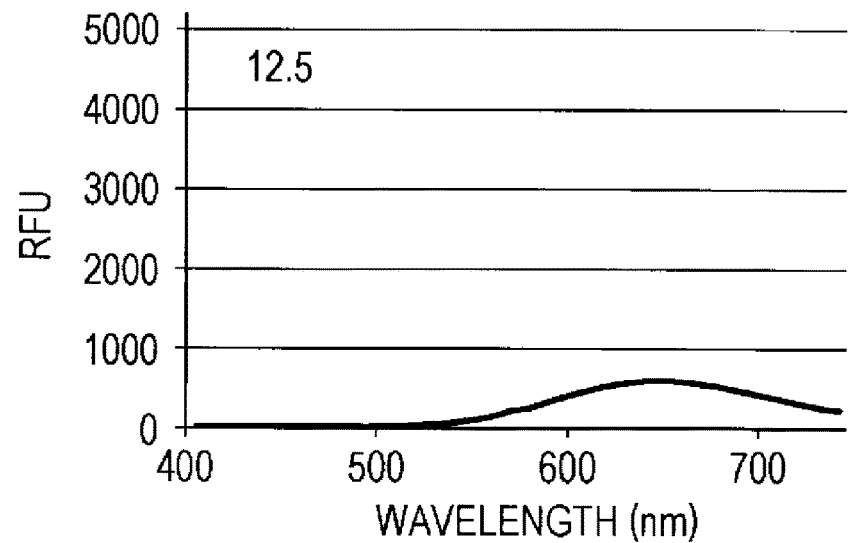

[Fig. 35F]
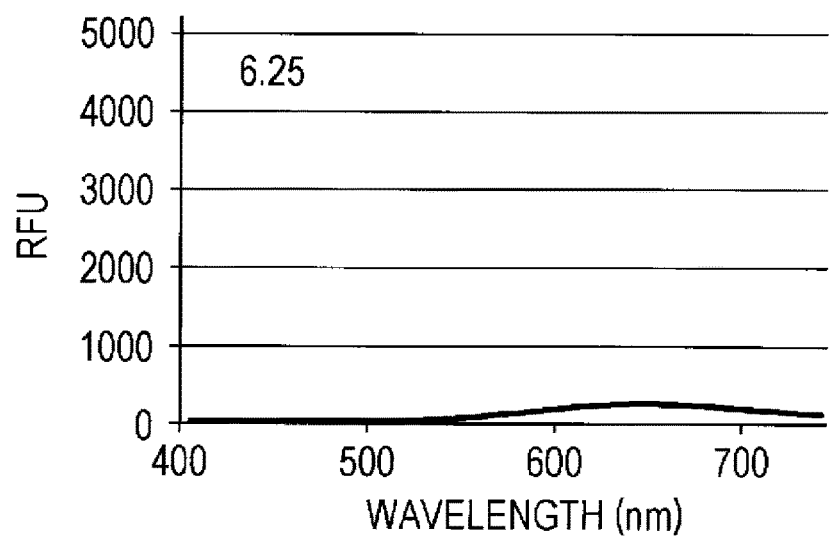
[Fig. 36A]
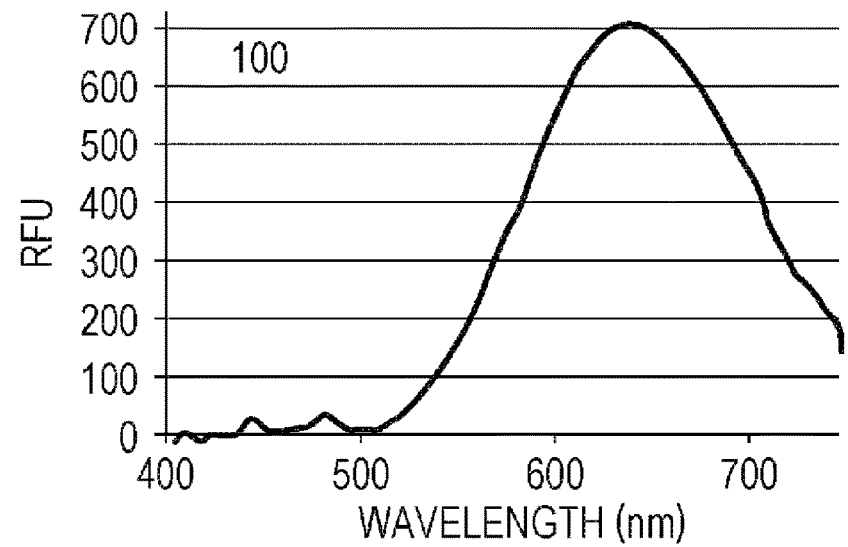
[Fig. 36B]
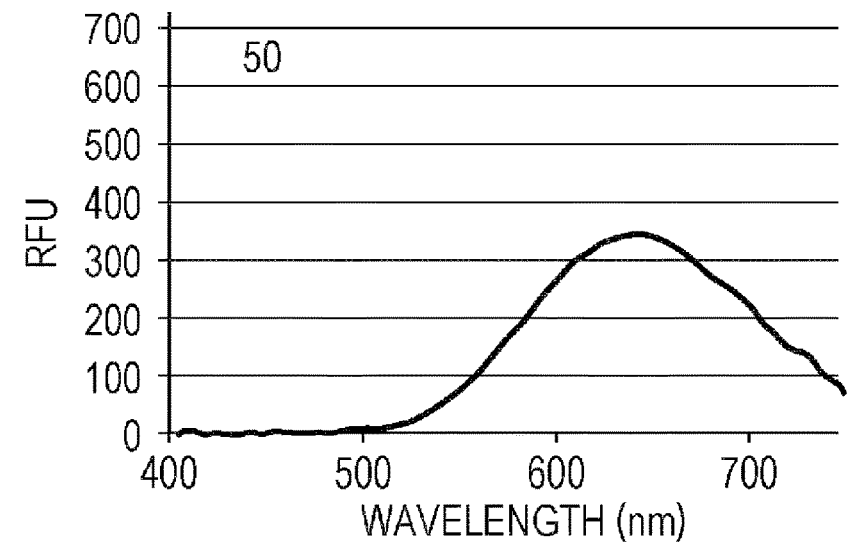

[Fig. 36C]
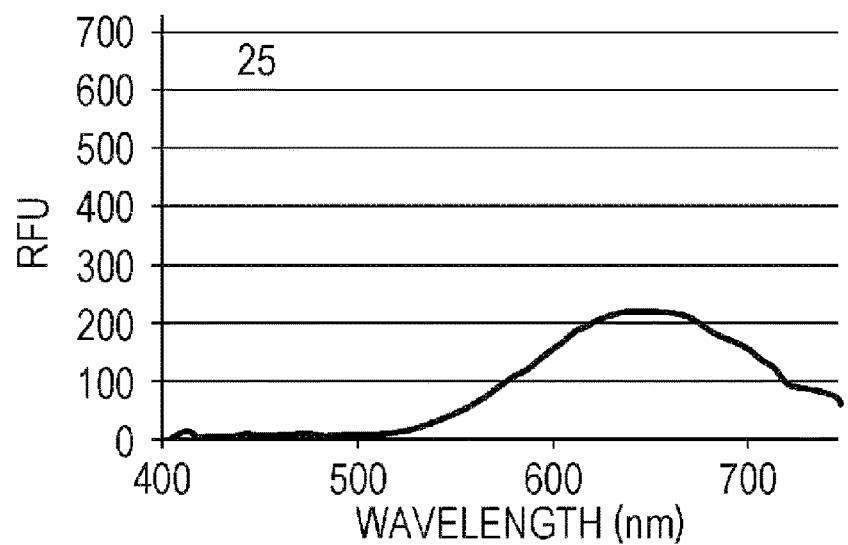
[Fig. 36D]
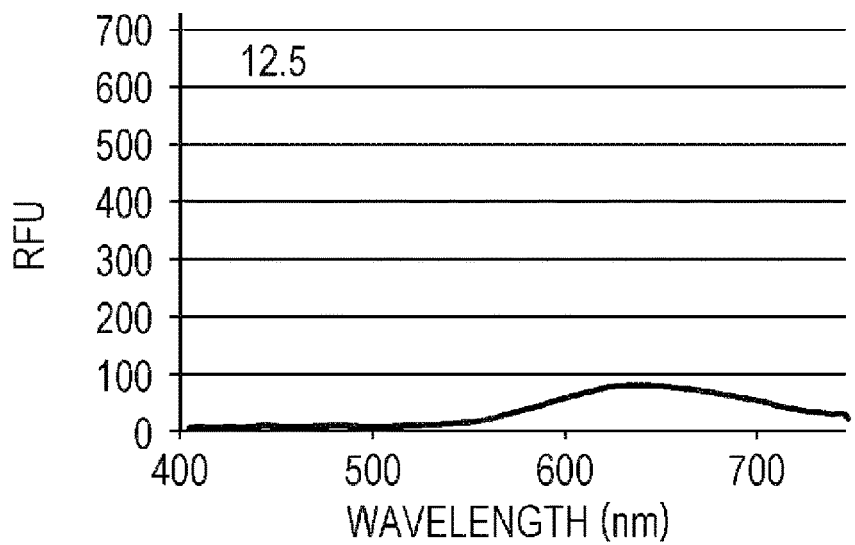
[Fig. 36E]
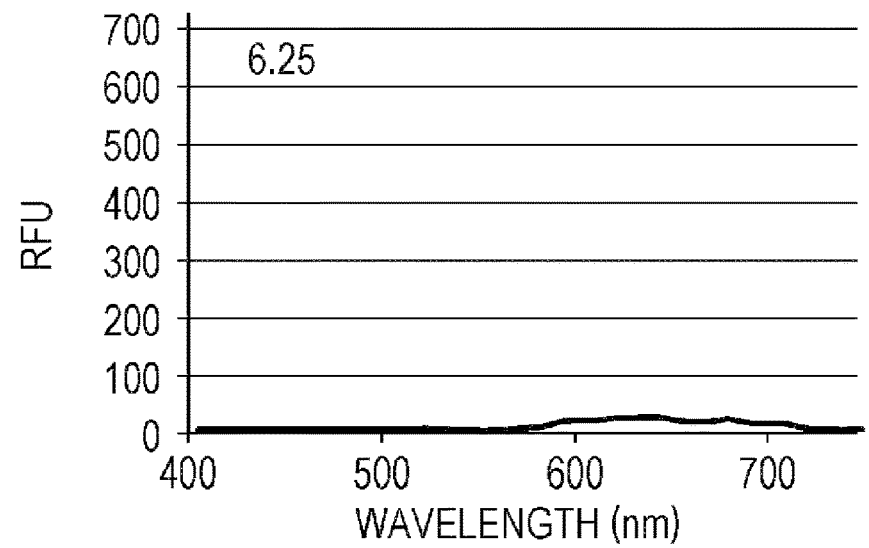

[Fig. 37A]
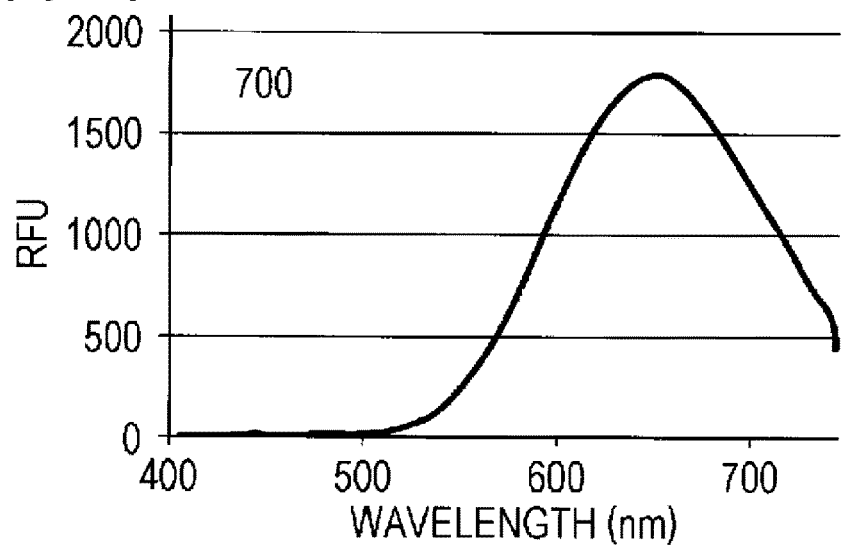
[Fig. 37B]
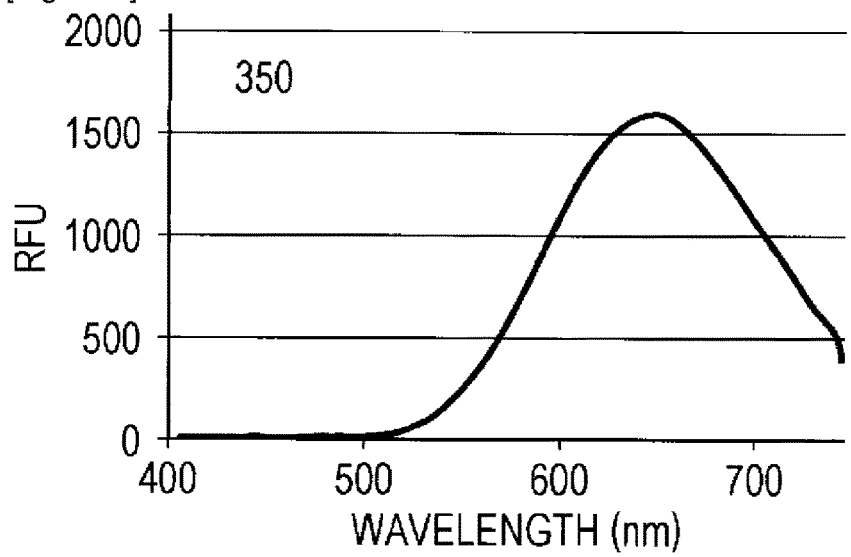
[Fig. 37C]
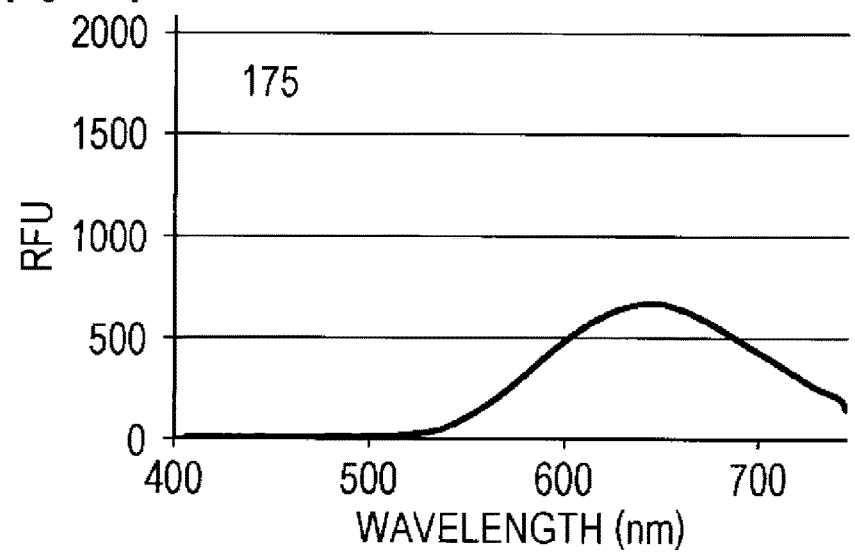

[Fig. 37D]
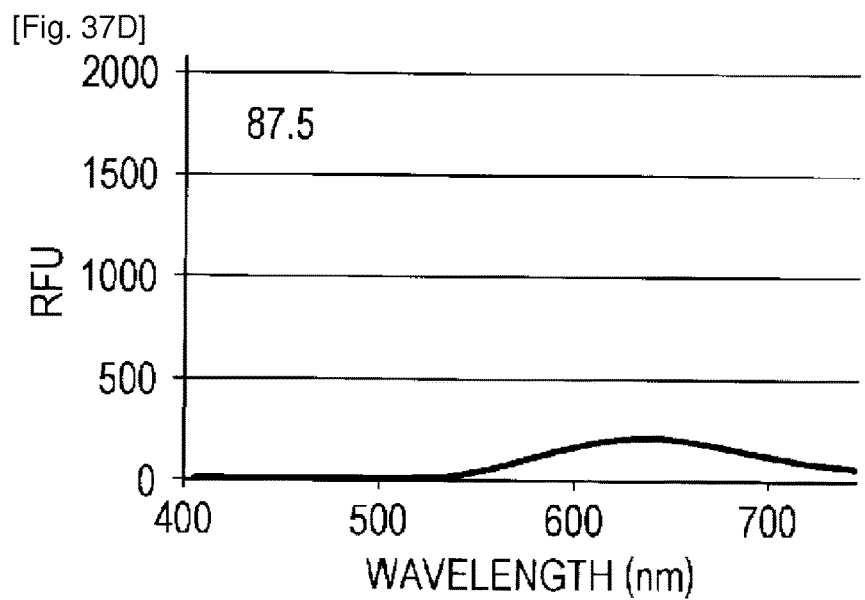
[Fig. 37E]
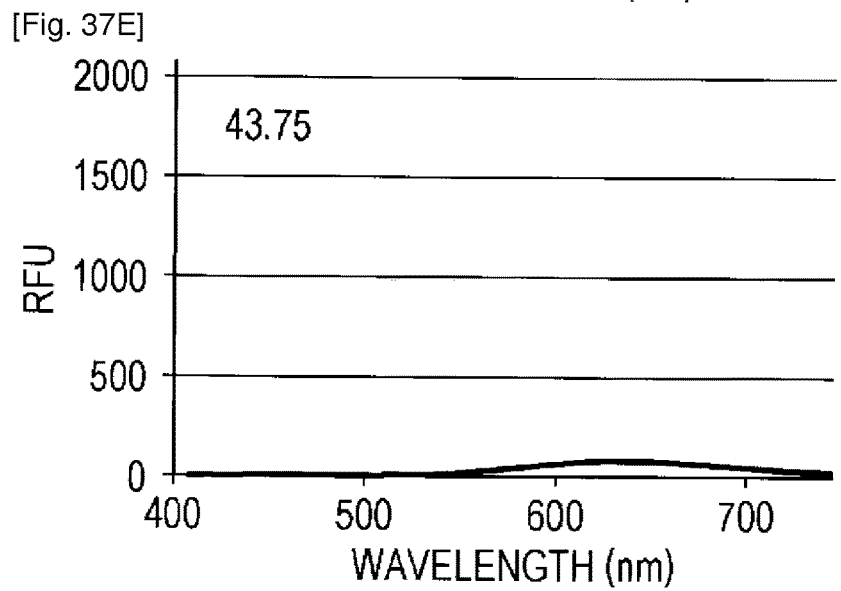
[Fig. 38A]
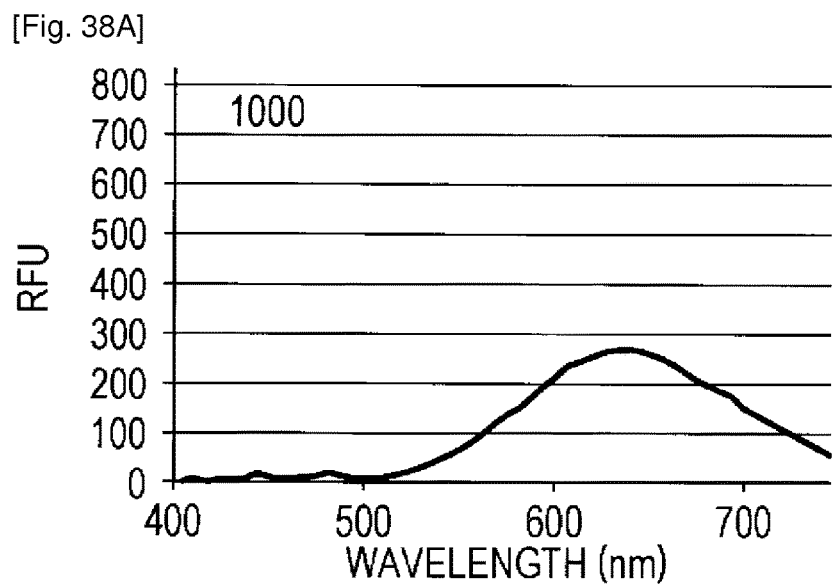

[Fig. 38B]
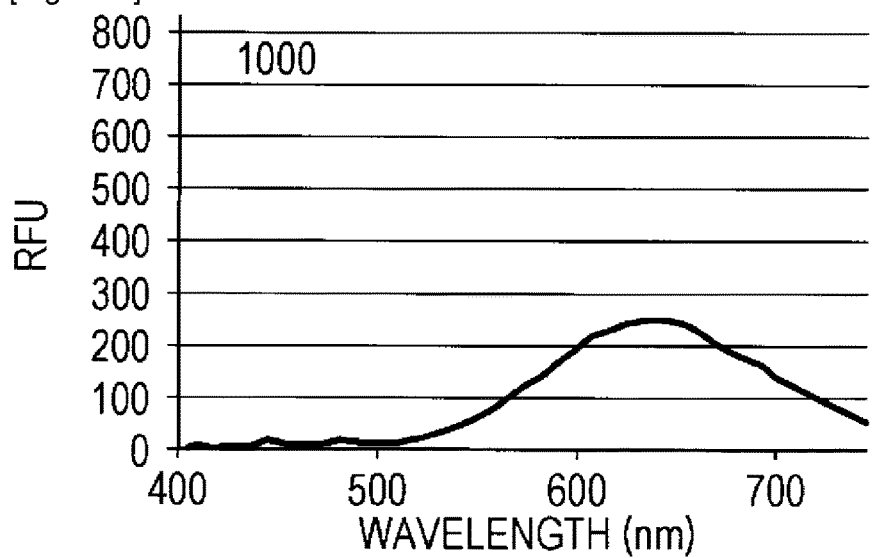
[Fig. 38C]
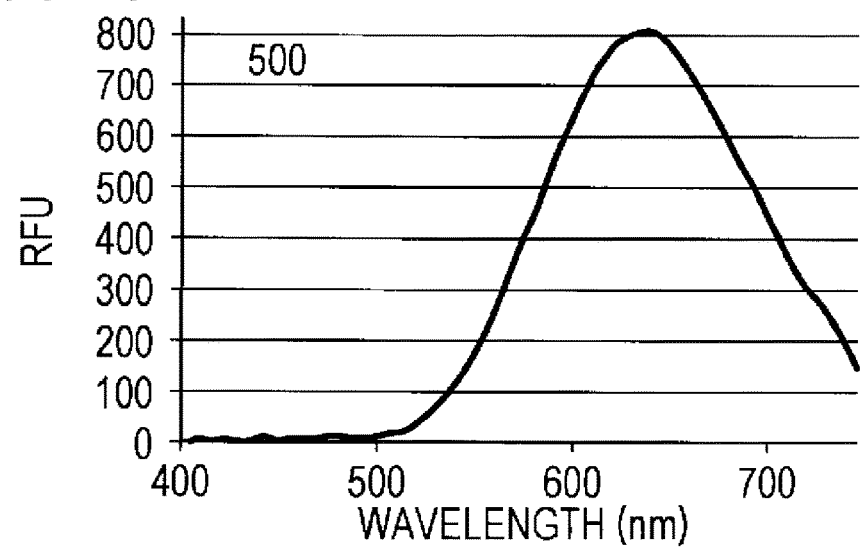
[Fig. 38D]
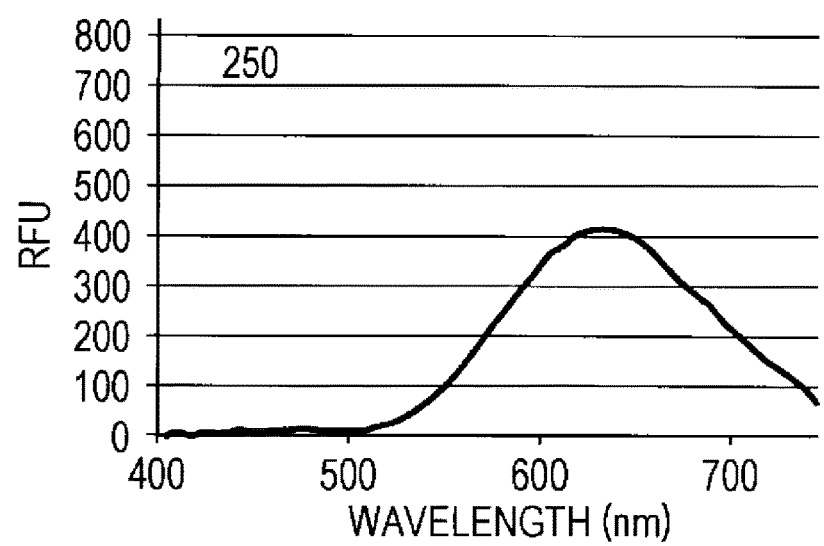

[Fig. 38E]
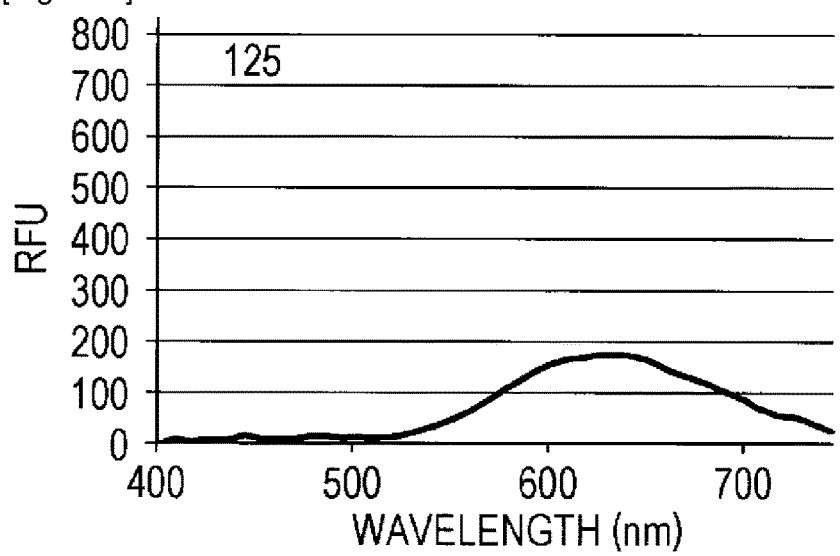
[Fig. 38F]
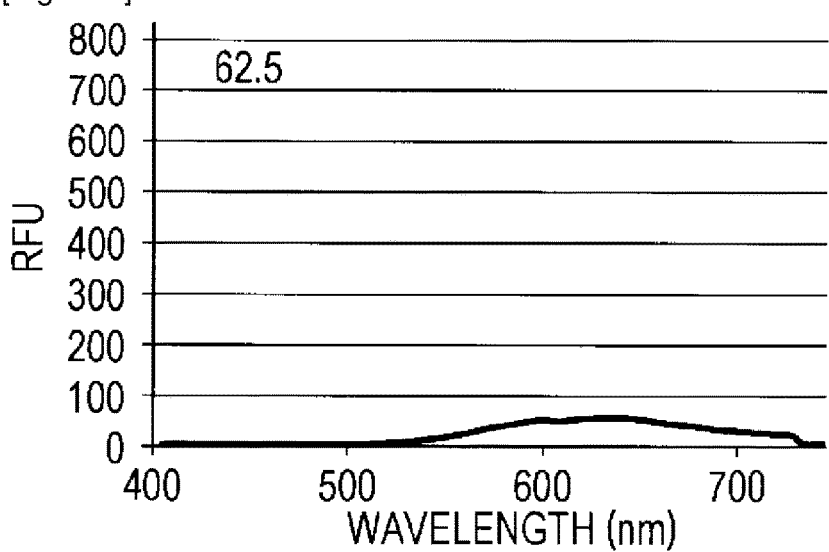
[Fig. 39A]
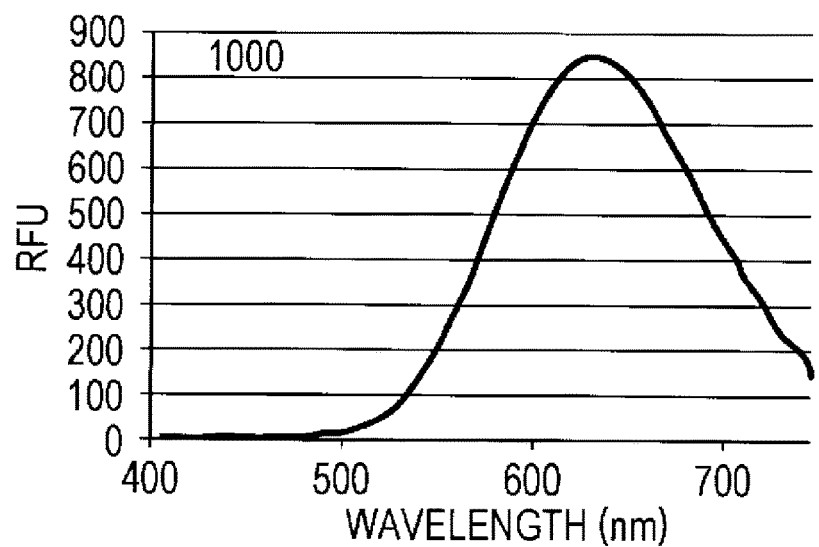

[Fig. 39B]
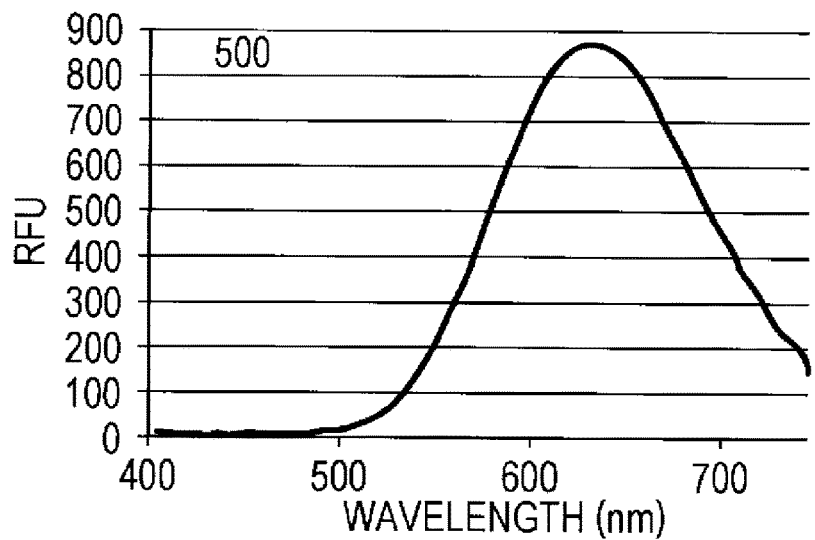
[Fig. 39C]
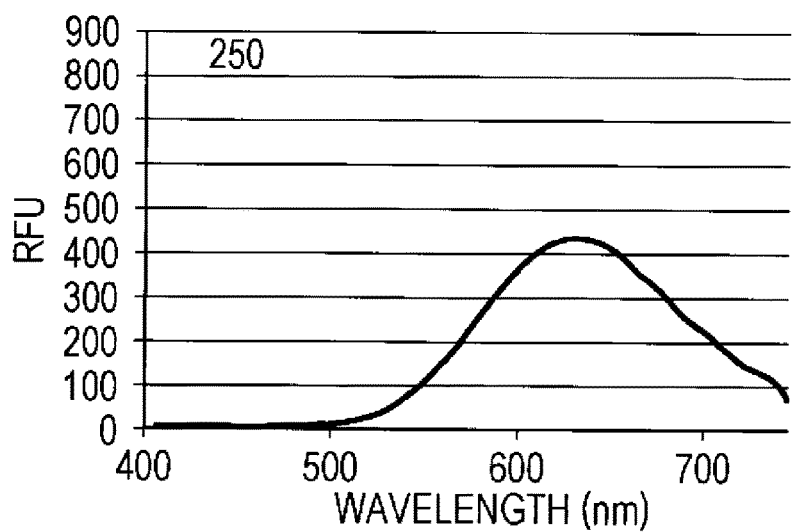
[Fig. 39D]
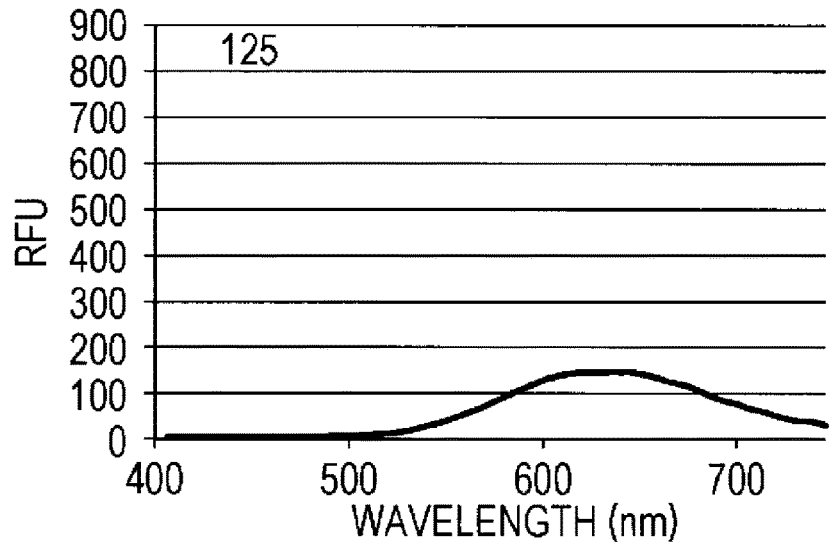

[Fig. 39E]
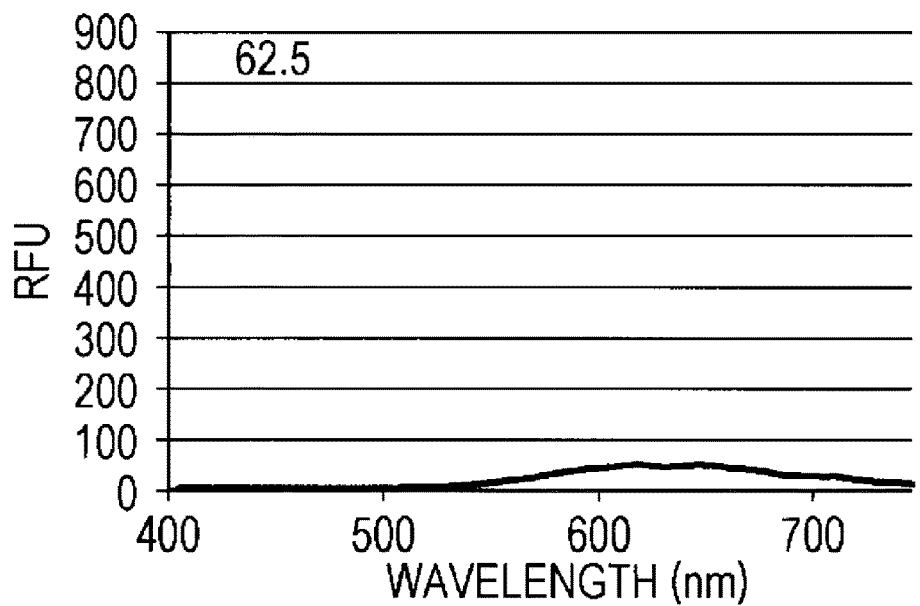
[Fig. 40A]
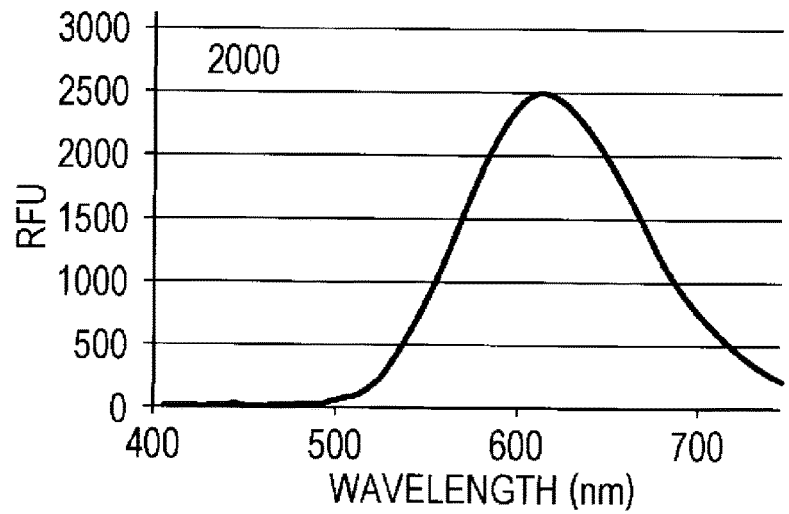
[Fig. 40B]
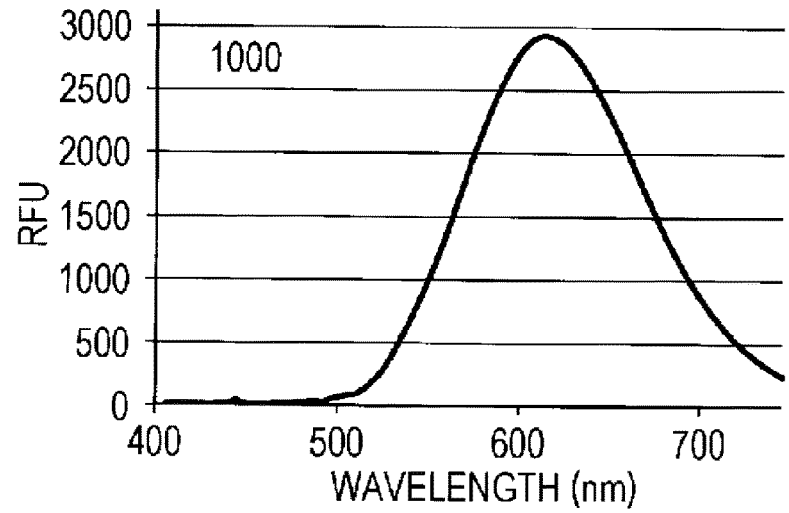

[Fig. 40C]
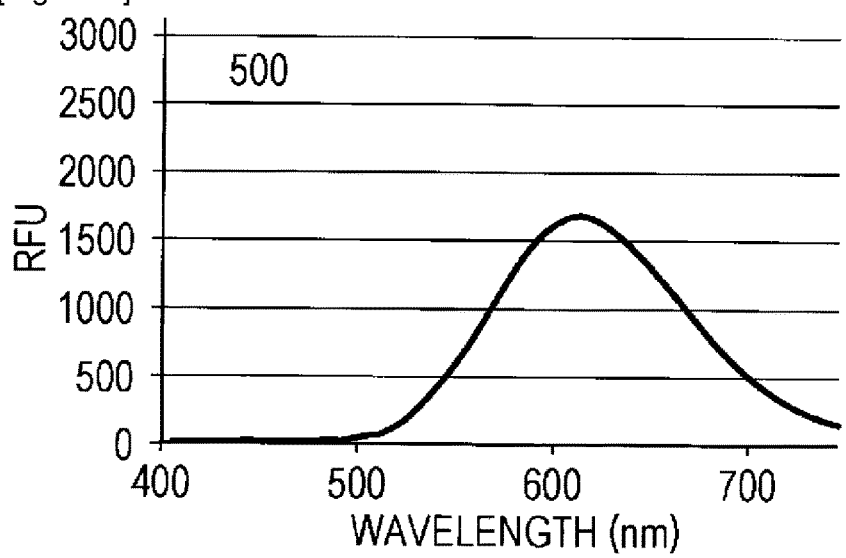
[Fig. 40D]
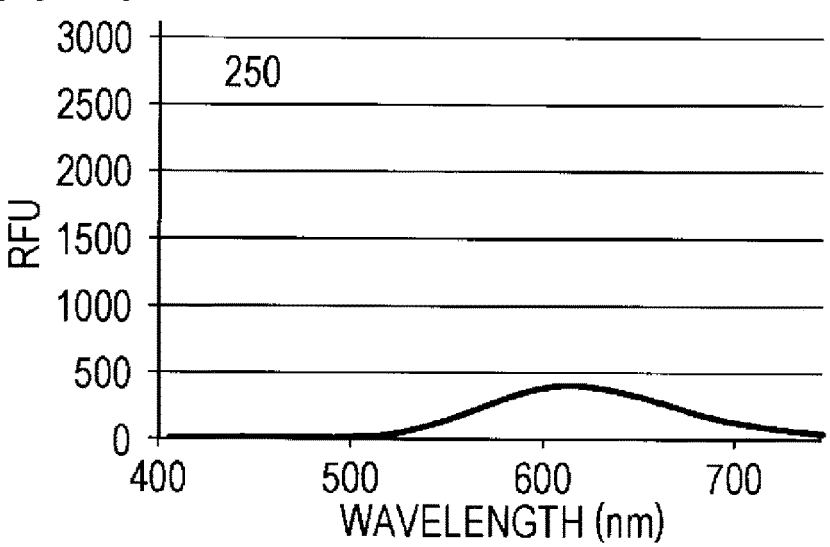
[Fig. 40E]
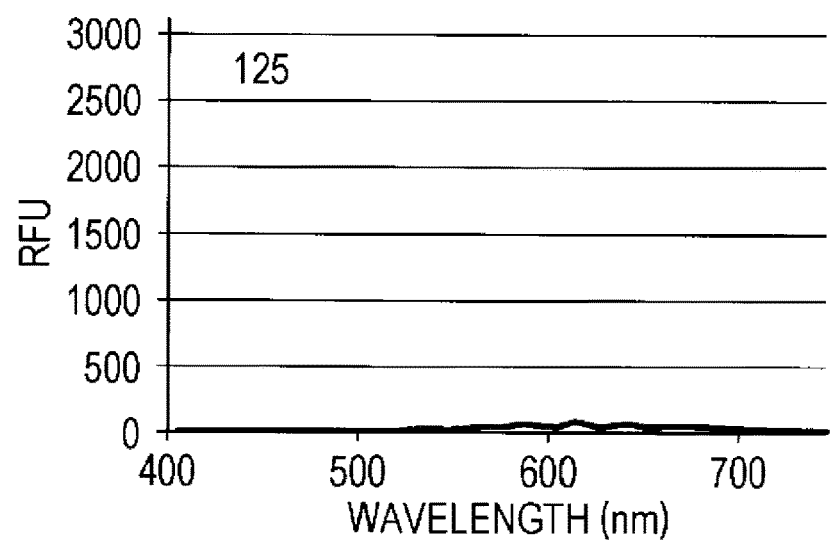

[Fig. 41A]
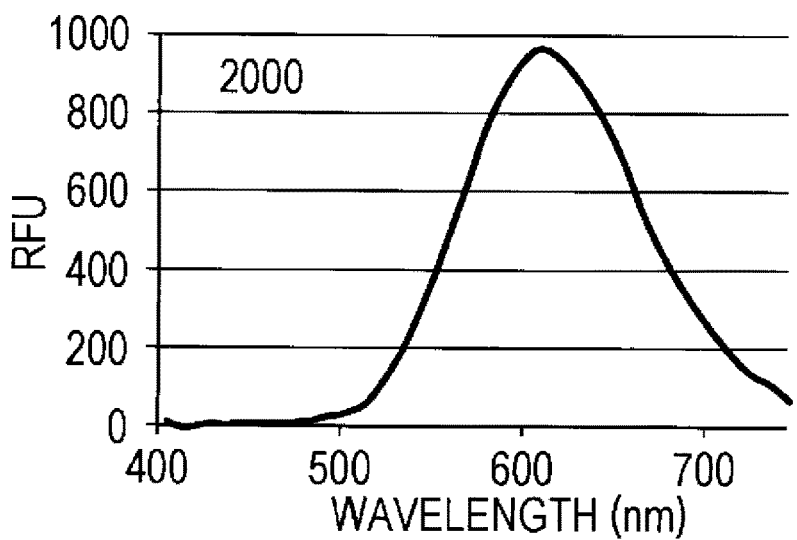
[Fig. 41B]
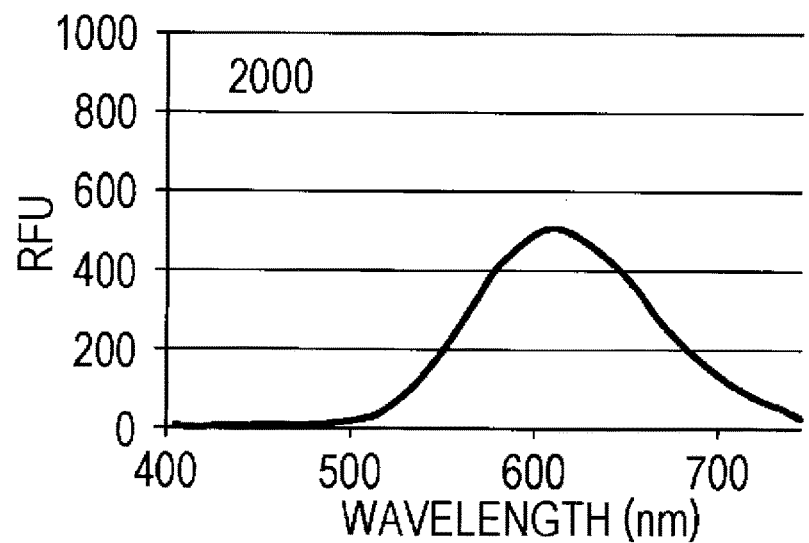
[Fig. 41C]
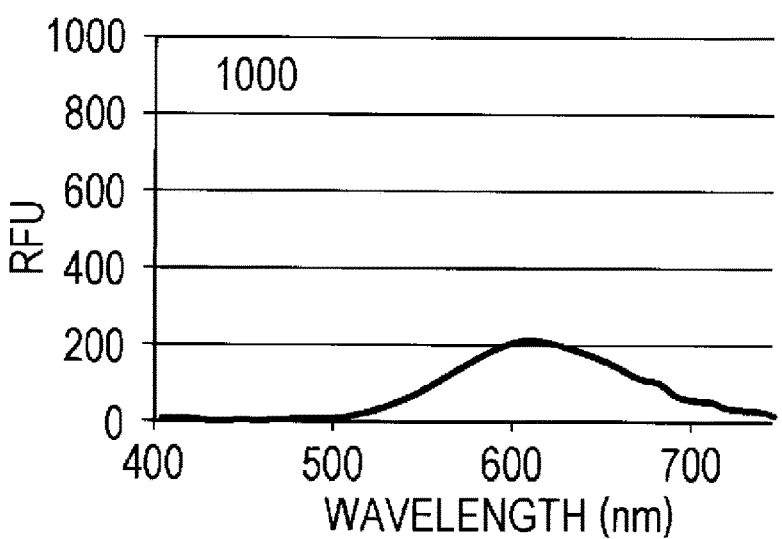

[Fig. 41D]
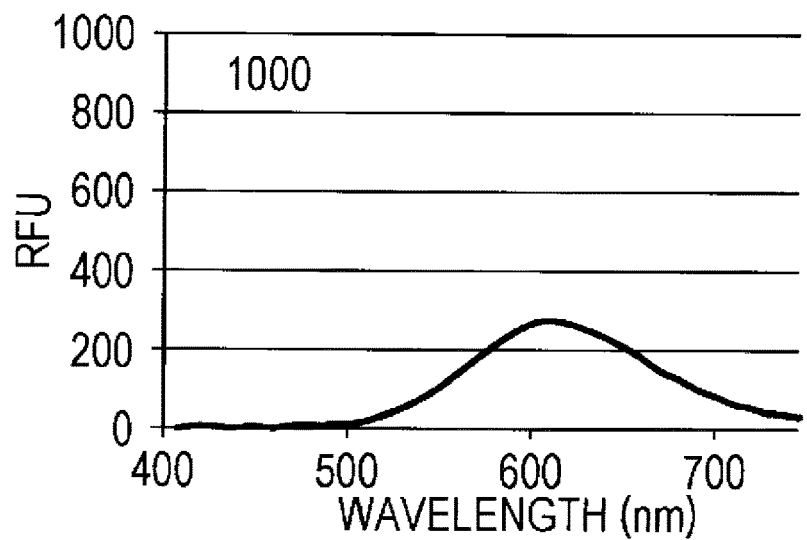
[Fig. 41E]
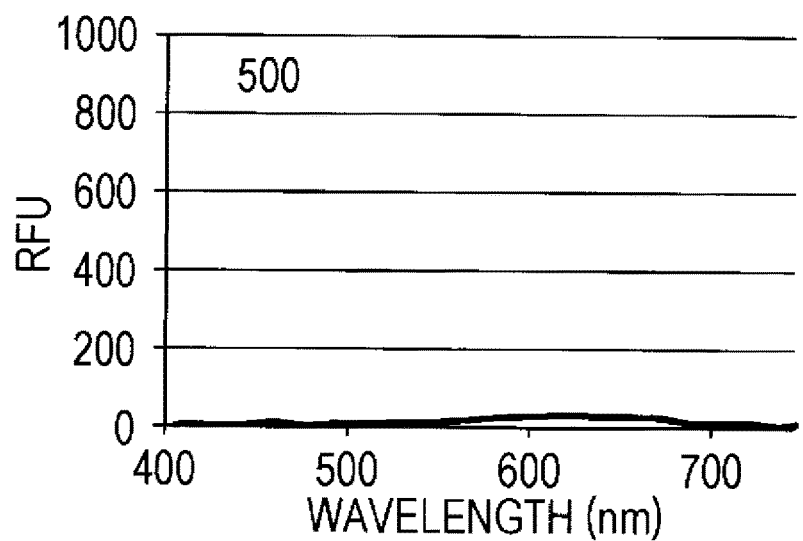
[Fig. 41F]
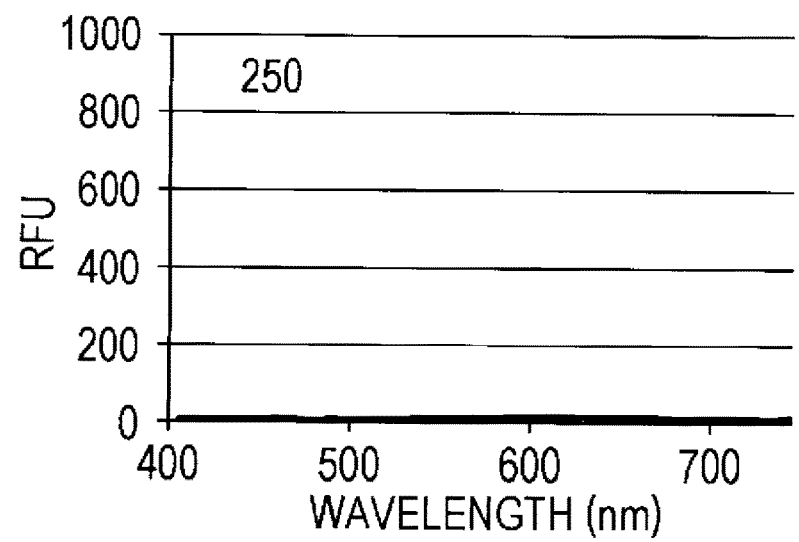

[Fig. 41G]
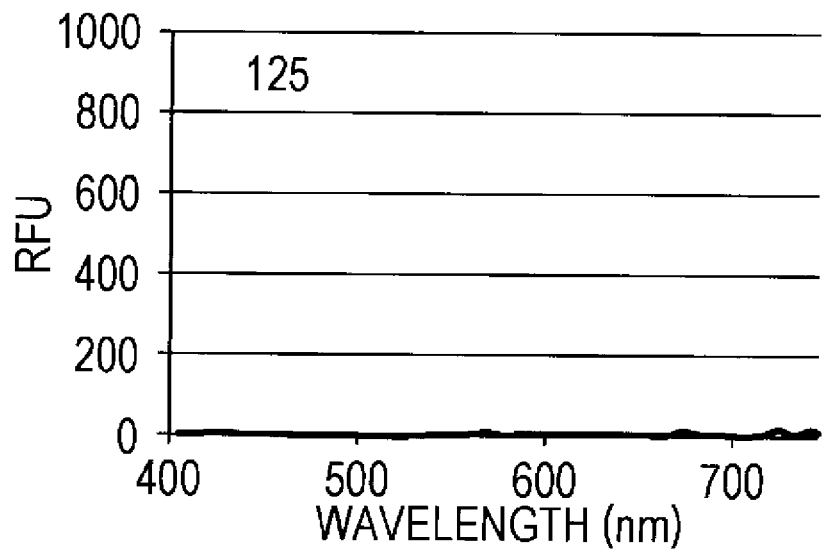
[Fig. 42A]
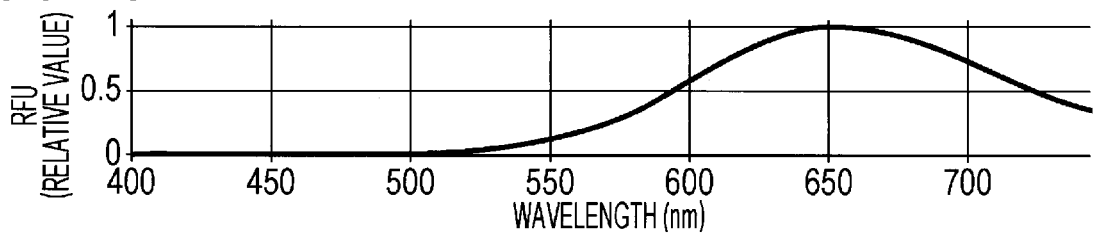
[Fig. 42B]
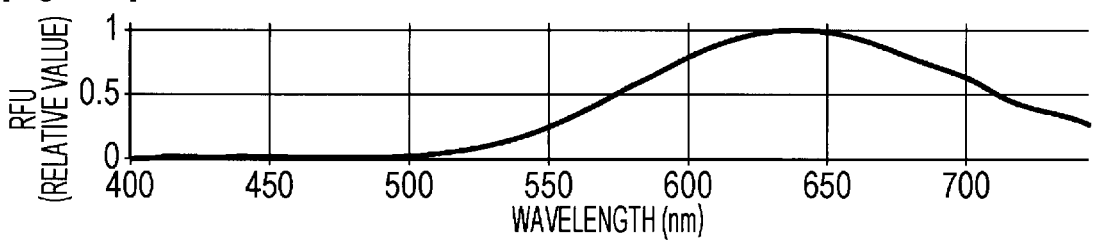
[Fig. 42C]
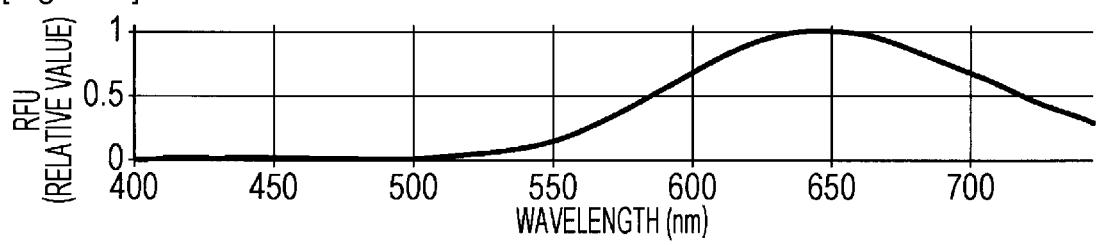
[Fig. 42D]
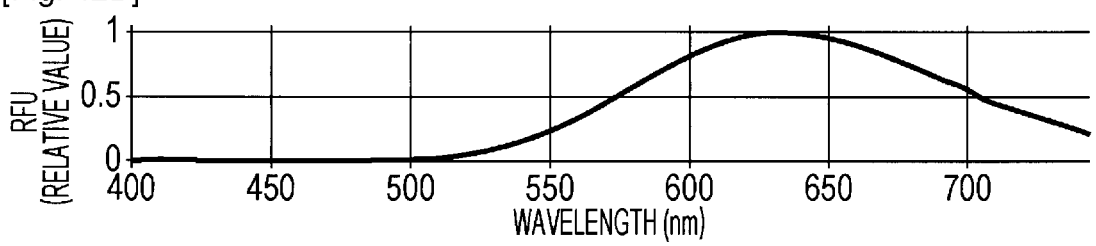

[Fig. 42E]
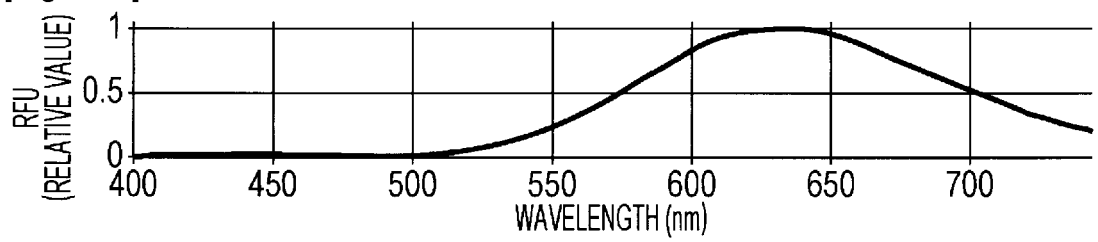
[Fig. 42F]
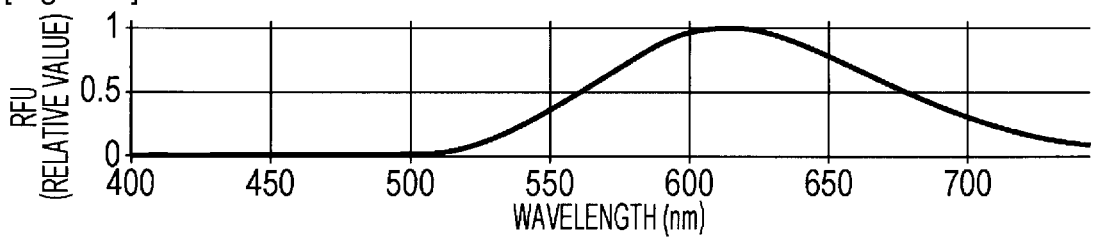
[Fig. 42G]
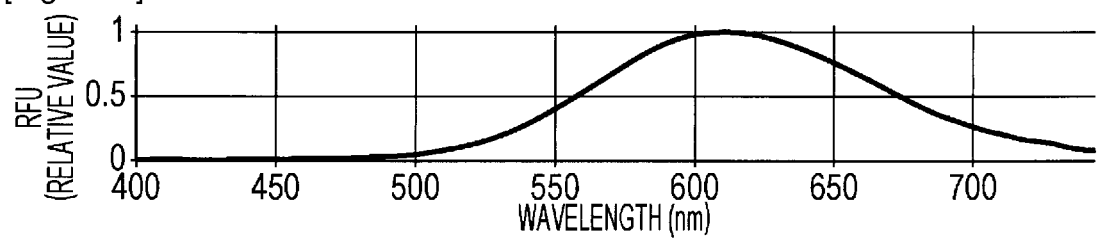
[Fig. 43A]
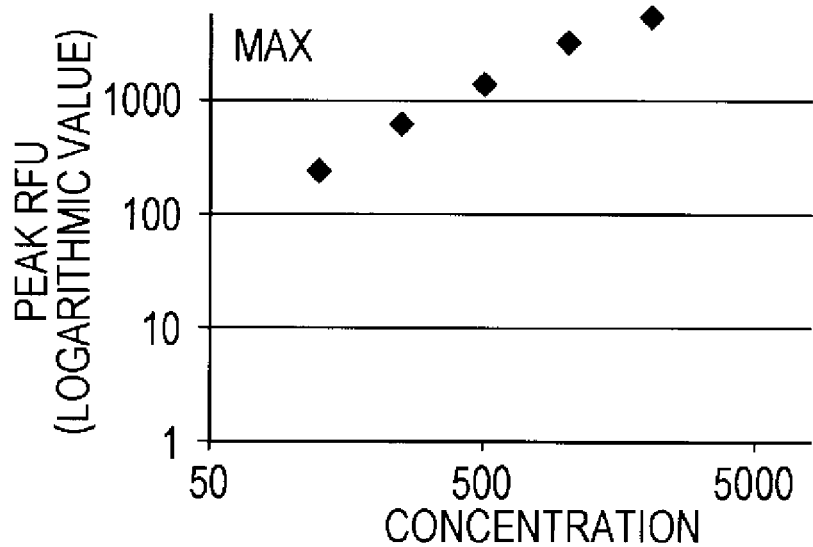

[Fig. 43B]
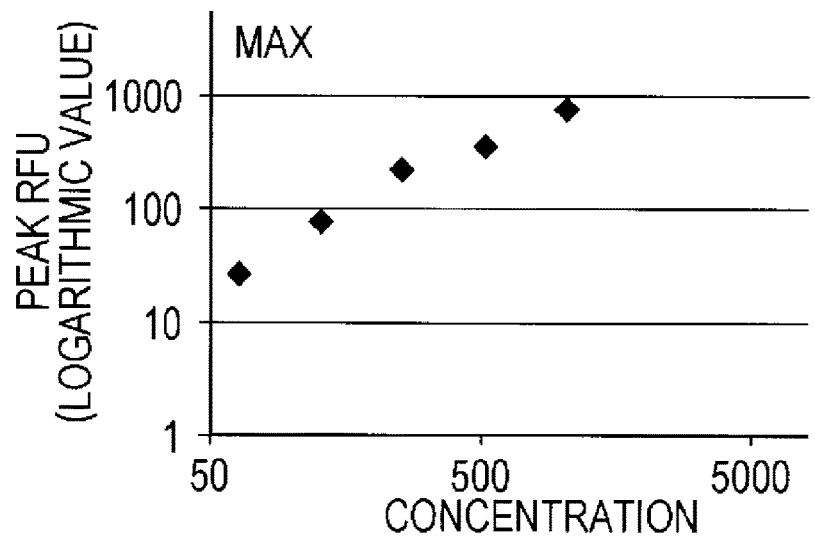
[Fig. 43C]
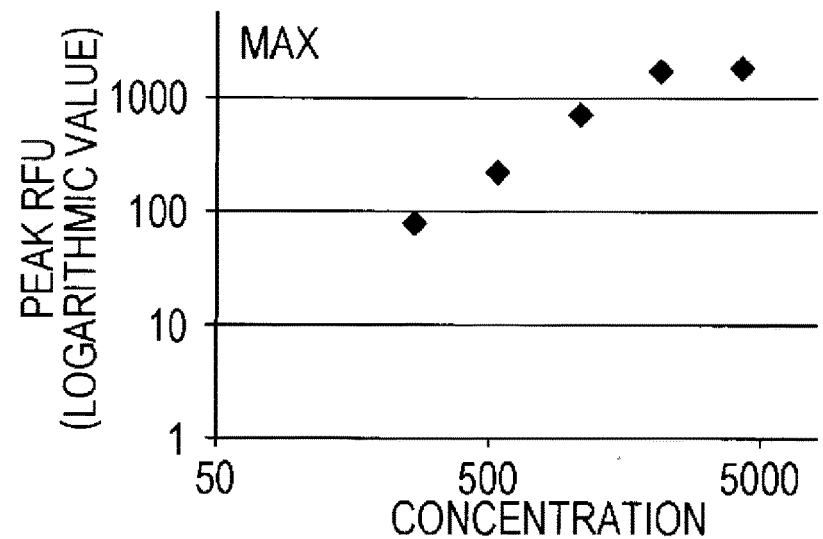
[Fig. 43D]
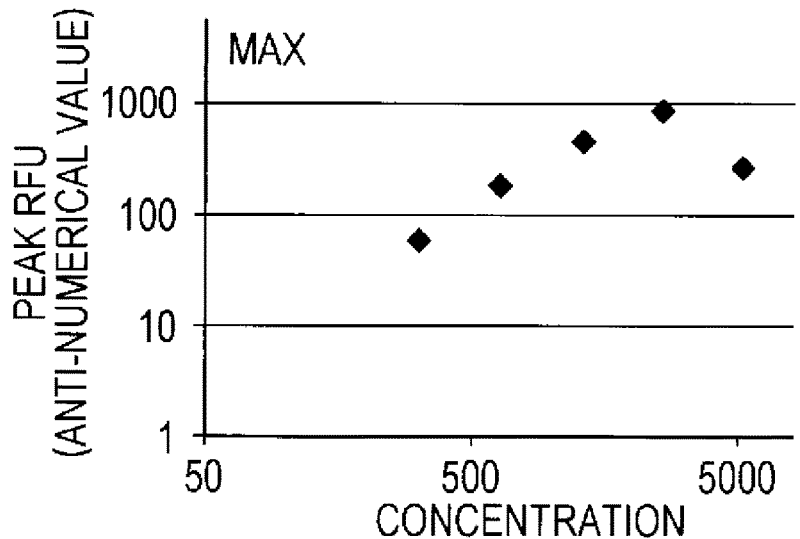

[Fig. 43E]
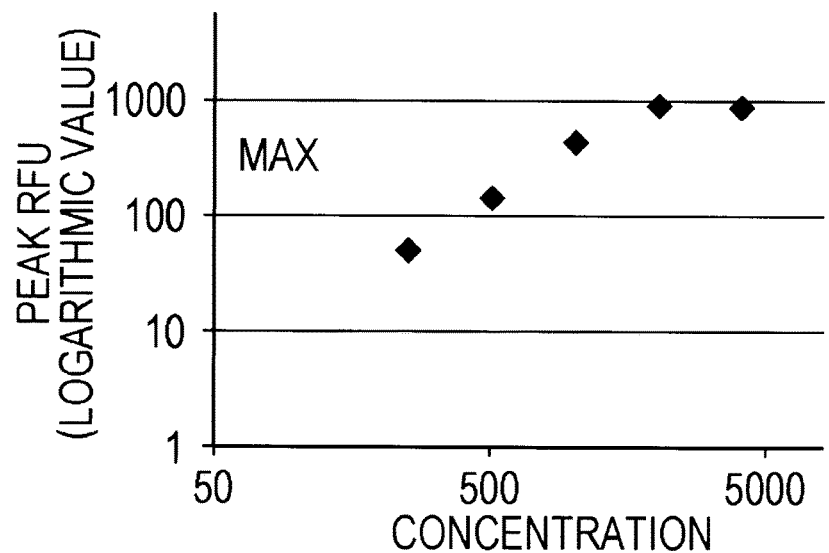
[Fig. 43F]
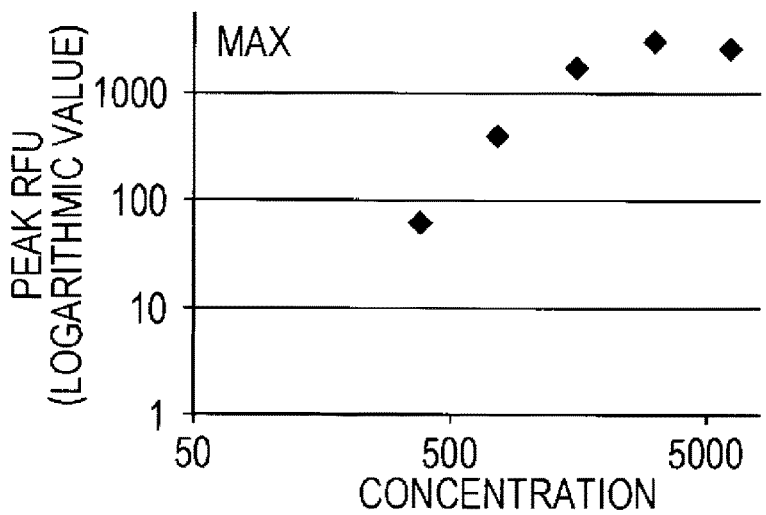
[Fig. 43G]
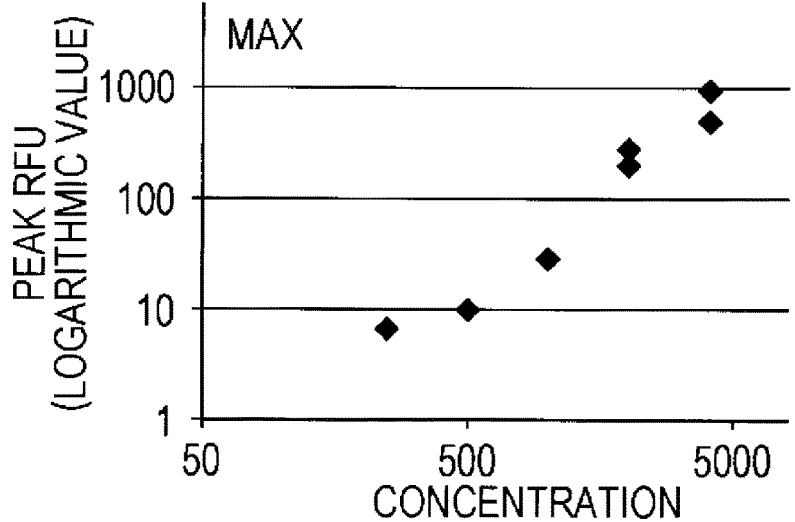

[Fig. 44A]
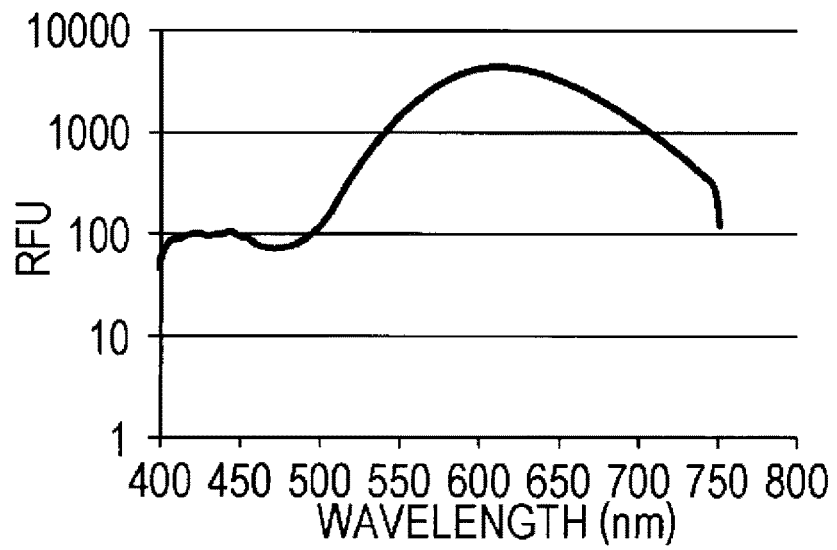
[Fig. 44B]
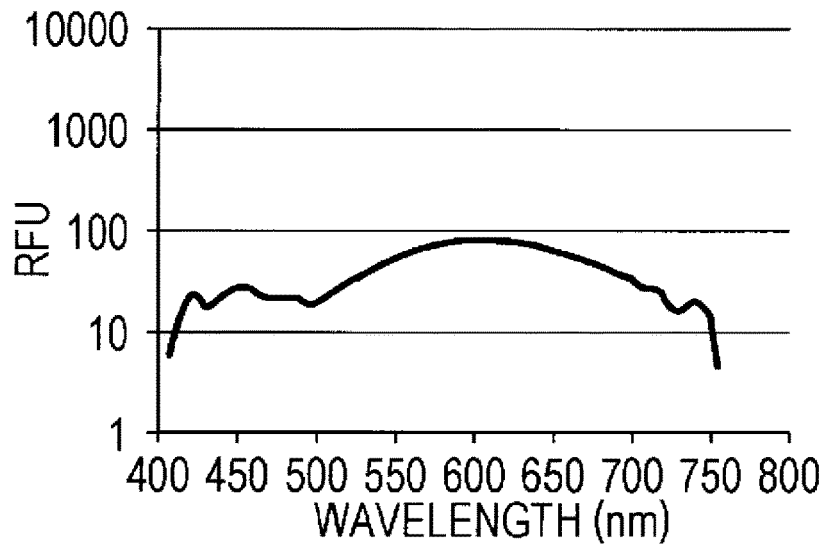
[Fig. 44C]
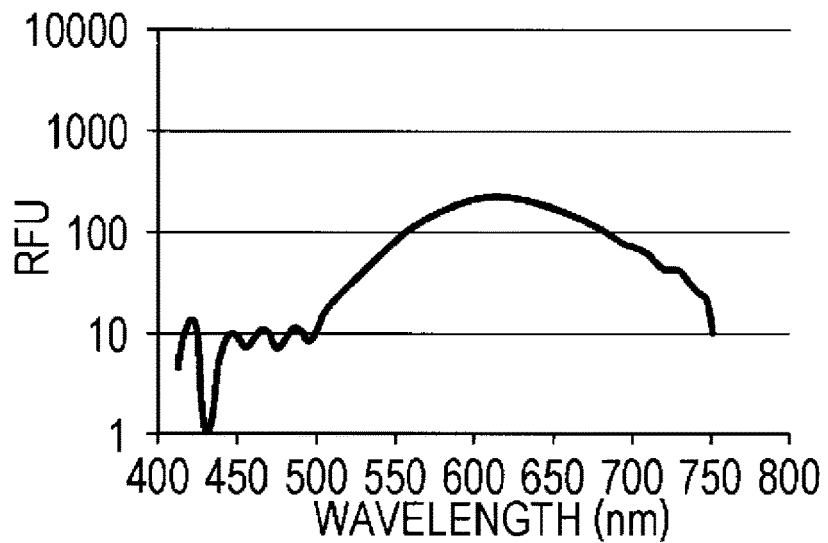

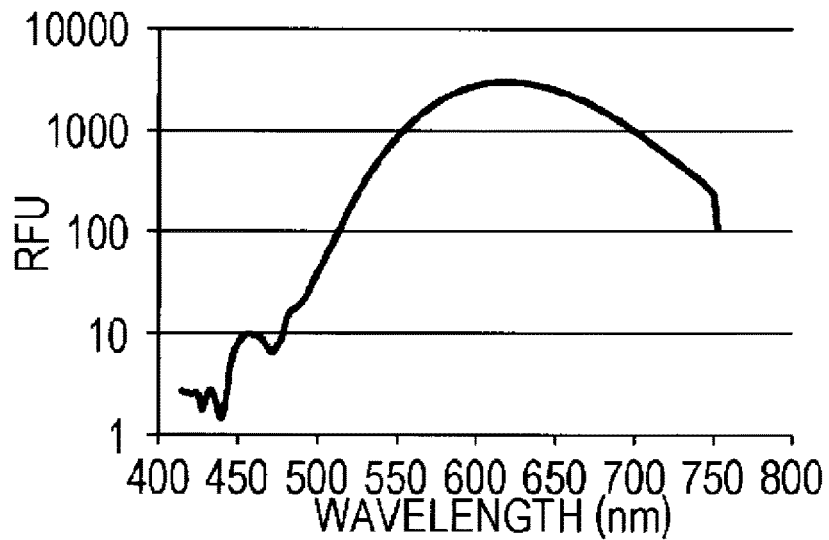
[Fig. 44D]
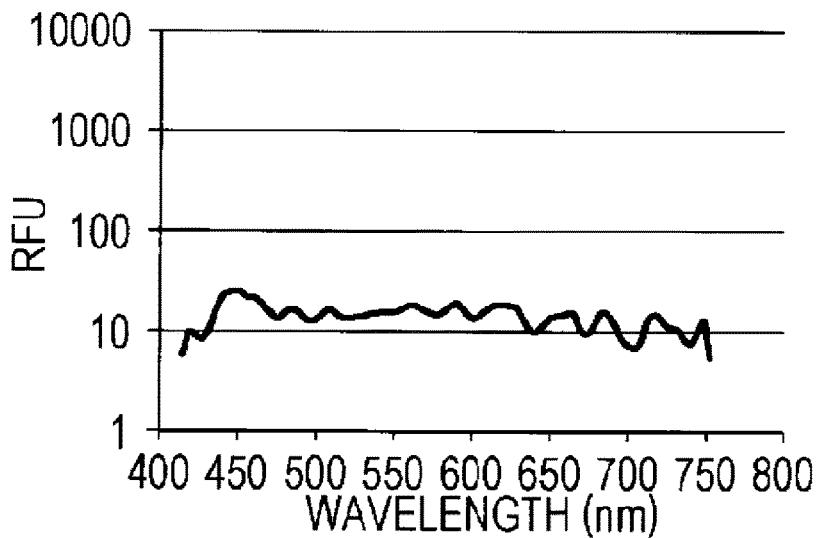
[Fig. 44E]
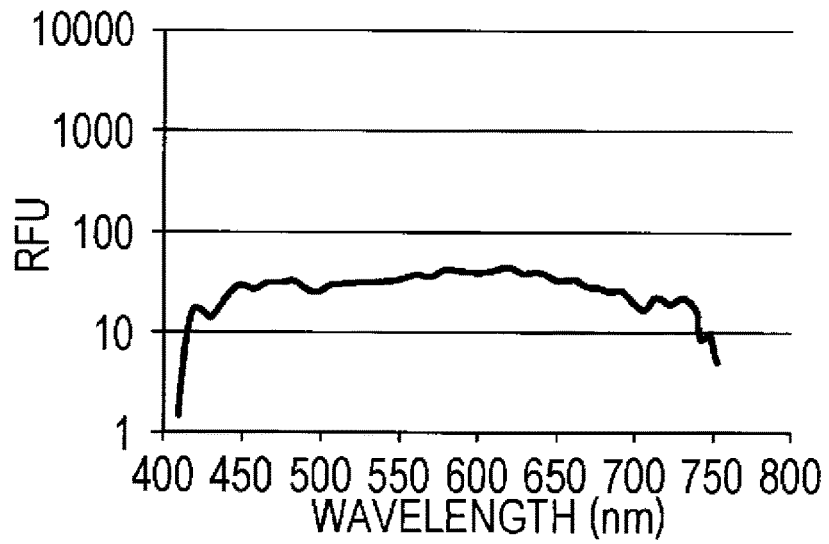
[Fig. 44F]

[Fig. 44G]
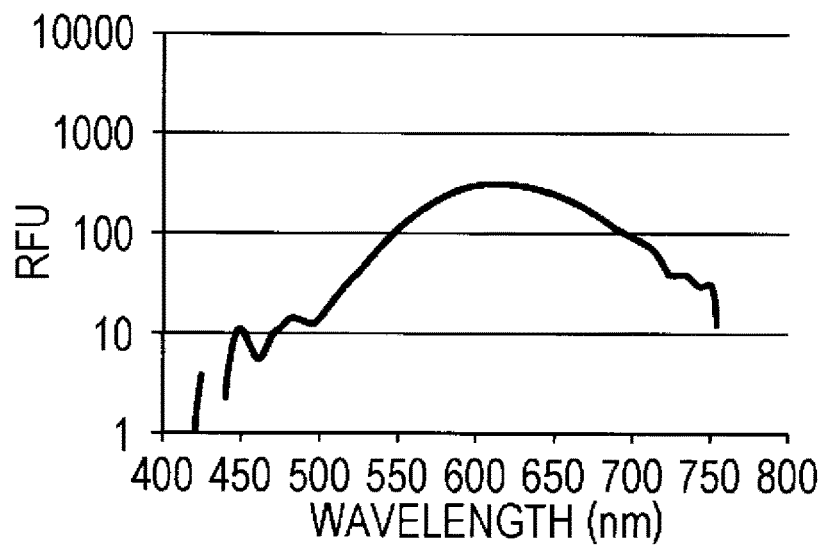
[Fig. 44H]
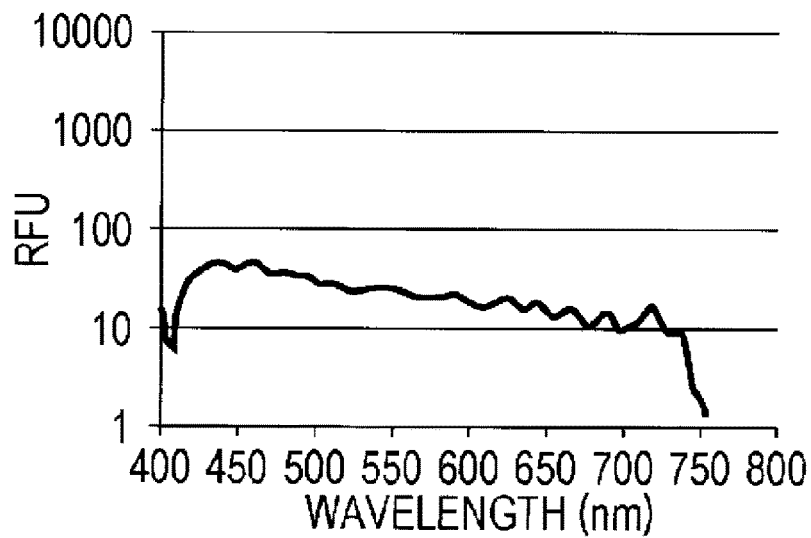
[Fig. 45A]
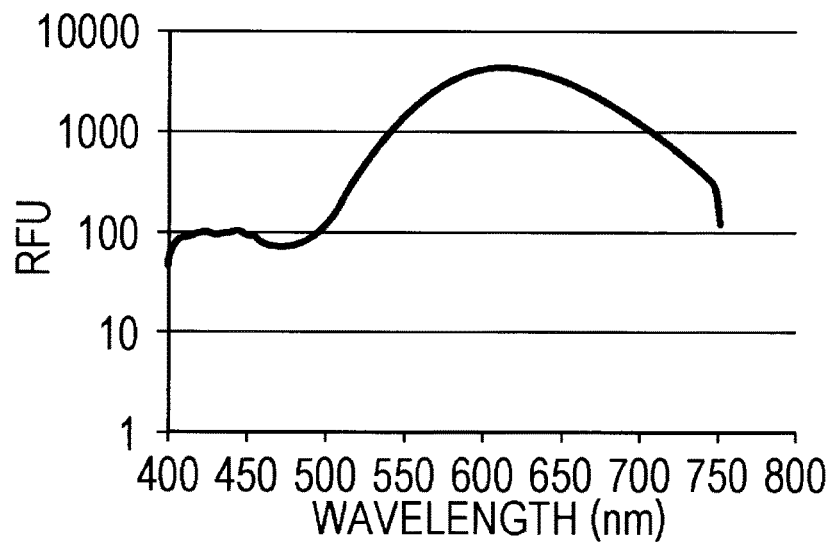

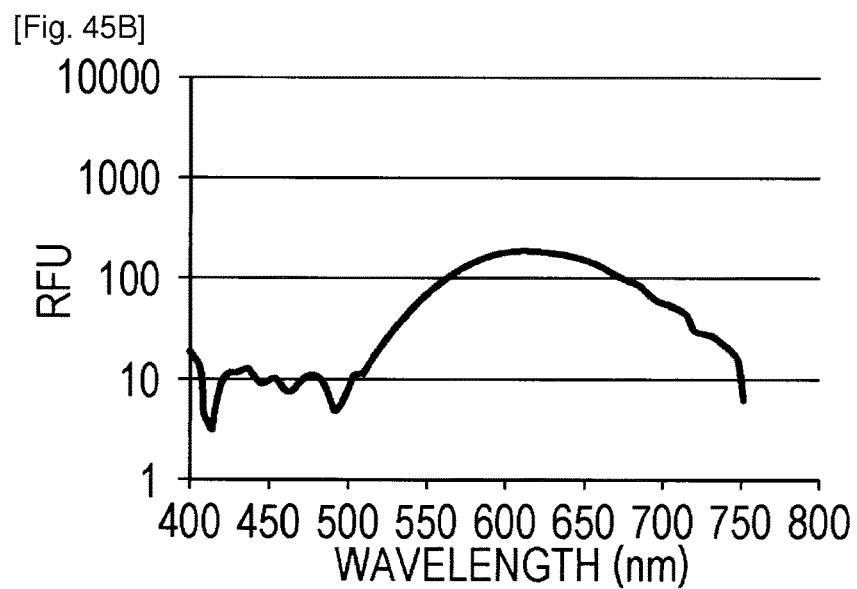
[Fig. 45B]
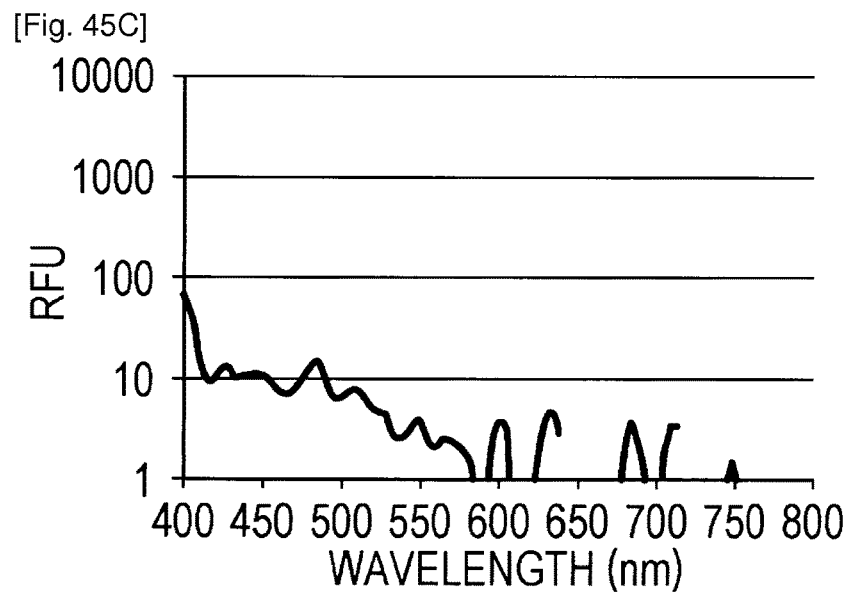
[Fig. 45C]
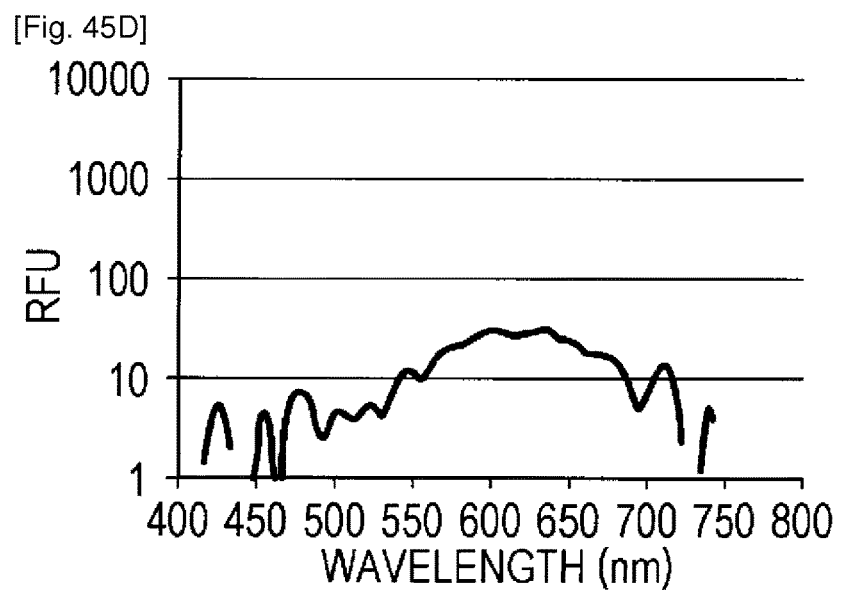
[Fig. 45D]

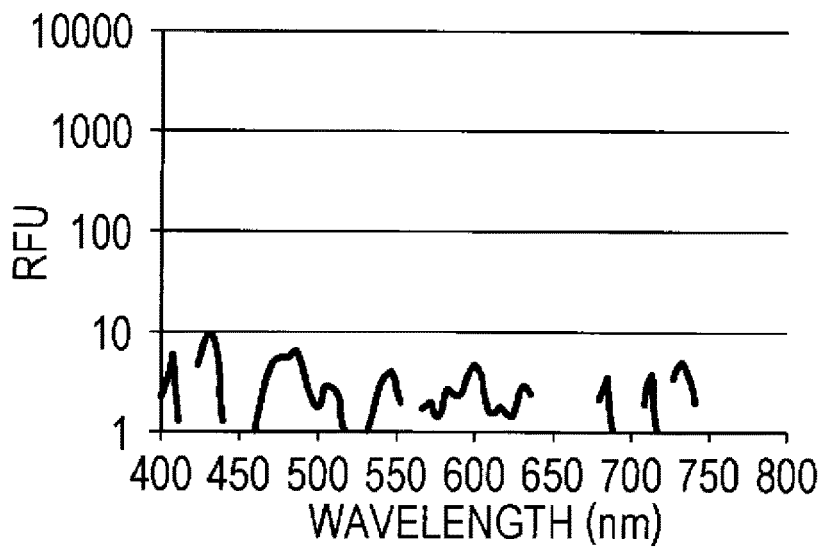
[Fig. 45E]
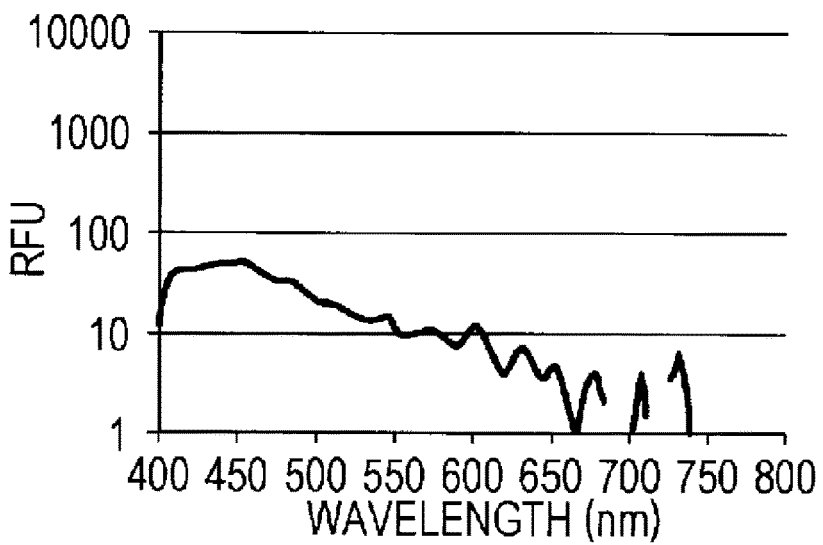
[Fig. 45F]
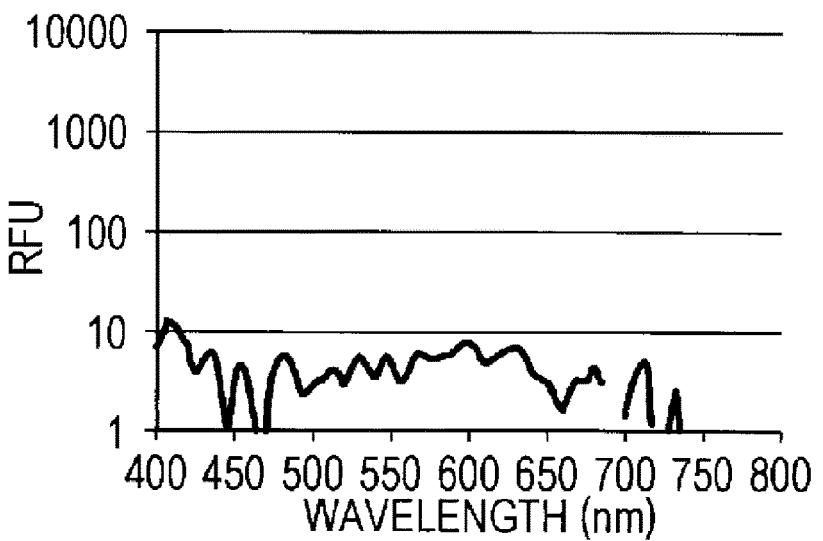
[Fig. 45G]

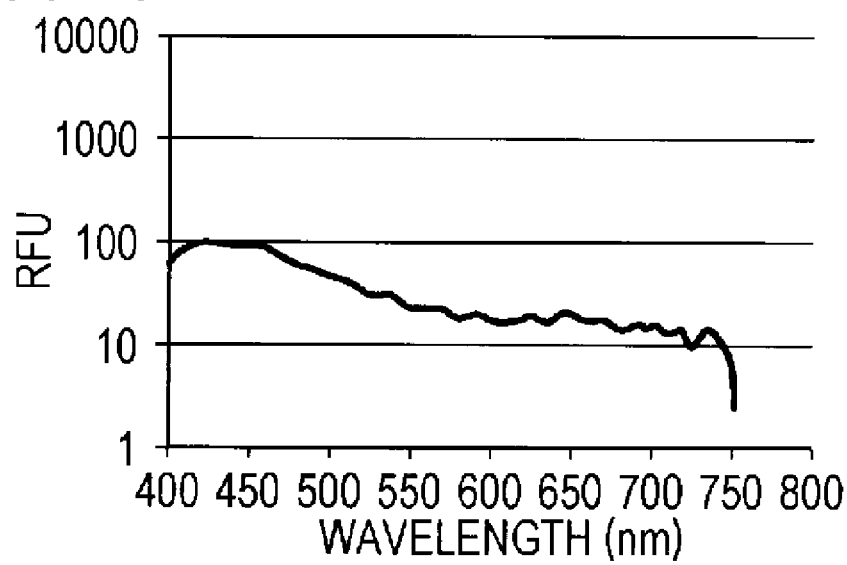
[Fig. 45H]
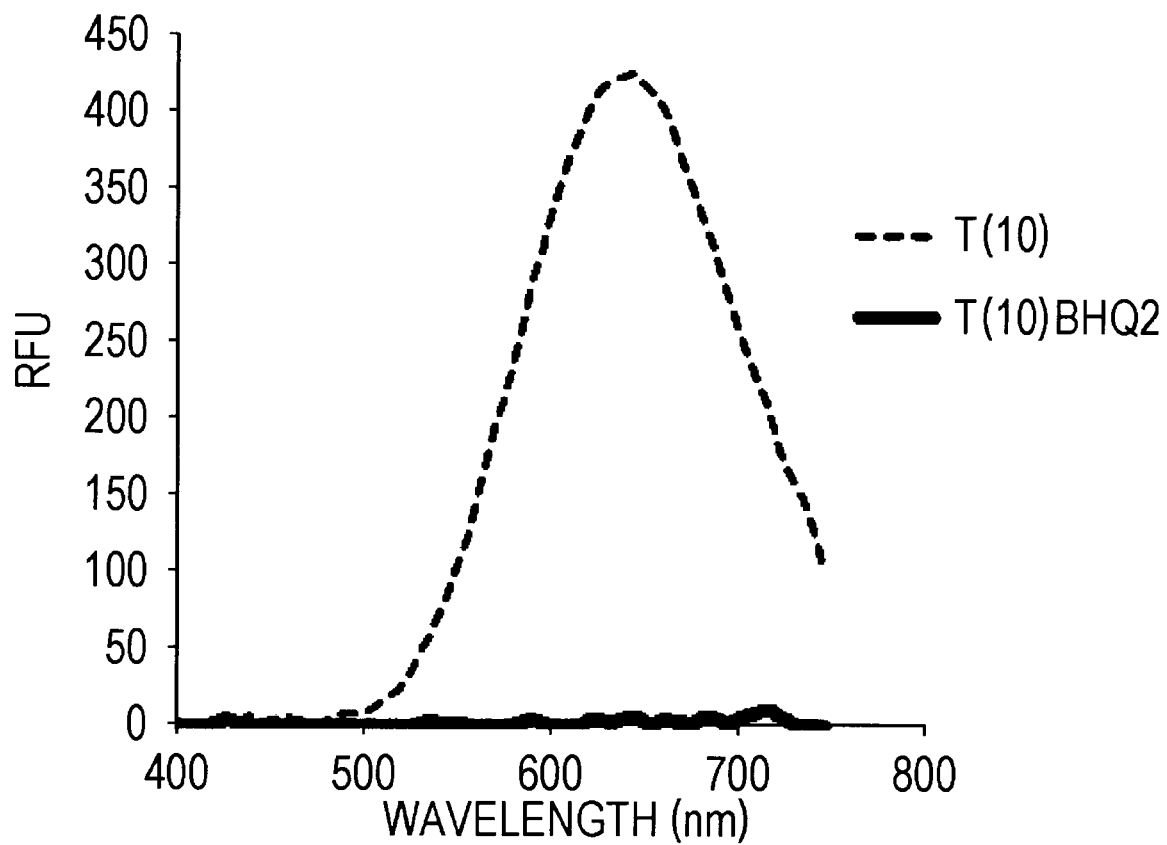
[Fig. 46]

[Fig. 47A]
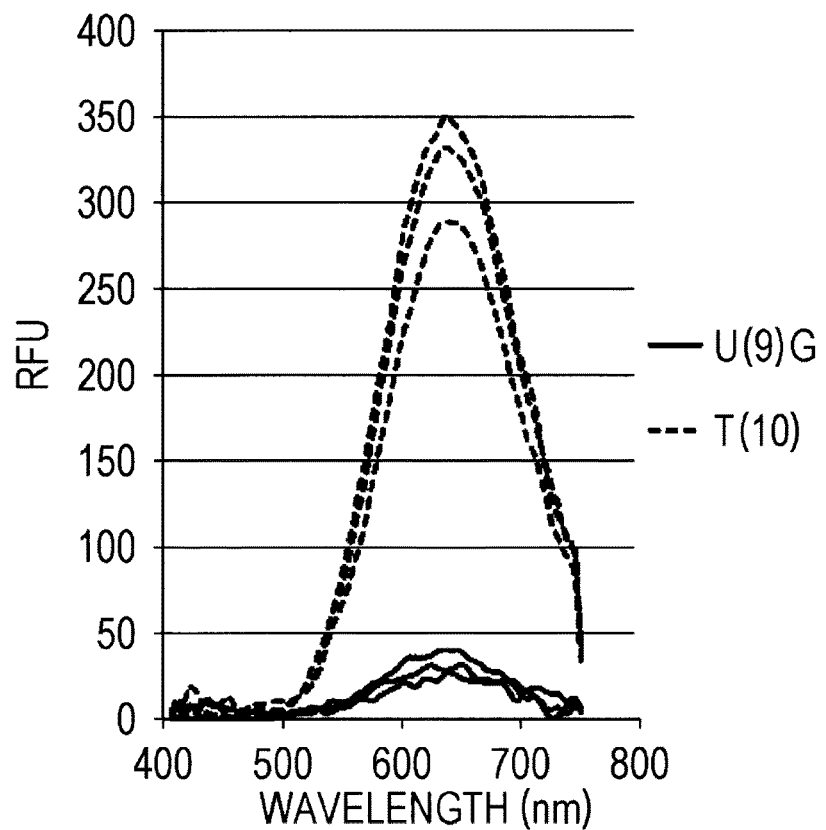
[Fig. 47B]
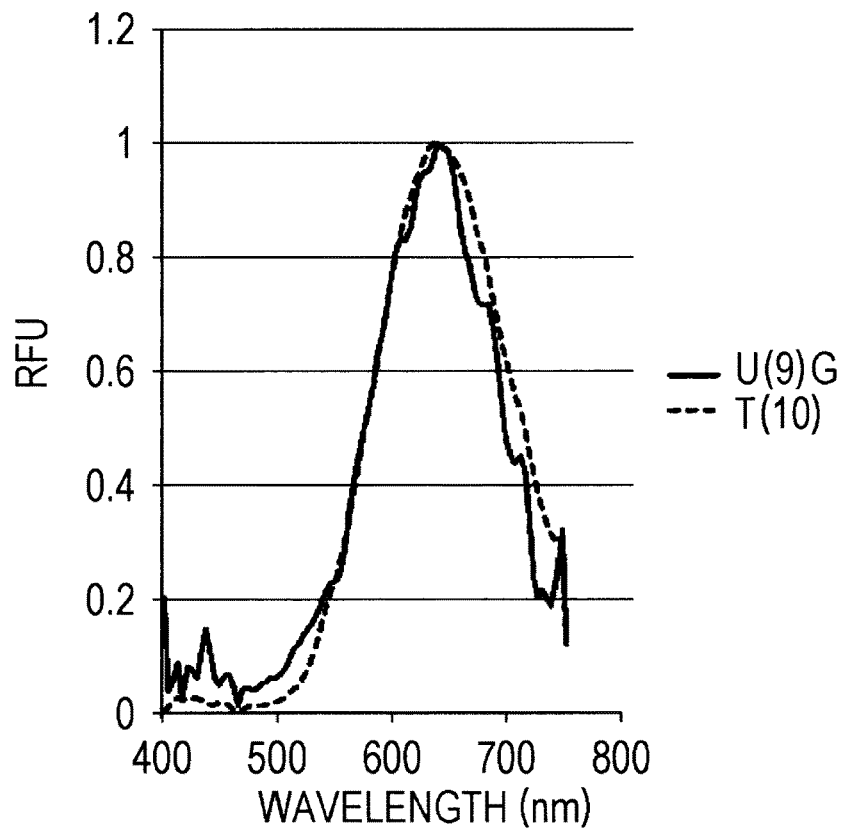

[Fig. 48]
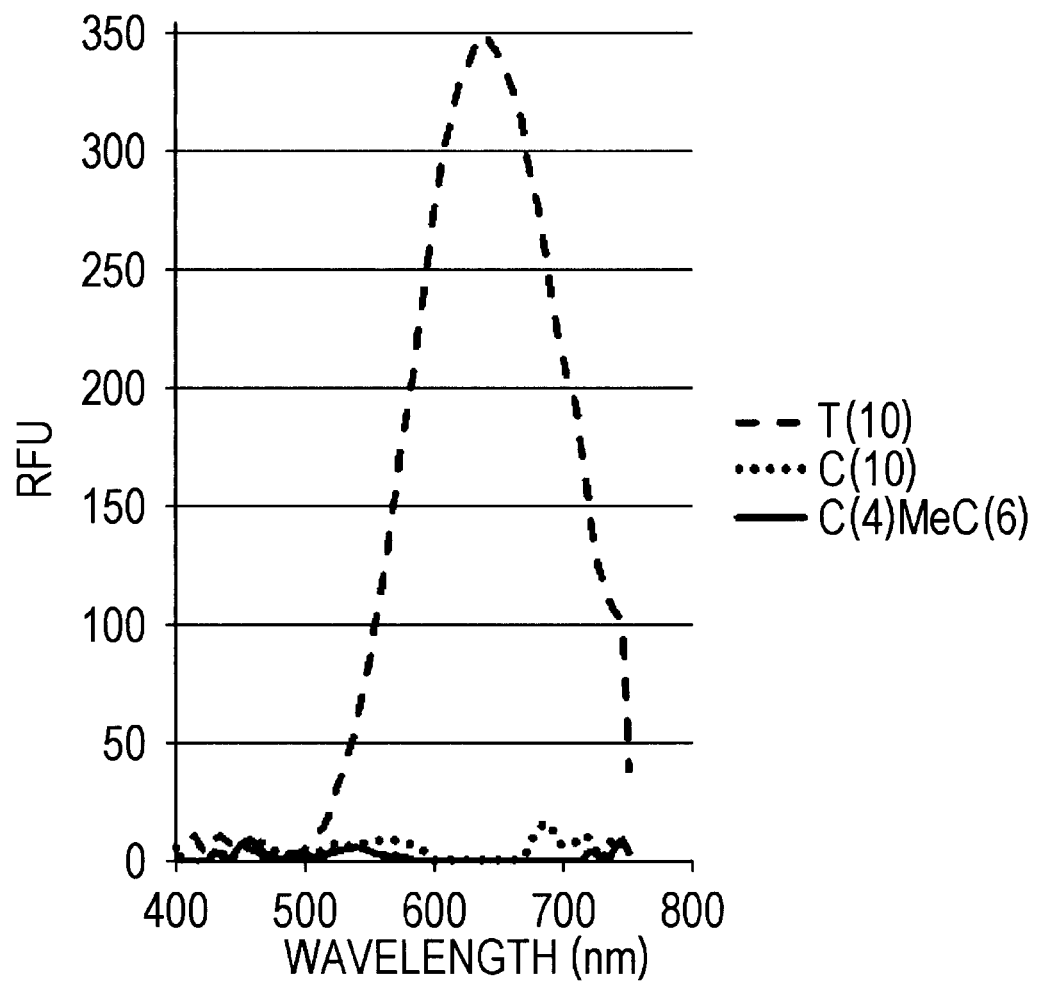

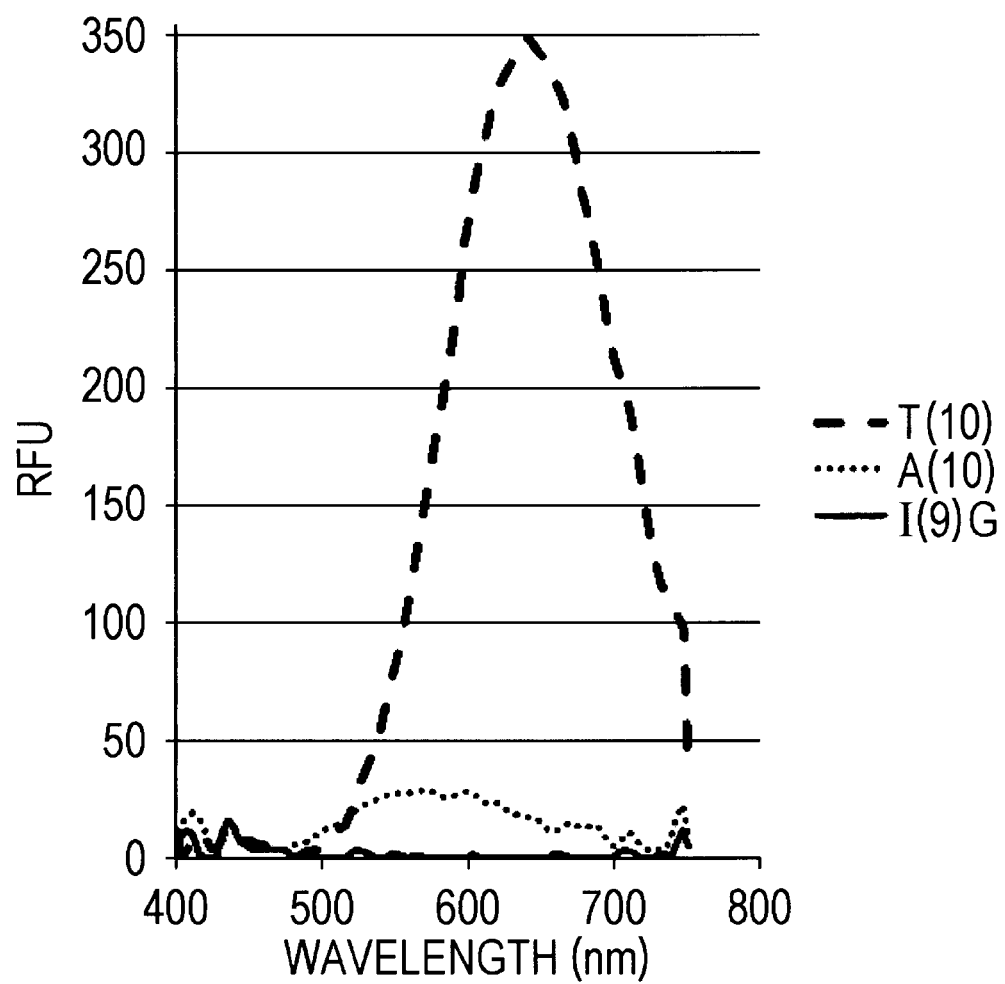
[Fig. 49]

SEQUENCE LISTING

```
<160> NUMBER OF SEQ ID NOS: 33

<210> SEQ ID NO 1
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 1
aaaaaaaaaa aaaaaaaaaa                                                   20

<210> SEQ ID NO 2
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 2
tttttttttt tttttttttt                                                   20

<210> SEQ ID NO 3
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 3
gggggggggg gggggggggg                                                   20

<210> SEQ ID NO 4
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 4
cccccccccc cccccccccc                                                   20

<210> SEQ ID NO 5
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 5
aaaaaataaa taataaaaaa                                                   20

<210> SEQ ID NO 6
<211> LENGTH: 20
<212> TYPE: DNA
```

```
<213> ORGANISM: Artificial Sequence
<220> FEATURE:
<223> OTHER INFORMATION: synthesized oligo-DNA

<400> SEQUENCE: 6 tttttttatta tttatttttt                                              20

<210> SEQ ID NO 7
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 7 gggggggcggg cggcgggggg                                              20

<210> SEQ ID NO 8
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 8
ccccccgccg cccgcccccc                                               20

<210> SEQ ID NO 9
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 9 aaaattttttt ttttttaaaa                                              20

<210> SEQ ID NO 10
<211> LENGTH: 6
<212> TYPE: DNA
<213> ORGANISM: Artificial Sequence
<220> FEATURE:
<223> OTHER INFORMATION: synthesized oligo-DNA

<400> SEQUENCE: 10 tttttt                                                               6

<210> SEQ ID NO 11
<211> LENGTH: 3
<212> TYPE: DNA
<213> ORGANISM: Artificial Sequence
<220> FEATURE:
<223> OTHER INFORMATION: synthesized oligo-DNA

<400> SEQUENCE: 11 aaa                                                                  3

<210> SEQ ID NO 12
<211> LENGTH: 3
<212> TYPE: DNA
<213> ORGANISM: Artificial Sequence
<220> FEATURE:
<223> OTHER INFORMATION: synthesized oligo-DNA

<400> SEQUENCE: 12 ttt                                                                  3
```

<210> SEQ ID NO 13
<211> LENGTH: 3
<212> TYPE: DNA
<213> ORGANISM: Artificial Sequence
<220> FEATURE:
<223> OTHER INFORMATION: synthesized oligo-DNA

<400> SEQUENCE: 13 tta                                                                         3

<210> SEQ ID NO 14
<211> LENGTH: 3
<212> TYPE: DNA
<213> ORGANISM: Artificial Sequence
<220> FEATURE:
<223> OTHER INFORMATION: synthesized oligo-DNA

<400> SEQUENCE: 14 tat                                                                         3

<210> SEQ ID NO 15
<211> LENGTH: 3
<212> TYPE: DNA
<213> ORGANISM: Artificial Sequence
<220> FEATURE:
<223> OTHER INFORMATION: synthesized oligo-DNA

<400> SEQUENCE: 15 att                                                                         3

<210> SEQ ID NO 16
<211> LENGTH: 3
<212> TYPE: DNA
<213> ORGANISM: Artificial Sequence
<220> FEATURE:
<223> OTHER INFORMATION: oligo-DNA

<400> SEQUENCE: 16 taa                                                                         3

<210> SEQ ID NO 17
<211> LENGTH: 3
<212> TYPE: DNA
<213> ORGANISM: Artificial Sequence
<220> FEATURE:
<223> OTHER INFORMATION: synthesized oligo-DNA

<400> SEQUENCE: 17 ata                                                                         3

<210> SEQ ID NO 18
<211> LENGTH: 3
<212> TYPE: DNA
<213> ORGANISM: Artificial Sequence
<220> FEATURE:
<223> OTHER INFORMATION: synthesized oligo-DNA

<400> SEQUENCE: 18 aat                                                                         3

<210> SEQ ID NO 19
<211> LENGTH: 10
<212> TYPE: DNA
<213> ORGANISM: Artificial Sequence
<220> FEATURE:

<223> OTHER INFORMATION: synthesized oligo-DNA

<400> SEQUENCE: 19
tttttttttt                                                          10

<210> SEQ ID NO 20
<211> LENGTH: 10
<212> TYPE: DNA
<213> ORGANISM: Artificial Sequence
<220> FEATURE:
<223> OTHER INFORMATION: synthesized oligo-DNA

<400> SEQUENCE: 20
uuuuuuuuug                                                          10

<210> SEQ ID NO 21
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 21
cccctttttt tttttccccc                                               20

<210> SEQ ID NO 22
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 22 ccccccccctt tttttttttt                                              20

<210> SEQ ID NO 23
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 23
tttttttttt ttcccccccc                                               20

<210> SEQ ID NO 24
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 24
ccttttttcc ccttttttcc                                               20

<210> SEQ ID NO 25
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 25
ctttcctttc ctttcctttc                                               20

```
<210> SEQ ID NO 26
<211> LENGTH: 20
<212> TYPE: DNA
<213> ORGANISM: Artificial Sequence
<220> FEATURE:
<223> OTHER INFORMATION: synthesized oligo-DNA

<400> SEQUENCE: 26
ccttcttctt cttcttcttc                                                    20

<210> SEQ ID NO 27
<211> LENGTH: 5
<212> TYPE: DNA
<213> ORGANISM: Artificial Sequence
<220> FEATURE:
<223> OTHER INFORMATION: synthesized oligo-DNA

<400> SEQUENCE: 27 ttttt                                                                     5

<210> SEQ ID NO 28
<211> LENGTH: 4
<212> TYPE: DNA
<213> ORGANISM: Artificial Sequence
<220> FEATURE:
<223> OTHER INFORMATION: synthesized oligo-DNA

<400> SEQUENCE: 28 tttt                                                                      4

<210> SEQ ID NO 29
<211> LENGTH: 2
<212> TYPE: DNA
<213> ORGANISM: Artificial Sequence
<220> FEATURE:
<223> OTHER INFORMATION: synthesized oligo-DNA

<400> SEQUENCE: 29 tt                                                                        2

<210> SEQ ID NO 30
<211> LENGTH: 10
<212> TYPE: DNA
<213> ORGANISM: Artificial Sequence
<220> FEATURE:
<223> OTHER INFORMATION: synthesized oligo-DNA

<400> SEQUENCE: 30
aaaaaaaaaa                                                               10

<210> SEQ ID NO 31
<211> LENGTH: 10
<212> TYPE: DNA
<213> ORGANISM: Artificial Sequence
<220> FEATURE:
<223> OTHER INFORMATION: synthesized oligo-DNA
<220> FEATURE:
<221> NAME/KEY: misc_feature
<222> LOCATION: (1)..(9)
<223> OTHER INFORMATION: n is i

<400> SEQUENCE: 31 nnnnnnnnng                                                               10

<210> SEQ ID NO 32
<211> LENGTH: 10
<212> TYPE: DNA
```

```
<213> ORGANISM: Artificial Sequence
<220> FEATURE:
<223> OTHER INFORMATION: synthesized oligo-DNA

<400> SEQUENCE: 32
cccccccccc                                                                       10

<210> SEQ ID NO 33
<211> LENGTH: 10
<212> TYPE: DNA
<213> ORGANISM: Artificial Sequence
<220> FEATURE:
<223> OTHER INFORMATION: synthesized oligo-DNA
<220> FEATURE:
<221> NAME/KEY: misc_feature
<222> LOCATION: (3)..(8)
<223> OTHER INFORMATION: n is 5-Methyl-2-deoxycytidine

<400> SEQUENCE: 33 ccnnnnnncc                                                                       10
```

MICROCHIP FOR NUCLEIC ACID ANALYSIS

CROSS REFERENCES TO RELATED APPLICATIONS

The present application is a national stage of International Application No. PCT/JP2013/002906 filed on May 1, 2013 and claims priority to Japanese Patent Application No. 2012-108719 filed on May 10, 2012, the disclosure of which is incorporated herein by reference.

BACKGROUND

The present disclosure relates to a microchip for nucleic acid analysis and more specifically to a microchip for nucleic acid analysis, in which nucleic acids are optically analyzed in a region disposed in the microchip.

In recent years, microchips for nucleic acid analysis have begun to be used in various fields such as the medical field, the drug discovery field, the clinical examination field, the food field, the agricultural field, the engineering field, the medicolegal field, and the criminal identification field. The microchips for nucleic acid analysis include a region (well) disposed therein, in which nucleic acids and, according to demand, a reagent are introduced to cause amplification reaction, electrophoresis, hybridization, staining, detection, and the like.

For example, Patent Literature 1 discloses a microchip for nucleic acid amplification reaction including an inlet disposed to introduce a liquid, a plurality of wells therein to serve as reaction fields of nucleic acid amplification reaction, and a flow passage disposed to supply the liquid to each of the wells from the inlet. The microchip for nucleic acid amplification reaction contains substances such as a reagent and the like which are desired for reaction and which are previously fixed in each of the wells so as to permit simple analysis without the labor of introducing the substances into each of the wells. Patent Literature 2 discloses, as related art, a technique of covering a substance fixed in a well with a thin film which is melted near a reaction temperature of nucleic acid amplification reaction.

A method of staining nucleic acids with fluorescent dyes is used as a basic technique for detecting nucleic acids. As the fluorescent dyes, ethidium bromide, SYBR green, and the like are commonly used. For example, ethidium bromide is frequently used for staining nucleic acids in electrophoresis. In addition, SYBR green is used for detecting in real-time an amplification process of nucleic acids in nucleic acid amplification reaction such as polymerase chain reaction.

In connection with this technique, fluorescence generally referred to as autofluorescence shown by cells during fluorescence observation is described. One of the fluorescence is orange autofluorescence shown by cells irradiated with UV in the presence of copper. For example, it has been reported that cells in a specified portion of the larval midgut of fruit fly emit orange fluorescence when administrated with copper (refer to Non-Patent Literatures 1 to 8). The cells with which particularly strong orange fluorescence is observed in the larval midgut of fruit fly are referred to as "copper cells" or the like. Also, it has been reported that when the concentration of copper to be administered is increased, fluorescence is also observed in cells (Non-Patent Literature 4) around the copper cells and the whole body walls of larvae (Non-Patent Literature 2).

It is described that the orange fluorescence is observed in both the cytoplasm and the nuclei in cells, and particularly the orange fluorescence is significantly detected in cytoplasm granules (refer to Non-Patent Literatures 2 to 4 and 7). It is also described that a wavelength region of the fluorescence is 590 to 630 nm, a peak wavelength is 610 nm, and a maximum excitation wavelength is 340 nm (Non-Patent Literature 3).

In addition, autofluorescence having the same properties is observed in species other than fruit flies. For example, it has been reported that in an experiment with rats, orange fluorescence (peak wavelength 605 nm) is observed by UV excitation (excitation wavelength 310 nm) in the livers of individuals supplied with copper (refer to Non-Patent Literature 9). Further, it has been reported that similar fluorescence is observed in kidneys of model rats in which copper accumulates in the kidneys and livers with aging (refer to Non-Patent Literature 10). Autofluorescence having the same properties has been reported in yeasts (refer to Non-Patent Literature 11) and human hepatocytes of patients with Wilson's disease (refer to Non-Patent Literature 12). The Wilson's disease is a genetic disease that copper accumulates in hepatocytes due to a failure of the copper excretory function.

As a fluorescent material which emits the orange fluorescence, a complex (abbreviated as "Cu-MT" hereinafter) of copper with metallothionein (MT) is estimated (refer to Non-Patent Literatures 14 to 23). With respect to wavelength properties of the Cu-MT, Non-Patent Literature 13 describes an excitation wavelength of 305 nm and a fluorescence wavelength of 565 nm, and Non-Patent Literature 17 describes an excitation wavelength of 310 nm and a fluorescence wavelength of 570 nm. In addition, it is considered that copper is present in the state of monovalent ion (Cu(I)) in the Cu-MT (refer to Non-Patent Literatures 13, 15, 17, 19, and 23).

Compounds containing pyrimidine or mercaptide and emitting fluorescence by the action of pyrimidine or mercaptide with copper are widely reported as the fluorescent material containing copper (refer to Non-Patent Literatures 24 to 29).

On the other hand, interaction of nucleic acids with various metal ions has been researched from long ago. For example, with respect to interaction of nucleic acids with copper monovalent ion, it is common knowledge that copper contained in a small amount in cell nuclei stabilizes a nucleic acid structure but damages DNA in coexistence with hydrogen peroxide (refer to Non-Patent Literature 30). Also, it has been reported that absorption spectra of DNA are changed by interaction with copper (refer to Non-Patent Literatures 30 and 31). Further, it has been reported that changes in absorption spectra depend on DNA base sequences (specifically a polymer containing a GC pair and a polymer containing an AT pair) (refer to Non-Patent Literature 30).

CITATION LIST

Patent Literature

PTL 1: Japanese Unexamined Patent Application Publication No. 2011-160728
PTL 2: Japanese Unexamined Patent Application Publication No. 2012-024072

Non Patent Literature

NPL 1: Physiological genetic studies on copper metabolism in the genus *Drosophila* (1950) Genetics 35, 684-685

NPL 2: Organization and function of the inorganic constituents of nuclei (1952) Exp. Cell Res., Suppl. 2:161-179

NPL 3: Ultrastructure of the copper-accumulating region of the Drosophila larval midgut (1971) Tissue Cell. 3, 77-102

NPL 4: Specification of a single cell type by a Drosophila homeotic gene (1994) Cell. 76, 689-702

NPL 5: Two different thresholds of wingless signaling with distinct developmental consequences in the Drosophila midgut (1995) EMBO J. 14, 5016-5026

NPL 6: Calcium-activated potassium channel gene expression in the midgut of Drosophila (1997) Comp. Biochem. Physiol. B Biochem. Mol. Biol. 118, 411-420

NPL 7: Evidence that a copper-metallothionein complex is responsible for fluorescence in acid-secreting cells of the Drosophila stomach (2001) Cell Tissue Res. 304, 383-389

NPL 8: Peptidergic paracrine and endocrine cells in the midgut of the fruit fly maggot (2009) Cell Tissue Res. 336, 309-323

NPL 9: A luminescence probe for metallothionein in liver tissue: emission intensity measured directly from copper metallothionein induced in rat liver (1989) FEBS Lett. 257, 283-286

NPL 10: Direct visualization of copper-metallothionein in LEC rat kidneys: application of autofluorescence signal of copper-thiolate cluster (1996) J. Histochem. Cytochem. 44, 865-873

NPL 11: Incorporation of copper into the yeast Saccharomyces cerevisiae. Identification of Cu (I)-metallothionein in intact yeast cells (1997) J. Inorg. Biochem. 66, 231-240

NPL 12: Portmann B. Image of the month. Copper-metallothionein autofluorescence (2009) Hepatology. 50, 1312-1313

NPL 13: Luminescence properties of Neurospora copper metallothionein (1981) FEBS Lett. 127, 201-203

NPL 14: Copper transfer between Neurospora copper metallothionein and type 3 copper apoproteins (1982) FEBS Lett. 142, 219-222

NPL 15: Spectroscopic studies on Neurospora copper metallothionein (1983) Biochemistry, 22, 2043-2048

NPL 16: Metal substitution of Neurospora copper metallothionein (1984) Biochemistry, 23, 3422-3427

NPL 17: (Cu, Zn)-metallothioneins from fetal bovine liver chemical and spectroscopic properties (1985) J. Biol. Chem. 260, 10032-10038

NPL 18: Primary structure and spectroscopic studies of Neurospora copper metallothionein (1986) Environ. Health Perspect. 65, 21-27

NPL 19: Characterization of the copper-thiolate cluster in yeast metallothionein and two truncated mutants (1988) J. Biol. Chem. 263, 6688-6694

NPL 20: Luminescence emission from Neurospora copper metallothionein. Timeresolved studies (1989) Biochem. J. 260, 189-193

NPL 21: Establishment of the metal-to-cysteine connectivities in silver-substituted yeast metallothionein (1991) J. Am. Chem. Soc. 113, 9354-9358

NPL 22: Copper- and silver-substituted yeast metallothioneins: Sequential proton NMR assignments reflecting conformational heterogeneity at the C terminus (1993) Biochemistry, 32, 6773-6787

NPL 23: Luminescence decay from copper (I) complexes of metallothionein (1998) Inorg. Chim. Acta. 153, 115-118

NPL 24: Solution Luminescence of Metal Complexes (1970) Appl. Spectrosc. 24, 319-326

NPL 25: Fluorescence of Cu, Au and Ag mercaptides (1971) Photochem. Photobiol. 13, 279-281

NPL 26: Luminescence of the copper-carbon monoxide complex of Neurospora tyrosinase (1980) FEBS Lett. 111, 232-234

NPL 27: Luminescence of carbon monoxide hemocyanins (1980) Proc. Natl. Acad. Sci. U.S.A. 77, 2387-2389

NPL 28: Photophysical properties of hexanuclear copper (I) and silver (I) clusters (1992) Inorg. Chem., 31, 1941-1945

NPL 29: Photochemical and photophysical properties of tetranuclear and hexanuclear clusters of metals with d10 and s2 electronic configurations (1993) Acc. Chem. Res. 26, 220-226

NPL 30: Interaction of copper (I) with nucleic acids (1990) Int. J. Radiat. Biol. 58, 215-234

NPL 31: Copper (I)-Catalyzed Regioselective "Ligation" of Azides and Terminal Alkynes (2002) Ang. Chem. Int. Ed. 41, 2596-2599

SUMMARY

Technical Problem

When fluorescence of nucleic acids is detected using existing fluorescent dyes in a region disposed in a microchip for nucleic acid analysis, there is the following problem. That is, since fluorescent dyes are liquid reagents, a chip structure for holding the fluorescent dyes in the region is complicated, thereby complicating an operation using the chip. In general, temperature control and light shielding are desired for preventing deterioration of liquid reagents during storage, and the liquid reagents can be stored for short periods of time, thereby causing a limitation of storage conditions for a microchip for nucleic acid analysis which holds usual fluorescent dyes in a region.

Accordingly, it is desirable to provide a microchip for nucleic acid analysis which can be used by a simple operation and which can exhibit stable performance even after long-term storage.

Solution to Problem

In order to resolve the above-described problem, the present disclosure provides a microchip for nucleic acid analysis including a reaction region and a detection region, the detection region containing copper.

In the microchip for nucleic acid analysis, the copper may be solid copper and can be sputtered, vapor-deposited, or applied to the detection region.

In the microchip for nucleic acid analysis, nucleic acids can be optically analyzed by detecting fluorescence emitted from the nucleic acids which form complexes by contact with copper.

In the microchip for nucleic acid analysis, the detection region contains a salt such as sodium chloride or potassium chloride according to demand. The amount of the salt contained is preferably determined to a final concentration of 50 mM or more after a sample solution containing nucleic acids is introduced into the detection region.

In the microchip for nucleic acid analysis, the reaction region may serve as a reaction field of amplification reaction, electrophoresis, hybridization reaction, or bisulfite reaction of the nucleic acids. In addition, the microchip for nucleic acid analysis can have an inlet portion through which the sample solution is introduced into the reaction region, and a flow passage which connects the reaction region to the detection region.

In the present disclosure, the nucleic acids include natural nucleic acids (DNA and RNA). Also, the nucleic acids include a wide range of artificial nucleic acids produced by artificially modifying chemical structures of ribose or chemical structures of phosphodiester bonds of the natural nucleic acids. Examples of the artificial nucleic acids include, but are not limited to, peptide nucleic acids (PNA), phosphorothioate-type oligonucleotides (S-oligo), bridged nucleic acids (BNA), locked nucleic acids (LNA), and the like.

Advantageous Effects of Disclosure

According to the present disclosure, it is possible to provide a microchip for nucleic acid analysis which can be used by a simple operation and which can exhibit stable performance even after long-term storage.

In an embodiment, there is provided a microchip including a reaction region and a detection region connected to the reaction region by a flow passage, the detection region including copper.

In another embodiment, a method of detecting a nucleic acid with a microchip is provided. The method includes moving a reacted nucleic acid from a reaction region of the microchip to a detection region of the microchip, and detecting fluorescence of the reacted nucleic acid after contacting the reacted nucleic acid with copper contained in the detection region.

In another embodiment, a method of manufacturing a microchip is provided. The method includes providing a reaction region, and providing a detection region that is connected to the reaction region by a flow passage, the detection region including copper.

Additional features and advantages are described herein, and will be apparent from the following Detailed Description and the figures.

BRIEF DESCRIPTION OF THE FIGURES

FIG. 1A is a drawing illustrating a configuration of a microchip for nucleic acid analysis according to a first embodiment of the present disclosure.

FIG. 1B is a drawing illustrating a configuration of a microchip for nucleic acid analysis according to a first embodiment of the present disclosure.

FIG. 2 is a drawing illustrating a configuration of a microchip for nucleic acid analysis according to a second embodiment of the present disclosure.

FIG. 3 is a drawing illustrating a configuration of a microchip for nucleic acid analysis according to a third embodiment of the present disclosure.

FIG. 4 is a drawing illustrating a configuration of a microchip for nucleic acid analysis according to a fourth embodiment of the present disclosure.

FIG. 5A is a drawing-substitute graph showing fluorescence spectra obtained by contact of ssDNA with $CuSO_4$ at varying concentrations under the condition of a S. A. concentration of 50 mM (Example 1).

FIG. 5B is a drawing-substitute graph showing RFU values obtained by contact of ssDNA with $CuSO_4$ at varying concentrations under the condition of a S. A. concentration of 50 mM (Example 1).

FIG. 6A is a drawing-substitute graph showing fluorescence spectra obtained by contact of ssDNA with $CuSO_4$ at varying concentrations under the condition of a S. A. concentration of 50 mM (Example 1).

FIG. 6B is a drawing-substitute graph showing FU values obtained by contact of ssDNA with $CuSO_4$ at varying concentrations under the condition of a S. A. concentration of 50 mM (Example 1).

FIG. 7A is a drawing-substitute graph showing fluorescence spectra obtained by contact of oligo-DNA with $CuSO_4$ at a concentration of 0.4 mM under the condition of a S. A. concentration of 4 mM (Example 1).

FIG. 7B is a drawing-substitute graph showing fluorescence spectra obtained by contact of oligo-DNA with $CuSO_4$ at a concentration of 0.4 mM under the condition of a S. A. concentration of 4 mM (Example 1).

FIG. 8A is a drawing-substitute graph showing a fluorescence spectrum obtained by contact of oligo-DNA with $CuSO_4$ at a concentration of 0.4 mM under the condition of a S. A. concentration of 4 mM (Example 1).

FIG. 8B is a drawing-substitute graph showing a fluorescence spectrum obtained by contact of oligo-DNA with $CuSO_4$ at a concentration of 0.4 mM under the condition of a S. A. concentration of 4 mM (Example 1).

FIG. 8C is a drawing-substitute graph showing a fluorescence spectrum obtained by contact of oligo-DNA with $CuSO_4$ at a concentration of 0.4 mM under the condition of a S. A. concentration of 4 mM (Example 1).

FIG. 8D is a drawing-substitute graph showing a fluorescence spectrum obtained by contact of oligo-DNA with $CuSO_4$ at a concentration of 0.4 mM under the condition of a S. A. concentration of 4 mM (Example 1).

FIG. 9 is a drawing-substitute graph showing changes over time of fluorescence spectra and absorption spectra obtained by oligo-DNA of T(20), T(6), and T(3) under the conditions of a $CuSO_4$ concentration of 0.4 mM and a S. A. concentration of 4 mM (Example 1), in which the fluorescence spectra against RFU values (absolute values) on the ordinate are shown in an upper portion, the fluorescence spectra against RFU values (relative values) on the ordinate are shown in a center portion, and the absorption spectra are shown in a lower portion.

FIG. 10A is a drawing-substitute graph showing changes over time of peak RFU values in fluorescence spectra obtained by oligo-DNA of T(20), T(6), and T(3) under the conditions of a $CuSO_4$ concentration of 0.4 mM and a S. A. concentration of 4 mM (Example 1).

FIG. 10B is a drawing-substitute graph showing changes over time of absorbance at a wavelength of 346 nm in absorption spectra obtained by oligo-DNA of T(20), T(6), and T(3) under the conditions of a $CuSO_4$ concentration of 0.4 mM and a S. A. concentration of 4 mM (Example 1).

FIG. 11A is a drawing-substitute graph showing a two-dimensional fluorescence spectrum obtained by oligo-DNA of T(20) (Example 1).

FIG. 11B is a drawing-substitute graph showing a two-dimensional fluorescence spectrum obtained by oligo-DNA of T(6) (Example 1).

FIG. 11C is a drawing-substitute graph showing a two-dimensional fluorescence spectrum obtained by oligo-DNA of T(3) (Example 1).

FIG. 12 is a drawing-substitute graph showing excitation spectra (broken lines) and fluorescence spectra (solid lines) obtained by oligo-DNA of T(20), T(6), and T(3) (Example 1).

FIG. 13A is a drawing-substitute graph showing fluorescence spectra obtained by oligo-DNA having 3-base length sequences containing an adenine-thymine pair (Example 1).

FIG. 13B is a drawing-substitute graph showing fluorescence spectra obtained by oligo-DNA having 3-base length sequences containing an adenine-thymine pair (Example 1).

FIG. 14A is a drawing-substitute graph showing RFU maximum values of fluorescence spectra obtained by oligo-DNA having 3-base length sequences containing an adenine-thymine pair (Example 1).

FIG. 14B is a drawing-substitute graph showing peak wavelengths of fluorescence spectra obtained by oligo-DNA having 3-base length sequences containing an adenine-thymine pair (Example 1).

FIG. 15A is a drawing-substitute graph showing fluorescence spectra obtained by oligo-DNA sequences described in Sequence ID No. 19 and Sequence ID No. 20 (Example 1).

FIG. 15B is a drawing-substitute graph showing fluorescence spectra obtained by oligo-DNA sequences described in Sequence ID No. 19 and Sequence ID No. 20 (Example 1).

FIG. 16 is a drawing-substitute graph showing fluorescence spectra obtained by contact of a sample containing ssDNA with solid copper (Example 2).

FIG. 17 is a drawing-substitute graph showing fluorescence spectra obtained by contact of a sample containing ssDNA with different concentrations of solid copper (Example 2).

FIG. 18A is a drawing-substitute graph showing fluorescence spectra obtained by contact of a sample containing ssDNA with solid copper in reaction solutions containing different concentrations of salt (Example 2).

FIG. 18B is a drawing-substitute graph showing fluorescence spectra obtained by contact of a sample containing ssDNA with solid copper in reaction solutions containing different types of salts (Example 2).

FIG. 19A is a drawing-substitute graph showing fluorescence spectra obtained by contact of samples containing different concentrations of ssDNA with solid copper (Example 2).

FIG. 19B is a drawing-substitute graph showing fluorescence spectra obtained by contact of samples containing different concentrations of RNA (B) with solid copper (Example 2).

FIG. 20A is a drawing-substitute graph showing fluorescence spectra obtained by contact of samples containing oligo-DNA having different sequences with solid copper (Example 2).

FIG. 20B is a drawing-substitute graph showing fluorescence spectra obtained by contact of samples containing oligo-DNA having different sequences with solid copper (Example 2).

FIG. 21C is a drawing-substitute graph showing a fluorescence spectrum obtained by contact of a sample containing oligo-DNA having a sequence with solid copper (Example 2).

FIG. 21D is a drawing-substitute graph showing a fluorescence spectrum obtained by contact of a sample containing oligo-DNA having a sequence with solid copper (Example 2).

FIG. 21E is a drawing-substitute graph showing a fluorescence spectrum obtained by contact of a sample containing oligo-DNA having a sequence with solid copper (Example 2).

FIG. 21F is a drawing-substitute graph showing a fluorescence spectrum obtained by contact of a sample containing oligo-DNA having a sequence with solid copper (Example 2).

FIG. 22A is a drawing-substitute graph showing excitation-fluorescence spectra obtained by contact of samples containing oligo-DNA having different sequences with solid copper (Example 2).

FIG. 22B is a drawing-substitute graph showing excitation-fluorescence spectra obtained by contact of samples containing oligo-DNA having different sequences with solid copper (Example 2).

FIG. 23 is a drawing-substitute graph showing fluorescence spectra obtained by oligo-DNA having sequences containing a pair of 8 cytosine bases and 12 thymine bases (Example 2).

FIG. 24A is a drawing-substitute graph showing fluorescence spectra obtained by double-stranded DNA containing a mismatch (Example 2).

FIG. 24B is a drawing-substitute graph showing fluorescence spectra obtained by double-stranded DNA containing a mismatch (Example 2).

FIG. 25A is a drawing-substitute graph showing RFU values obtained by changing the type and pH of a buffer in a reaction solution (Example 2).

FIG. 25B is a drawing-substitute graph showing RFU values obtained by changing the type and pH of a buffer in a reaction solution (Example 2).

FIG. 25C is a drawing-substitute graph showing RFU values obtained by changing the type and pH of a buffer in a reaction solution (Example 2).

FIG. 26A is a drawing-substitute graph showing a fluorescence image obtained by contact of ssDNA with copper sputtered on a glass surface (Example 3).

FIG. 26B is a drawing-substitute graph showing a fluorescence image obtained by contact of ssDNA with copper sputtered on a glass surface (Example 3).

FIG. 27A is a drawing-substitute graph showing a fluorescence image obtained by contact of RNA with copper sputtered on a glass surface (Example 3).

FIG. 27B is a drawing-substitute graph showing a fluorescence image obtained by contact of RNA with copper sputtered on a glass surface (Example 3).

FIG. 28 is a drawing-substitute graph showing fluorescence intensities obtained by contact of samples containing DNA or RNA with copper or silver sputtered on a glass surface (Example 3).

FIG. 29 is a drawing-substitute graph showing changes over time of fluorescence intensity obtained by contact of ssDNA with copper sputtered on a glass surface (Example 3).

FIG. 30 is a drawing-substitute graph showing changes in fluorescence intensity with changes in temperature after contact of ssDNA with copper sputtered on a glass surface (Example 3).

FIG. 31A is a drawing-substitute graph showing a result of fluorescence observation of an onion skin on a copper sputtered glass (Example 4).

FIG. 31B is a drawing-substitute graph showing a result of fluorescence observation of an onion skin on a copper sputtered glass (Example 4).

FIG. 31C is a drawing-substitute graph showing a result of fluorescence observation of an onion skin on a copper sputtered glass (Example 4).

FIG. 31D is a drawing-substitute graph showing a result of fluorescence observation of an onion skin on a copper sputtered glass (Example 4).

FIG. 31E is a drawing-substitute graph showing a result of fluorescence observation of an onion skin on a copper sputtered glass (Example 4).

FIG. 32A is a drawing-substitute graph showing a result of fluorescence observation of a human leukocyte sample on a copper sputtered glass (Example 4).

FIG. 32B is a drawing-substitute graph showing a result of fluorescence observation of a human leukocyte sample on a copper sputtered glass (Example 4).

FIG. 33A is a drawing-substitute graph showing a result of fluorescence observation of Jurkat cells on a copper sputtered glass (Example 4).

FIG. 33B is a drawing-substitute graph showing a result of fluorescence observation of Jurkat cells on a copper sputtered glass (Example 4).

FIG. 33C is a drawing-substitute graph showing a result of fluorescence observation of Jurkat cells on a copper sputtered glass (Example 4).

FIG. 33D is a drawing-substitute graph showing a result of fluorescence observation of Jurkat cells on a copper sputtered glass (Example 4).

FIG. 34A is a drawing-substitute graph showing a result of fluorescence observation of Jurkat cells on a copper sputtered glass (Example 4).

FIG. 34B is a drawing-substitute graph showing a result of fluorescence observation of Jurkat cells on a copper sputtered glass (Example 4).

FIG. 35A is a drawing-substitute graph showing a fluorescence spectrum obtained by oligo-DNA of T(20) at a concentration (Example 5).

FIG. 35B is a drawing-substitute graph showing a fluorescence spectrum obtained by oligo-DNA of T(20) at a concentration (Example 5).

FIG. 35C is a drawing-substitute graph showing a fluorescence spectrum obtained by oligo-DNA of T(20) at a concentration (Example 5).

FIG. 35D is a drawing-substitute graph showing a fluorescence spectrum obtained by oligo-DNA of T(20) at a concentration (Example 5).

FIG. 35E is a drawing-substitute graph showing a fluorescence spectrum obtained by oligo-DNA of T(20) at a concentration (Example 5).

FIG. 35F is a drawing-substitute graph showing a fluorescence spectrum obtained by oligo-DNA of T(20) at a concentration (Example 5).

FIG. 36A is a drawing-substitute graph showing a fluorescence spectrum obtained by oligo-DNA of T(10) at a concentration (Example 5).

FIG. 36B is a drawing-substitute graph showing a fluorescence spectrum obtained by oligo-DNA of T(10) at a concentration (Example 5).

FIG. 36C is a drawing-substitute graph showing a fluorescence spectrum obtained by oligo-DNA of T(10) at a concentration (Example 5).

FIG. 36D is a drawing-substitute graph showing a fluorescence spectrum obtained by oligo-DNA of T(10) at a concentration (Example 5).

FIG. 36E is a drawing-substitute graph showing a fluorescence spectrum obtained by oligo-DNA of T(10) at a concentration (Example 5).

FIG. 37A is a drawing-substitute graph showing a fluorescence spectrum obtained by oligo-DNA of T(6) at a concentration (Example 5).

FIG. 37B is a drawing-substitute graph showing a fluorescence spectrum obtained by oligo-DNA of T(6) at a concentration (Example 5).

FIG. 37C is a drawing-substitute graph showing a fluorescence spectrum obtained by oligo DNA of T(6) at a concentration (Example 5).

FIG. 37D is a drawing-substitute graph showing a fluorescence spectrum obtained by oligo DNA of T(6) at a concentration (Example 5).

FIG. 37E is a drawing-substitute graph showing a fluorescence spectrum obtained by oligo-DNA of T(6) at a concentration (Example 5).

FIG. 38A is a drawing-substitute graph showing a fluorescence spectrum obtained by oligo-DNA of T(5) at a concentration (Example 5).

FIG. 38B is a drawing-substitute graph showing a fluorescence spectrum obtained by oligo-DNA of T(5) at a concentration (Example 5).

FIG. 38C is a drawing-substitute graph showing a fluorescence spectrum obtained by oligo-DNA of T(5) at a concentration (Example 5).

FIG. 38D is a drawing-substitute graph showing a fluorescence spectrum obtained by oligo-DNA of T(5) at a concentration (Example 5).

FIG. 38E is a drawing-substitute graph showing a fluorescence spectrum obtained by oligo-DNA of T(5) at a concentration (Example 5).

FIG. 38F is a drawing-substitute graph showing a fluorescence spectrum obtained by oligo-DNA of T(5) at a concentration (Example 5).

FIG. 39A is a drawing-substitute graph showing a fluorescence spectrum obtained by oligo-DNA of T(4) at a concentration (Example 5).

FIG. 39B is a drawing-substitute graph showing a fluorescence spectrum obtained by oligo-DNA of T(4) at a concentration (Example 5).

FIG. 39C is a drawing-substitute graph showing a fluorescence spectrum obtained by oligo-DNA of T(4) at a concentration (Example 5).

FIG. 39D is a drawing-substitute graph showing a fluorescence spectrum obtained by oligo-DNA of T(4) at a concentration (Example 5).

FIG. 39E is a drawing-substitute graph showing a fluorescence spectrum obtained by oligo-DNA of T(4) at a concentration (Example 5).

FIG. 40A is a drawing-substitute graph showing a fluorescence spectrum obtained by oligo-DNA of T(3) at a concentration (Example 5).

FIG. 40B is a drawing-substitute graph showing a fluorescence spectrum obtained by oligo-DNA of T(3) at a concentration (Example 5).

FIG. 40C is a drawing-substitute graph showing a fluorescence spectrum obtained by oligo-DNA of T(3) at a concentration (Example 5).

FIG. 40D is a drawing-substitute graph showing a fluorescence spectrum obtained by oligo-DNA of T(3) at a concentration (Example 5).

FIG. 40E is a drawing-substitute graph showing a fluorescence spectrum obtained by oligo-DNA of T(3) at a concentration (Example 5).

FIG. 41A is a drawing-substitute graph showing a fluorescence spectrum obtained by oligo-DNA of T(2) at a concentration (Example 5).

FIG. 41B is a drawing-substitute graph showing a fluorescence spectrum obtained by oligo-DNA of T(2) at a concentration (Example 5).

FIG. 41C is a drawing-substitute graph showing a fluorescence spectrum obtained by oligo-DNA of T(2) at a concentration (Example 5).

FIG. 41D is a drawing-substitute graph showing a fluorescence spectrum obtained by oligo-DNA of T(2) at a concentration (Example 5).

FIG. 41E is a drawing-substitute graph showing a fluorescence spectrum obtained by oligo-DNA of T(2) at a concentration (Example 5).

FIG. 41F is a drawing-substitute graph showing a fluorescence spectrum obtained by oligo-DNA of T(2) at a concentration (Example 5).

FIG. 41G is a drawing-substitute graph showing a fluorescence spectrum obtained by oligo-DNA of T(2) at a concentration (Example 5).

FIG. 42A is a drawing-substitute graph showing a fluorescence spectrum obtained by oligo-DNA containing a number of thymine bases (Example 5).

FIG. 42B is a drawing-substitute graph showing a fluorescence spectrum obtained by oligo-DNA containing a number of thymine bases (Example 5).

FIG. 42C is a drawing-substitute graph showing a fluorescence spectrum obtained by oligo-DNA containing a number of thymine bases (Example 5).

FIG. 42D is a drawing-substitute graph showing a fluorescence spectrum obtained by oligo-DNA containing a number of thymine bases (Example 5).

FIG. 42E is a drawing-substitute graph showing a fluorescence spectrum obtained by oligo-DNA containing a number of thymine bases (Example 5).

FIG. 42F is a drawing-substitute graph showing a fluorescence spectrum obtained by oligo-DNA containing a number of thymine bases (Example 5).

FIG. 42G is a drawing-substitute graph showing a fluorescence spectrum obtained by oligo-DNA containing a number of thymine bases (Example 5).

FIG. 43A is a drawing-substitute graph showing a relation between the concentration of oligo-DNA and maximum fluorescence intensity of oligo-DNA containing a number of thymine bases (Example 5).

FIG. 43B is a drawing-substitute graph showing a relation between the concentration of oligo-DNA and maximum fluorescence intensity of oligo-DNA containing a number of thymine bases (Example 5).

FIG. 43C is a drawing-substitute graph showing a relation between the concentration of oligo-DNA and maximum fluorescence intensity of oligo-DNA containing a number of thymine bases (Example 5).

FIG. 43D is a drawing-substitute graph showing a relation between the concentration of oligo-DNA and maximum fluorescence intensity of oligo-DNA containing a number of thymine bases (Example 5).

FIG. 43E is a drawing-substitute graph showing a relation between the concentration of oligo-DNA and maximum fluorescence intensity of oligo-DNA containing a number of thymine bases (Example 5).

FIG. 43F is a drawing-substitute graph showing a relation between the concentration of oligo-DNA and maximum fluorescence intensity of oligo-DNA containing a number of thymine bases (Example 5).

FIG. 43G is a drawing-substitute graph showing a relation between the concentration of oligo-DNA and maximum fluorescence intensity of oligo-DNA containing a number of thymine bases (Example 5).

FIG. 44A is a drawing-substitute graph showing a fluorescence spectrum obtained by oligo-DNA with a base sequence containing T and C (Example 6).

FIG. 44B is a drawing-substitute graph showing a fluorescence spectrum obtained by oligo-DNA with a base sequence containing T and C (Example 6).

FIG. 44C is a drawing-substitute graph showing a fluorescence spectrum obtained by oligo-DNA with a base sequence containing T and C (Example 6).

FIG. 44D is a drawing-substitute graph showing a fluorescence spectrum obtained by oligo-DNA with a base sequence containing T and C (Example 6).

FIG. 44E is a drawing-substitute graph showing a fluorescence spectrum obtained by oligo-DNA with a base sequence containing T and C (Example 6).

FIG. 44F is a drawing-substitute graph showing a fluorescence spectrum obtained by oligo-DNA with a base sequence containing T and C (Example 6).

FIG. 44G is a drawing-substitute graph showing a fluorescence spectrum obtained by oligo-DNA with a base sequence containing T and C (Example 6).

FIG. 44H is a drawing-substitute graph showing a fluorescence spectrum obtained by oligo-DNA with a base sequence containing T and C (Example 6).

FIG. 45A is a drawing-substitute graph showing a fluorescence spectrum obtained by oligo-DNA with a base sequence containing T and G (Example 6).

FIG. 45B is a drawing-substitute graph showing a fluorescence spectrum obtained by oligo-DNA with a base sequence containing T and G (Example 6).

FIG. 45C is a drawing-substitute graph showing a fluorescence spectrum obtained by oligo-DNA with a base sequence containing T and G (Example 6).

FIG. 45D is a drawing-substitute graph showing a fluorescence spectrum obtained by oligo-DNA with a base sequence containing T and G (Example 6).

FIG. 45E is a drawing-substitute graph showing a fluorescence spectrum obtained by oligo-DNA with a base sequence containing T and G (Example 6).

FIG. 45F is a drawing-substitute graph showing a fluorescence spectrum obtained by oligo-DNA with a base sequence containing T and G (Example 6).

FIG. 45G is a drawing-substitute graph showing a fluorescence spectrum obtained by oligo-DNA with a base sequence containing T and G (Example 6).

FIG. 45H is a drawing-substitute graph showing a fluorescence spectrum obtained by oligo-DNA with a base sequence containing T and G (Example 6).

FIG. 46 is a drawing-substitute graph showing fluorescence spectra obtained by oligo-DNA of T(10) and the same oligo-DNA modified with a quencher for T(10) (Example 7).

FIG. 47A is a drawing-substitute graph showing fluorescence spectra obtained by oligo-DNA of T(10) and U(9)G (Example 8).

FIG. 47B is a drawing-substitute graph showing fluorescence spectra obtained by oligo-DNA of T(10) and U(9)G (Example 8).

FIG. 48 is a drawing-substitute graph showing fluorescence spectra obtained by oligo-DNA of T(10), C(10), and C(4)MeC(6) (Example 8).

FIG. 49 is a drawing-substitute graph showing fluorescence spectra obtained by oligo-DNA of T(10), A(10), and I(9)G (Example 8).

DETAILED DESCRIPTION

Preferred embodiments for carrying out the present disclosure are described in detail below. The embodiments described below are illustrative of typical embodiments of the present disclosure and the scope of the present disclosure is not interpreted narrowly by the embodiments. Description is made in the following order.

1. Microchip for nucleic acid analysis according to first embodiment of the present disclosure
    (1) Overall configuration
    (2) Reaction region
    (3) Detection region
    Copper
    Salt
    (4) Method for nucleic acid analysis
    <Nucleic acid analysis after amplification reaction>
    <Nucleic acid analysis after electrophoresis>
    <Nucleic acid analysis after hybridization reaction>
    <Nucleic acid analysis after bisulfite reaction>

2. Microchip for nucleic acid analysis according to second embodiment of the present disclosure
  (1) Overall configuration
  (2) Method for nucleic acid analysis
3. Microchip for nucleic acid analysis according to third embodiment of the present disclosure
4. Microchip for nucleic acid analysis according to fourth embodiment of the present disclosure.

1. Microchip for Nucleic Acid Analysis According to First Embodiment of the Present Disclosure.

(1) Overall Configuration

FIGS. 1A and 1B are schematic drawings illustrating a configuration of a microchip 1a for nucleic acid analysis according to a first embodiment of the present disclosure. FIG. 1A is a top view, and FIG. 1B is a sectional view corresponding to a IB-IB section in FIG. 1A.

The microchip 1a for nucleic acid analysis (simply referred to as the "microchip 1a" hereinafter) includes an inlet portion 2, a reaction region 3, a detection region 4, a flow passage 51 which connects the inlet portion 2 to the reaction region 3, and a flow passage 52 which connects the reaction region 3 to the detection region 4. The flow passages 51 and 52 may be each provided with a valve (not shown) in order to prevent a backflow of a sample solution.

The microchip 1a can be formed by bonding together substrate layers in which the inlet 2, the reaction region 3, the detection region 4, and the flow passages 51 and 52 are formed. The inlet 2 etc. can be formed by, for example, wet etching or dry etching of a silicon or glass substrate layer or nano-inprinting, injection molding, or cutting of a plastic substrate layer. The substrate layers in which the inlet 2 etc. have been formed are bonded together by, for example, heat sealing, an adhesive, anode bonding, bonding with an adhesive sheet, or a general method such as plasma activated bonding, ultrasonic bonding, or the like, thereby producing the microchip 1a. When a substrate layer without light transparency, such as silicon, is used, a material with light transparency, such as glass, is preferably combined as a substrate layer to be bonded.

Examples of a material of the substrate layers include various plastics and glass such as PDMS (polydimethylsiloxane), PMMA (polymethyl methacrylate: acryl resin), PC (polycarbonate), PS (polystyrene), PP (polypropylene), PE (polyethylene), PET (polyethyleneterephthalate), and the like. As the material of the substrate layers, a material having light transparency, little autofluorescence, a small optical error due to little wavelength dispersion is preferably selected.

(2) Reaction Region

The reaction region 3 serves as a reaction field of nucleic acid reaction such as amplification reaction, electrophoresis, hybridization reaction, bisulfite reaction, or the like of a nucleic acid. A sample solution containing a nucleic acid to be analyzed is introduced from the inlet 2, passed through the flow passage 51, and then introduced into the reaction region 3. The inlet 2 may be, for example, an opening provided in the upper surface of the microchip 1a. Alternatively, the inlet 2 may be, for example, a puncture portion arranged to inject the sample solution into the chip from a syringe provided with an injection needle by penetrating the injection needle into the substrate layer constituting the microchip 1a.

Methods for nucleic acid amplification reaction include a PCR (polymerase chain reaction) method involving a temperature cycle, and various isothermal amplification methods not involving a temperature cycle. Examples of the isothermal amplification methods include a LAMP (Loop-Mediated Isothermal Amplification) method, a SMAP (Smart Amplification Process) method, a NASBA (Nucleic Acid Sequence-Based Amplification) method, an ICAN (Isothermal and Chimeric primer-initiated Amplification of Nucleic acids) method (registered trade name), a TRC (transcription-reverse transcription concerted) method, a SDA (strand displacement amplification) method, a TMA (transcription-mediated amplification) method, a RCA (rolling circle amplification) method, and the like. These methods for nucleic acid amplification reaction also include reaction methods involving determination of amplified nucleic acid chains, such as a real-time PCR (RT-PCT) method, a RT-LAMP method, and the like.

(3) Detection Region

After nucleic acid reaction is performed in the reaction region 3, the sample solution is passed through the flow passage 52 and introduced into the detection region 4. The detection region 4 serves as a detection field where copper 6 and a salt 7 are disposed.

As described in detail below in examples, the inventors newly found that complexes of nucleic acids with copper emit fluorescence. After nucleic acid reaction is performed in the reaction region 3, a nucleic acid is brought into contact with the copper 6 in the detection region 4, and fluorescence emitted from a complex of the nucleic acid with copper is detected.

<Copper>

The copper 6 is preferably solid copper or a solid containing copper. The solid copper is preferred because of easy arrangement in the detection region 4 and simplification of the chip structure. Also, the solid copper is preferred because it is stable against heat, light, vibration, impact, and the elapse of time, and the like, is little affected by production conditions and storage conditions of the chip, and makes handling of the chip easy.

Besides pure copper, a copper-containing alloy can be used as the solid copper. Examples of the shape of the solid copper include, but are not particularly limited to, a powder, fine particles, a rod, a wire, a plate, a foil, and the like. In addition, as shown in FIGS. 1A and 1B, a thin film containing copper may be formed on a surface of the substrate layer constituting the detection region 4 by sputtering, vapor deposition, coating, or the like. Sputtering and vapor deposition may be performed by a usual method, and coating can be performed by, for example, using an adhesive composition containing a copper powder.

The copper 6 is preferably disposed in such a state as not to cut off the light irradiating the detection region 4 and fluorescence emitted from a nucleic acid-copper complex. In use of a thin film of the copper 6, light transparency can be secured by using the thin film having a thickness of, for example, about 10 to 50 nm. In addition, the thin film may be disposed only on one of the sides of the detection region so that irradiation with excitation light and fluorescence detection may be performed from the opposite side. Further, the copper 6 may be disposed on only a portion of the inside or surface of the detection region 4 so as to secure light transparency.

However, the microchip for nucleic acid analysis according the embodiment of the present disclosure may contain the copper 6 disposed as a copper-containing solution. When the time for detection is desired to be shortened, the solution may be preferably used. In use of the solution, the solution is preferably used under a condition where a sufficient amount of copper (I) ions is present in the solution. Copper ions are generally stably present in the state of divalent cation, and univalent cation is unstable as compared with divalent cation. Therefore, an aqueous solution containing copper divalent cation, such as an aqueous $CuSO_4$ solution, is preferably mixed with a reducing agent which reduces copper (II) ion to copper (I) ion. As the reducing agent, for example, sodium ascorbate can be used.

The amount of the copper 6 is not particularly limited as long as fluorescence can be detected. The amount of the solid copper is appropriately determined according to a contact area between the sample solution and the copper 6, the ratio of the area to the volume of the sample solution, the shape of the detection region 4, the copper content, etc. For example, when a copper powder described below in the examples is used, the amount of the copper powder is preferably 37.5 mg or more relative to 1 ml of the sample solution. Alternatively, when glass substrates one of which is subjected to copper sputtering as described below in the examples are used, the distance between the glass substrates, i.e., the depth of the detection region 4, is desirably about 20 micrometers.

<Salt>

The detection region 4 preferably contains the salt 7 so that the concentration in a solution produced by mixing with the sample solution is 25 mM or more, preferably 50 mM or more (refer to FIGS. 18A and 18B of an example described below). The salt 7 is more preferably disposed so that the concentration in a solution produced by mixing with the sample solution is about 250 mM or more because stronger fluorescence is emitted. The type of the salt is not particularly limited as long as the advantages of the present disclosure are exhibited, and for example, sodium chloride (NaCl), potassium chloride (KCl), magnesium chloride ($MgCl_2$), and the like may be used. Sodium chloride or potassium chloride is preferred. These salts may be used alone or in combination of two or more.

When the sample solution contains a sufficient amount of salt, the detection region 4 may not contain the salt 7 or may contain a small amount of the salt 7. In order to perform nucleic acid amplification reaction in the reaction region 3, the sample solution contains a reagent for amplification reaction with a nucleic acid, and in a general reaction system, the salt concentration is adjusted to about 10 to 50 mM. For example, when the sample solution contains 10 mM of salt, the detection region 4 may contain the salt in an amount corresponding to at least a shortage of 40 mM. However, since stronger fluorescence is detected under the conditions of a salt concentration of as high as about 250 mM, the detection region 4 more preferably contains, for example, about 240 mM of the salt. In addition, the salt concentration in the sample solution can be increased to 50 mM or more by using an enzyme which shows activity even under the condition of a high salt concentration, and thus the detection region 4 may not contain the salt 7.

In order to perform electrophoresis of a nucleic acid in the reaction region 3, the sample solution contains a buffer solution for electrophoresis, and a buffer solution not containing a salt is generally used. In order to perform hybridization reaction of a nucleic acid in the reaction region 3, the sample solution contains a buffer solution for hybridization, and a general SSC (saline-sodium citrate) buffer solution contains about 150 mM of salt.

In the use of a solution containing copper as the copper 6 in the reaction region 4, when the solution contains a salt, the detection region 4 may not contain the salt 7 or may contain a small amount of the salt 7. In the use of a solution containing copper, for example, when a specified type of buffer solution, such as a HEPPSO buffer solution used in Example 1 described below, is used, fluorescence derived from a nucleic acid may be detected even in the absence of a salt.

(4) Method for Nucleic Acid Analysis

Next, a method for nucleic acid analysis using the microchip 1a is described.

First, the sample solution containing a nucleic acid to be analyzed is introduced into the reaction region 3 from the inlet 2. The sample solution can be introduced into the reaction region 3 by injection into the inlet 2 under pressure applied using a syringe, a pump, or the like. After the sample solution is injected into the inlet 2, the sample solution may be sent to the reaction region 3 by centrifugal force.

A solution not containing a component (for example, EDTA (ethylenediaminetetraacetic acid), Tris, or the like) such as a chelating agent which stabilizes copper (II) ions is preferably used as the sample solution (refer to FIGS. 25A, 25B, and 25C of an example described below). As the sample solution, a buffer such as HEPPSO, EPPS, POPSO, TAPS, PIPES, TAPS, CAPS, or the like can be used as the sample solution.

After the sample solution is introduced in the reaction region 3, predetermined nucleic acid reaction is performed. The nucleic acid reaction may be nucleic acid amplification reaction, electrophoresis, hybridization reaction, bisulfite reaction, or the like. The nucleic acid reaction can be performed by a usual method.

After the nucleic acid reaction is performed, the sample solution containing a nucleic acid after the reaction is introduced into the detection region 4 from the reaction region 3 and brought into contact with the copper 6. At the same time, when the detection region 4 contains the salt 7, the salt 7 is mixed and dissolved in the sample solution. The sample solution can be sent to the detection region 4 from the reaction region 3 by applying pressure to the inlet 2 using a syringe, a pump, or the lie. In addition, the sample solution may be sent to the detection region 4 from the reaction region 3 by centrifugal force.

Next, the detection region 4 is irradiated with light (excitation light), and fluorescence emitted from a nucleic acid-copper complex is detected. The excitation light preferably includes light in a wavelength region of about 300 to 420 nm and particularly preferably includes light in a wavelength region of about 330 to 380 nm in order to efficiently emit fluorescence from the complex. Further, in order not to inhibit fluorescence detection, the excitation light preferably includes light at a wavelength of about 420 nm or more with sufficiently low intensity and particularly preferably includes light at a wavelength of about 500 nm or more with sufficiently low intensity.

For example, a mercury lamp, a halogen lamp, a xenon lamp, a laser, LED, sunlight, or the like can be used as a light source of the excitation light. In addition, light within a desired wavelength region may be selected as the excitation light from the light emitted from the light source using a wavelength selection device such as an optical filter, a prism, a grating mirror, or the like.

Fluorescence is detected as fluorescence at a predetermined wavelength, fluorescence at a plurality of wavelengths, or a fluorescence spectrum within a predetermined wavelength region. Fluorescence is detected by a detection device such as a photodetector, a photodiode, a photomultiplier, a CCD (charge coupled device) camera, a CMOS (complementary metal-oxide semiconductor) camera, or the like, and according to demand, the detection device is combined with a collection device such as a lens, and a wavelength separation device such as an optical filter, a prism, a grating mirror, or the like. Fluorescence may be detected in a direction which is the same as or different from the direction in which the detection region 4 is irradiated with the excitation light.

In the case of the excitation light at a wavelength of about 360 nm, the wavelength of fluorescence emitted from the nucleic acid-copper complex is about 600 nm. Therefore, the wavelength separation device is preferably capable of separating only fluorescence at about 420 nm or more which is the upper limit of the preferred wavelength region of the excitation light, and is particularly preferably capable of separating only fluorescence at a wavelength of about 500 nm or more.

The intensity and spectrum of fluorescence emitted from the nucleic acid-copper complex vary depending on the type, concentration, base length, base sequence, and conformation of the nucleic acid, etc. (refer to examples). In particular, under the same conditions for nucleic acid reaction and with the same optical configuration for fluorescence detection, when a nucleic acid has a predetermined type, base length, base sequence, and conformation, information about the concentration of the nucleic acid can be obtained from the resultant fluorescence intensity and spectrum. The concentration of a nucleic acid is calculated, for example, based on a calibration curve formed by analyzing a nucleic acid with predetermined concentrations.

In particular, under the same conditions for nucleic acid reaction and with the same optical configuration for fluorescence detection, when a nucleic acid has a predetermined type, concentration, and base length, information about the base sequence and conformation of the nucleic acid can be obtained from the resultant fluorescence intensity and spectrum. The term "conformation" represents a single-stranded conformation or a double-stranded conformation, the presence and site of double strand formation, and the presence of site of mismatch in double strands. The base sequence and conformation of a nucleic acid are analyzed, for example, based on fluorescence intensities and spectra previously obtained from nucleic acids having predetermined base sequences and conformations.

<Nucleic Acid Analysis after Amplification Reaction>

After the amplification reaction of a nucleic acid is performed in the reaction region 3, fluorescence of the amplified nucleic acid is detected in the detection region 4 so that the type, concentration, base length, base sequence, and conformation of the specified nucleic acid of the nucleic acids contained in the sample solution can be analyzed.

<Nucleic Acid Analysis after Electrophoresis>

In addition, electrophoresis of a nucleic acid is performed in the reaction region 3, and a predetermined nucleic acid is separated from the nucleic acids contained in the sample solution and introduced into the detection region 4. The type, concentration, base length, base sequence, and conformation of the separated nucleic acid can be analyzed by detecting fluorescence intensity and spectrum.

<Nucleic Acid Analysis after Hybridization Reaction>

Further, as described in detail in examples, the intensity and spectrum of fluorescence emitted from a copper-nucleic acid complex change depending on the presence of a mismatch in a double-stranded nucleic acid. In the reaction region 3, a nucleic acid to be analyzed is hybridized with a full-match strand probe or mismatch strand probe, and the produced double-stranded nucleic acid is introduced into the detection region 4. Then, in the detection region 4, the fluorescence intensity and spectrum of the double stands are detected in the detection region 4 so that the base sequence of the nucleic acid to be analyzed can be analyzed by detecting the presence of a mismatch in the double-stranded nucleic acid base on the fluorescence intensity and spectrum.

Analysis of base sequences based on mismatch detection is particularly advantageous for diagnosing various disease risks by detecting genetic mutations or genetic polymorphisms such as single nucleotide polymorphisms (SNPs) and the like. The probe can be composed of DNA, RNA, peptide nucleic acid (PNA), phosphorothioate-type oligonucleotide, BNA (LNA), or the like.

<Nucleic Acid Analysis after Bisulfite Reaction>

After bisulfite reaction of a nucleic acid is performed in the reaction region 3, the presence of methylation of cytosine (C) in the base sequence of a nucleic acid can be analyzed by detecting fluorescence of the nucleic acid in the detection region 4. It is common knowledge that cytosine (C) in DNA molecules is methylated in intracellular genomes. The presence of methylation of cytosine (C) can be detected by detecting whether or not cytosine (C) is substituted by uracil in bisulfite reaction.

In the reaction region 3, bisulfite treatment of a nucleic acid is performed under proper conditions. As a result, only unmethylated cytosine (C) can be selectively converted to uracil.

Fluorescence resulting from a nucleic acid-copper complex is detected at high intensity with uracil and thymine and is not detected with cytosine and methylated cytosine (refer to examples). Therefore, after unmethylated cytosine in nucleic acids contained in the sample is selectively converted to uracil by bisulfite treatment, the presence and amount of methylation or demethylation of cytosine in a nucleic acid can be analyzed by examining an amount of change in fluorescence intensity and/or spectrum detected by the sample.

Methylation is analyzed by comparing the fluorescence intensity and/or spectrum detected by the sample before bisulfite treatment with that after the treatment. Since the amount of uracil produced by bisulfite treatment increases as the amount of unmethylated cytosine increases, information about the presence and amount of methylation or demethylation of cytosine in nucleic acids can be obtained by comparing the fluorescence of the sample before bisulfite treatment with that of the sample after the treatment.

As described above, the microchip 1a for nucleic acid analysis according to the embodiment of the present disclosure permits a nucleic acid to be optically analyzed by the simple operation of introducing a nucleic acid into the detection region 4 after the nucleic acid reaction in the reaction region 3 and then bringing the nucleic acid in contact with the copper 6. In addition, when the copper 6 disposed in the detection region 4 is stable solid copper which is easily disposed, the microchip 1a for nucleic acid analysis can be easily produced, stored, and used.

2. Microchip for Nucleic Acid Analysis According to Second Embodiment of the Present Disclosure (1) Overall Configuration FIG. 2 is a schematic drawing illustrating a configuration of a microchip 1b for nucleic acid analysis according to a second embodiment of the present disclosure.

The microchip 1b for nucleic acid analysis (simply referred to as the "microchip 1b" hereinafter) is used particularly for nucleic acid analysis involving electrophoresis. The microchip 1b includes electrophoretic channels 31 and 32 provided as a reaction region 3 for electrophoresis of nucleic acids. The microchip 1b is also provided with an inlet 2, a detection region 4, and a flow passage 52 which connects the reaction region 3 to the detection region 4. FIG. 2 shows a case where the detection region 4 includes a bent flow passage, but the detection region 4 may have an arbitrary shape and may be the same cylindrical region as in the microchip 1a.

In the microchip 1b, constituents other than the reaction region 3 can be the same as in the above-described microchip 1a. The configuration of the reaction region 3 of the microchip 1b is described in detail below.

An electrode 311 is disposed at one of the ends of the electrophoretic channel 31, the end serving as the inlet 2. In addition, an electrode 312 is disposed at the other end of the electrophoretic channel 31. The electrophoretic channel 32 crosses the electrophoretic channel 31 at a joint portion 33 and crosses the flow passage 52 at a joint portion 34. Further, electrodes 321 and 322 are disposed at the respective ends of the electrophoretic channel 32. The electrode 322 can be disposed at the joint portion 34.

The electrophoretic channel 32 is filled with a gel for electrophoresis within a region between the joint portions 33 and 34. Alternatively, within the same region, the electrophoretic channel 32 may be provided with a nano-pillar structure for electrophoresis as an alternate to the gel and filled with a buffer solution for electrophoresis. The gel and buffer solution used preferably do not contain a component (for example, EDTA, Tris, or the like) such as a chelating agent which stabilizes copper (II) ions. Examples of the buffer solution which can be used include buffers such as HEPPSO, EPPS, POPSO, TAPS, PIPES, TAPS, CAPS, and the like. In addition, a region between the joint portion 34 and the electrode 322 may be filled with the gel or buffer.

(2) Method for Nucleic Acid Analysis

First, a sample solution containing nucleic acids is introduced into the electrophoretic channel 31 from the inlet 2, and electrophoresis of nucleic acids is performed by applying negative and positive voltages to the electrodes 311 and 312, respectively. At the same time, a proper negative voltage is preferably applied to the electrodes 321 and 322 in order to prevent the nucleic acids from entering the electrophoretic channel 32 from the joint portion 33.

Next, in order to perform electrophoresis of nucleic acids present in the joint portion 33 toward the joint portion 34, negative and positive voltages are applied to the electrodes 321 and 322, respectively. At the same time, a proper positive voltage is preferably applied to the electrodes 311 and 312 in order to prevent the nucleic acids from excessively entering the electrophoretic channel 32 from the joint portion 33.

The nucleic acid electrophoresed to the joint portion 34 is moved to the detection region 4 by the buffer solution introduced from an opening 81 and is brought into contact with the copper disposed in the detection region 4 to form a complex. As described above, in the detection region 4, the type, concentration, base length, base sequence, and conformation of the separated nucleic acid can be analyzed by detecting the intensity and spectrum of fluorescence emitted from the complex. After analysis in the detection region 4, the buffer solution containing nucleic acids is discharged from an opening 91.

The buffer solution introduced from the opening 81 preferably does not contain a component such as a chelating agent which stabilizes copper (II) ions. Examples of the buffer solution which can be used include buffers such as HEPPSO, EPPS, POPSO, TAPS, PIPES, TAPS, CAPS, and the like. Alternatively, water not containing a buffer component may be used as an alternate to the buffer solution.

In electrophoresis of nucleic acids, a buffer solution not containing a salt is used for the sample solution. Therefore, like in the microchip 1a, a salt is preferably disposed in the detection region 4 so that the concentration in a solution produced by mixing with the sample solution is 25 mM or more, preferably 50 mM or more. When the buffer solution is continuously introduced from the opening 81, the salt is preferably disposed in a sustained-release form.

The detection region 4 may have a structure provided for promoting mixing of the sample solution with the salt. FIG. 2 shows an example in which mixing is promoted by providing a bent flow passage as the detection region 4. Alternatively, mixing can be promoted by changing the width and/or depth of the flow passage constituting the detection region 4 according to position.

The salt may be contained at the above-described concentration in the buffer solution introduced from the opening 81. However, the salt contained in the buffer solution introduced from the opening 81 may undesirably affect electrophoresis in the electrophoretic channel 32. In this case, the salt is disposed in the detection region 4 or a region between the joint portion 34 and the detection region 4 in the flow passage 52. When the buffer solution is continuously introduced from the opening 81, the salt is preferably disposed in a sustained-release form.

3. Microchip for Nucleic Acid Analysis According to Third Embodiment of the Present Disclosure FIG. 3 is a schematic drawing illustrating a configuration of a microchip 1c for nucleic acid analysis according to a third embodiment of the present disclosure.

Like the microchip 1b, the microchip 1c for nucleic acid analysis (simply referred to as the "microchip 1c" hereinafter) is used for nucleic acid analysis involving electrophoresis. The microchip 1c is different from the microchip 1b in that a flow passage 53 having an opening 82 at one of the ends is connected to a position between the detection region 4 and the joint portion 34 in the flow passage 52.

The opening 82 and the flow passage 53 function to introduce a salt solution into the flow passage 52. In the microchip 1c, the salt solution introduced from the opening 82 and the flow passage 53 can be added to the buffer solution introduced from the opening 81. Therefore, in the microchip 1c, a salt may not be contained in the buffer solution introduced from the opening 81 so that the salt contained in the buffer solution introduced from the opening 81 can be prevented from undesirably affecting electrophoresis in the electrophoretic channel 32. In addition, in the microchip 1c, the salt solution can be continuously introduced from the opening 82, and thus when the buffer solution is continuously introduced from the opening 81, the salt concentration in the detection region 4 can be easily maintained at a proper value.

4. Microchip for Nucleic Acid Analysis According to Fourth Embodiment of the Present Disclosure FIG. 4 is a schematic drawing illustrating a configuration of a microchip 1d for nucleic acid analysis according to a fourth embodiment of the present disclosure.

Like the microchips 1b and 1c, the microchip 1d for nucleic acid analysis (simply referred to as the "microchip 1d" hereinafter) is used for nucleic acid analysis involving electrophoresis. The microchip 1d is provided with, instead of the opening 82 in the microchip 1c, a salt solution tank 83 which stores a salt solution to be sent to the flow passage 52. Also, a waste liquid tank 92 which stores the buffer solution containing nucleic acids after analysis in the detection region 4 is provided instead of the opening 91 in the microchips 1b and 1c.

A microchip for nucleic acid analysis according to an embodiment of the present disclosure can also be configured as follows.

(1) A microchip for nucleic acid analysis including a reaction region and a detection region, wherein the detection region contains copper.

(2) The microchip for nucleic acid analysis described above in (1), wherein the copper is solid copper.

(3) The microchip for nucleic acid analysis described above in (1) or (2), wherein the detection region contains a salt.

(4) The microchip for nucleic acid analysis described above in (3), wherein the amount of the salt contained is determined so that the final concentration after the sample solution containing nucleic acids is introduced into the detection region is 50 mM or more.

(5) The microchip for nucleic acid analysis described above in any one of (2) to (4), wherein the solid copper is sputtered, vapor-deposited, or applied to the detection region.

(6) The microchip for nucleic acid analysis described above in (3) or (4), wherein the salt is sodium chloride or potassium chloride.

(7) The microchip for nucleic acid analysis described above in any one of (1) to (6), wherein the reaction region serves as a reaction field of amplification reaction, electrophoresis, hybridization reaction, or bisulfite reaction of nucleic acids.

(8) The microchip for nucleic acid analysis described above in (7), including an inlet through which the sample solution is introduced into the reaction region, and a flow passage which connects the reaction region to the detection region.

Example 1

Example 1 showed that when a nucleic acid is mixed in a solution in which Cu(I) ions are produced by reducing Cu(II) ions with ascorbic acid, orange fluorescence is emitted by ultraviolet irradiation under predetermined conditions.

<Material and Method>

Cu: An aqueous $CuSO_4$ solution and (+)-Sodium L-ascorbate (referred to as "S.A." hereinafter) were purchased from Sigma-Aldrich.

Nucleic acid: Sonicated Salmon Sperm DNA (referred to as "ssDNA" hereinafter) brought from BioDynamics Laboratory Inc. (Tokyo, Japan) was used. Custom oligos brought from Invitrogen Corporation were used as oligo-DNA.

Buffer solution (buffer): HEPPS brought from DOJINDO Laboratories (Kumamoto, Japan) was adjusted to pH 8.5 according to the protocol provided by the maker and used.

Fluorometer: NanoDrop 3300 (thermo Fisher Scientific, Inc., Waltham, Mass., USA) or F-4500 fluorescence spectrophotometer (Hitachi High Technologies Co., Ltd.) was used. A UV LED light source was used as excitation light of NanoDrop 3300, and fluorescence spectra obtained by excitation with the excitation light were measured. The relative fluorescence unit (RFU) at a wavelength where the spectral intensity was maximized was determined as a peak RFU value using an attached software. In addition, a quartz capillary and a dedicated adaptor cell manufactured by Helix Biomedical Accessories, Inc. were used in the F-4500 fluorescence spectrophotometer. NanoDrop 3300 was used unless otherwise specified below.

Absorptiometer: Absorption spectra were measured using NanoDrop 1000 Spectrophotometer.

Preparation of sample and fluorescent light measurement: Sodium chloride (250 mM), $CuSO_4$ (0 to 4 mM), S.A. (4 or 50 mM), and ssDNA (1 mg/ml) or oligo-DNA (50, 250, or 500 micromoles) were mixed with 50 mM of HEPPSO buffer to prepare 20 microliters of sample. S.A. has the function of reducing Cu(II) ions produced from $CuSO_4$ into Cu(I) ions in the mixed solution (refer to Non-Patent Literature 31).

<Results>

Each of FIGS. 5A, 5B, 6A, and 6B show fluorescence spectra and RFU values obtained by ssDNA with changing $CuSO_4$ concentrations under the condition of a S.A. concentration of 50 mM, in which (A) shows fluorescence spectra, and (B) shows peak RFU values.

Each of FIGS. 7A, 7B, and 8A to 8C shows fluorescence spectra obtained by oligo-DNA under the conditions of a $CuSO_4$ concentration of 0.4 mM and a S.A. concentration of 4 mM. The concentrations of oligo-DNA were 50, 50, 250, and 500 micromoles for 20, 10, 6, and 3 bases in length, respectively. FIGS. 7A and 7B show the results of oligo-DNA having base sequences of Sequence ID Nos. 1 to 6. The wavelength is shown in the abscissa, and the RFU value at each wavelength is shown in the ordinate in FIG. 7A, and a value obtained by dividing the RFU value at each wavelength by the RFU maximum value is shown in the ordinate in FIG. 7B. FIG. 8A shows the results of oligo-DNA (referred to as "T(20)" hereinafter) having the base sequence of Sequence ID No. 2, FIG. 8B shows the results of oligo-DNA (T(6)) having the base sequence of Sequence ID No. 10, FIG. 8C shows the results of oligo-DNA (T(3)) having the base sequence of Sequence ID No. 12, and FIG. 8D shows the results of oligo-DNA (A(3)) having the base sequence of Sequence ID No. 11. In FIGS. 8A, 8B, 8C, and 8D, the wavelength is shown in the abscissa, and the RFU value at each wavelength is shown in the ordinate.

The figures confirmed that the pattern (peak wavelength of intensity) of a fluorescence spectrum varies depending on the base sequences of nucleic acids.

Next, changes over time of fluorescence spectrum and absorption spectrum of oligo-DNA of each of T(20), T(6), and T(3) were measured under the conditions of a $CuSO_4$ concentration of 0.4 mM and a S.A. concentration of 4 mM. S. A. was added immediately before the first measurement of fluorescence spectrum and absorption spectrum, and then the fluorescence spectrum and absorption spectrum were measured 8, 14, 24, and 35 minutes after. The results are shown in FIGS. 9 and 10A an 10B. In FIG. 9, the fluorescence spectra against RFU values (absolute values) on the ordinate are shown in an upper portion, the fluorescence spectra against RFU values (relative values) on the ordinate are shown in a center portion, and absorption spectra are shown in a lower portion. FIG. 10A shows changes over time of the peak RFU value, and FIG. 10B shows changes over time of absorbance at a wavelength of 346 nm.

The figures indicate that with oligo-DNA of all of T(20), T(6), and T(3), fluorescence substantially disappears after the passage of 30 minutes. In particular, with the oligo-DNA with a short base length, fluorescence early disappears. When 1.8 microliters of the S. A. solution was again added to 44 mM of the sample immediately after measurement of fluorescence spectra 35 minutes after, fluorescence could be again detected. Therefore, it was considered that disappearance of fluorescence is due to oxidation of Cu(I) ions to Cu(II) ions. In addition, in the spectra of oligo-DNA of T(6) and T(3), a new peak appears on the short wavelength side with decreases in peak intensity.

On the other hand, in the absorption spectrum of each oligo-DNA, decreases in peak intensity over time were observed. The attenuation of absorption spectra was slower than that of fluorescence spectra.

FIGS. 11A to 11C show two-dimensional fluorescence spectra obtained by oligo-DNA of T(20), T(6), and T(3), respectively, with the F-4500 fluorescence spectrophotometer. FIG. 12 shows excitation spectra (broken lines) and fluorescence spectra (solid lines) of the oligo-DNA. The spectra were measured at fluorescent wavelength intervals of 1 nm and excitation wavelength intervals of 2 nm.

The figures confirmed that the pattern of a fluorescence spectrum varies depending on the base sequences of oligo-DNA. Also, it was confirmed that the pattern of an excitation spectrum changes depending on base lengths.

In order to further examine a relation between base sequence and spectrum, an experiment was conducted by measuring fluorescence of oligo-DNA having 3-base length sequences containing an adenine (A)-thymine (T) pair described in Sequence ID Nos. 11 to 18. The results are shown in FIGS. 13A, 13B, 14A, and 14B. In FIGS. 13A and 13B, the wavelength is shown in the abscissa, and the RFU value at each wavelength measured with NanoDrop is shown in the ordinate in FIG. 13A, and a value obtained by dividing the RFU value at each wavelength by the RFU maximum value is shown in the ordinate in FIG. 13B. FIGS. 14A and 14B show the averages and standard deviations obtained by three times of measurement of RFU maximum values and peak wavelengths.

Theses figures confirmed that the fluorescence intensity and peak wavelength vary depending on the base sequences of oligo-DNA.

FIGS. 15A and 15B show the results of the same measurement performed for oligo-DNA having sequences described in Sequence ID Nos. 19 and 20. It was confirmed that with oligo-DNA having the sequence described in Sequence ID No. 20 containing uracil (U), the fluorescence intensity is weak as compared with oligo-DNA having the sequence described in Sequence ID No. 19 containing only thymine (T), but the fluorescence emitted has a similar spectral shape and peak position.

<Consideration>

This example showed that when DNA is mixed with a HEPPSO buffer solution containing $CuSO_4$, S.A., and sodium chloride, orange fluorescence at a wavelength of about 500 nm to 700 nm is observed by ultraviolet irradiation. Also, it was confirmed that the fluorescence intensity depends on the $CuSO_4$ concentration, and the fluorescence intensity and spectra are also affected by base sequences of nucleic acids.

Fluorescence was confirmed from oligo-DNA containing at least thymine (T) and adenine (A) or uracil (U). The experiment using 3-base length oligo-DNA containing thymine (T) and adenine (A) indicated that fluorescence is observed with any one of the sequences, and the fluorescence intensity and spectra are affected by not only the amount of thymine (T) or adenine (A) but also the positions (order in the sequence) of thymine (T) and adenine (A) in oligo-DNA.

In addition, the fluorescence intensity attenuated with the passage of time after the addition of S. A., but the fluorescence intensity was recovered by again adding S.A. In addition, Cu(I) ions are very unstable in the presence of oxygen and are rapidly converted to Cu(II) or solid copper when the reducing effect of S.A. disappears. Therefore, it was considered that fluorescence is produced by a Cu(I) ion-nucleic acid complex. It was also considered that in order to detect fluorescence caused by the action of a nucleic acid with copper, it is preferred to minimize the contact of the reaction solution with oxygen in the air.

Example 2

In Example 2, it was found that when an aqueous solution containing a nucleic acid is brought into contact with solid copper, the same orange fluorescence as observed in Example 1 is emitted by ultraviolet irradiation under predetermined conditions.

<Material and Method>

As copper to be put in contact with a nucleic acid, a copper powder (Copper Powder, −75 um, 99.9%, Cat. No. 030-18352) manufactured by Wako Pure Chemical Industries, Ltd., Osaka, Japan was used.

Rat Brain Total RNA (Cat. No. 636622, Takara Bio Inc., Otsu, Japan) was used as RNA and dissolved in DEPC (diethyl pyrocarbonate) treated water (Cat. No. 312-90201, Wako Pure Chemical Industries, Ltd., Japan). PIPES, ACES, BES, TAPSO, HEPPSO, EPPS, TAPS, CAPS, TES, Tricine, and POPSO purchased from DOJINDO Laboratories (Kumamoto, Japan) were used and pH was adjusted according to a protocol provided by the maker. The other reagents used were the same as in Example 1.

Contact between a nucleic acid and copper was made by mixing a nucleic acid, salt, and copper powder with a total amount of 40 microliters of aqueous solution, and stirring the resultant mixture for 15 minutes. The amount of the copper powder added was 375 mg per ml of the aqueous solution unless otherwise specified. The amount of sodium chloride (NaCl) added as the salt was 500 mM unless otherwise specified.

A sample was centrifuged to precipitate the copper powder, and a fluorescence spectrum and intensity were measured for the supernatant. The fluorescence spectrum and intensity were measured according to the same procedures as in Example 1.

<Results>

FIG. 16 (abscissa: wavelength, ordinate: RFU) shows the results of three times of fluorescent measurement for a reaction solution containing 1.5 mg/ml of ssDNA. The figure indicates that fluorescence with a peak near 600 nm can be detected by UV excitation after contact between the solid copper and the sample containing a nucleic acid.

Next, FIG. 17 shows the results of three times of fluorescence measurement for a reaction solution containing 1.5 mg/ml of ssDNA and the copper powder added in an amount of each of 375 mg, 250 mg, 125 mg, 62.5 mg, 37.5 mg, 12.5 mg, and 0 mg per ml of the reaction solution. This figure indicates that the fluorescence intensity depends on the amount of the copper powder. With the Cu powder used in this example, fluorescence was clearly observed with 37.5 mg/ml or more of the Cu powder. On the other hand, fluorescence was not clearly observed with 12.5 mg/ml or less.

Then, a comparison was made between fluorescence intensities detected by changing the type and concentration of a salt in the reaction solution containing 1.5 mg/ml of ssDNA. The results are shown in FIGS. 18A and 18B. FIG. 18A shows fluorescence intensity detected by the reaction solution to which each of 0.5, 0.25, 0.1, 0.05, 0.025, and 0 M of sodium chloride (NaCl) was added. FIG. 18B shows fluorescence intensity detected by the reaction solution to which each of 0.45 M of sodium chloride (NaCl), 0.45 M of potassium chloride (KCl), 0.45 M of magnesium chloride ($MgCl_2$), and 45% ethanol (EtOH) was added. The fluorescence intensity is shown by RFU at 604 nm, and the average and standard deviation of three times of measurements are shown. The figures indicate that the fluorescence intensity depends on the concentration of sodium chloride, and also fluorescence was detected in coexistence of potassium chloride or magnesium chloride other than sodium chloride.

FIGS. 19A and 19B show the results of comparison of fluorescence intensities detected by changing the concentration of a nucleic acid added to the reaction solution. FIG. 19A shows fluorescence intensity detected by adding each of 5, 2.5, 1, 0.5, 0.25, 0.1, 0.05, and 0 mg/ml of ssDNA to the reaction solution. FIG. 19B shows fluorescence intensity detected by adding each of 2.5, 0.25, and 0 mg/ml of RNA to the reaction solution. The concentration of the nucleic acid is shown on the abscissa, and RFU at a fluorescence wavelength of 604 nm is shown on the ordinate. The measurement was performed three times. The concentration of sodium chloride (NaCl) was 0.25 M, and the ratio of the amount of copper powder was 200 mg per ml. These conditions were used in experiments below unless otherwise specified. These figures indicate that fluorescence intensity depends on the DNA concentration and RNA concentration.

Next, fluorescence was measured by a reaction solution to which 0.1 mM of oligo-DNA having each of the different sequences described in Sequence ID Nos. 1, 2, 5, 6, and 9 was added. The results are shown in FIGS. 20A and 20B. FIG. 20A shows RFU values measured with NanoDrop on the ordinate, and FIG. 20B shows RFU values as relative values to 1 of a peak height on the ordinate. The figures indicate that the fluorescence intensity and peak wavelength are affected by base sequences. In particular, it was confirmed that with thymine (T) at a high ratio, the fluorescence intensity tends to be increased, and the peak wavelength tends to become long.

The reaction solution to which 0.1 mM of olio DNA having each of the different sequences described in Sequence ID Nos. 1, 2, 5, and 6 was added was also measured using the F-4500 fluorescence spectrophotometer. FIGS. 21C to 21F show the results of measurement of fluorescence spectra (slit width 2.5 nm) in 400 nm to 700 nm by irradiation with excitation light at 360 nm (slit width 10 nm). In this case, it could be confirmed that in the case of a sequence containing a thymine (T)-adenine (A) pair, as the ratio of thymine (T) increases, the fluorescence intensity tends to increase and the peak wavelength tends to become long. FIGS. 22A and 22B show the results of measurement of excitation-fluorescence spectra performed by scanning the excitation light in 330 nm to 390 nm (slit width 3 nm) and 400 nm to 700 nm (slit width 2.5 nm). FIG. 22A shows a three-dimensional display, and FIG. 22B shows a contour display. In these figures, the axis EX shows the excitation wavelength (nm), the axis EM shows the fluorescent wavelength (nm), and the height direction shows fluorescence intensity. It can be read from the results that the excitation and fluorescence spectra and intensity vary with changes in base sequences of DNA.

In order to further examine a relation between base sequences and spectra, an experiment was conducted by measuring fluorescence of oligo-DNA having sequences containing 8 cytosine (C) bases and 12 thymine (T) bases described in Sequence ID Nos. 21 to 26. The results are shown in FIG. 23. This figure indicates that the fluorescence intensity varies with changes in sequence even with the same oligo-DNA base composition.

Next, an experiment was conducted by measuring patterns of fluorescence spectra of double-stranded DNA containing a mismatch. As the double-stranded DNA, the three types including a mixture ((e)+(f)) of oligo-DNA having the sequence of Sequence ID No. 1 and oligo-DNA having the sequence of Sequence ID No. 2, a mixture ((d)+(f)) of oligo-DNA having the sequence of Sequence ID No. 5 and oligo-DNA having the sequence of Sequence ID No. 2, and a mixture ((e)+(c)) of oligo-DNA having the sequence of Sequence ID No. 1 and oligo-DNA having the sequence of Sequence ID No. 6 were used. Any type of the oligo-NA was mixed at a final concentration of 0.5 mg/ml. The results are shown in FIGS. 24A and 24B. FIG. 24A shows RFU values measured with NanoDrop on the ordinate, and FIG. 24B shows RFU values as relative values to 1 of the peak height on the ordinate. The wavelength (nm) is shown on the abscissa. As shown in the figures, it was confirmed that double-stranded DNA shows low fluorescence intensity as compared with single-stranded DNA, but double-stranded DNA containing a thymine (T)-thymine (T) mismatch shows strong fluorescence.

Comparison was made between fluorescence intensities detected by changing the type and pH of a buffer in a reaction solution. The results are shown in FIGS. 25A to 25C. FIG. 25A shows relative values of peak RFU values of a sample (+) containing ssDNA and a sample (−) not containing a nucleic acid under the buffer conditions. FIG. 25B shows relative values of peak RFU values of a sample containing oligo-DNA having the sequence of Sequence ID No. 1 under the same conditions. FIG. 25C shows relative values of peak RFU values of a sample containing oligo-DNA having the sequence of Sequence ID No. 2 under the same conditions. The buffer concentration was 50 mM, the final concentration of ssDNA was 0.5 mg/ml, and the final concentration of oligo-DNA was 25 mM. The relative values of peak RFU values each represent a relative value to 1 of a peak RFU value measured under conditions not containing the buffer. The fluorescence intensity depends on the types of buffers. With any one of the buffers, substantially no fluorescence was detected in the absence of a nucleic acid.

<Consideration>

The results in this example indicate that like in contact between a nucleic acid and Cu(I) ions, even in contact between a nucleic acid and a solid copper powder, fluorescence can be detected under the condition of a proper salt concentration. In the case of ions and the case of solid copper, properties such as the wavelength characteristics and sequence dependence are substantially the same, and thus in both cases, fluorescence observed was considered to be due to the same mechanism. In addition, fluorescence was observed using RNA as a nucleic acid. In particular, when a thymine (T)-thymine (T) mismatch was present in double-stranded DNA, strong fluorescence was observed. This suggested the possibility that bonding with a complementary sequence becomes an inhibitory factor to the formation of a fluorescent material by bonding between a nucleic acid and copper. In addition, it was considered that an increase in fluorescence intensity in a mismatch site can be applied to a method for detecting a mutation contained in the base sequence of a nucleic acid.

In addition, in the experiment of comparison of fluorescence under various buffer conditions, fluorescence was observed in the buffers of PIPES, BES, HEPPSO, EPPS, TAPS, CAPS, TES, and POPSO, and particularly strong fluorescence was observed in the buffers of PIPES, HEPPSO, EPPS, and POPSO. Fluorescence could be observed within a pH range of 7.0 to 10.5. Also, it was found that changes in fluorescence intensity depending on the type and pH of the buffer show different patterns according to base sequences of nucleic acids. On the other hand, there was found the tendency that fluorescence is not observed in a solution containing a buffer having the property of stabilizing Cu(II) ions by chelating. Although data is not described in the example, substantially no fluorescence was observed in the use of a reaction solution containing, for example, a Tris buffer, EDTA, or the like.

Example 3

In Example 3, it was confirmed that fluorescence can be detected after a nucleic acid is brought into contact with copper sputtered on a glass surface, and characteristics of fluorescence were analyzed.

<Material and Method>

The same ssDNA as described in Example 1 was used as DNA, and the same RNA as described in Example 2 was used. Copper was sputtered on the glass surface with a Cu target of 99.99% (Kojundo Chemical Laboratory Co., Ltd., Saitama, Japan) mounted on an apparatus SH-350 of ULVAC, Inc. (Kanagawa, Japan). The thickness of the sputtered copper was 40 nm, and the sputtering time was appropriately determined based on a deposition rate previously measured. A silver sputtered glass manufactured by Kyodo International, Inc., (Kanagawa, Japan) was used.

A sample solution was placed on a copper or silver-sputtered slide glass or an untreated slide glass and covered with a gap cover glass of 24*25 (No. 4, #CG00024, Matsunami Glass, Ind., Ltd., Osaka, Japan). After the glass was allowed to stand for about 5 minutes, fluorescence was observed. The observation was performed using an inverted microscope Ti-U (manufactured by Nikon Co., Tokyo, Japan), and fluorescent photography was performed using filter set UV-1A (Ex: 365/10, DM: 400, BA: 400, Nikon). An image was taken and recorded by using a digital CCD camera Retiga 2000R (QImaging, BC, Canada) and a 20-times objective lens.

<Results>

FIGS. 26A and 26B show images taken after the sample containing 5 mg/ml of DNA and 0.5 M NaCl was allowed to stand on the copper sputtered glass for 5 minutes. FIGS. 27A and 27B show images taken after the sample containing 5 mg/ml of RNA and 0.5 M NaCl was allowed to stand on the copper sputtered glass for 5 minutes.

As shown in FIG. 26A, when the sample containing DNA was used, smooth fluorescence was observed over the entire imaging region. On the other hand, as shown in FIGS. 27A and 27B, when the sample containing RNA was used, fluorescence with a specific wavelike pattern extending in the imaging region was observed. The specific pattern of RNA was estimated to be due to a conformation formed by hybridization of single-stranded RNA.

Next, the fluorescence intensity in the imaging region was converted into numbers. Each of the images taken was divided into 9 parts as illustrated in FIG. 26B, the ⅑ section (portion C in the drawing) at the center was regarded as a measurement region, and an average value of fluorescence intensity in the measurement region was calculated. Each of the samples was photographed at any desired 5 positions on the slide glass, and the average of the images was calculated. Further, the obtained 5 average values were averaged, and standard deviation was calculated.

FIG. 28 shows the fluorescence intensity obtained by contact of the sample containing DNA or RNA with copper or silver sputtered on the glass. In FIG. 28, "DNA/Cu", "RNA/Cu", and "(−)/Cu" show the results of fluorescence intensity measured on the Cu sputtered glass using the sample containing 5 mg/ml of DNA, the sample containing 5 mg/ml of RNA, and the sample not containing a nucleic acid, respectively. In addition, "DNA/Ag", "RNA/Ag", and "(−)/Ag" show the results of fluorescence intensity measured on the Ag sputtered glass using the sample containing 5 mg/ml of DNA, the sample containing 5 mg/ml of RNA, and the sample not containing a nucleic acid, respectively. Each of the samples contained 0.5 M of NaCl. Further, the fluorescence intensity of "DNA/Cu" was particularly strong as compared with the other samples, and thus the exposure time of "DNA/Cu" was 1 second, while the exposure time of the other samples was 5 seconds.

This figure indicates that on the Cu sputtered glass, the fluorescence intensities of "DNA/Cu" and "RNA/Cu" are high as compared with "(−)/Cu", and particularly strong fluorescence is detected with the DNA sample. On the other hand, on the Ag sputtered glass, the fluorescence intensities of both "DNA/Ag" and "RNA/Ag" are not higher than the intensity of "(−)/Ag". However, "(−)/Ag" shows a higher measured value than "(−)/Cu". This was considered to be due to the background resulting from reflected light, scattered light, or autofluorescence of the Ag sputtered surface.

Next, changes over time of fluorescence intensity with the passage of time of contact between a nucleic acid and copper were examined. The time when a sample containing 5 mg/ml of ssDNA and 0.5 M of NaCl was placed between a Cu sputtered glass and a gap cover glass was considered as a starting point, and fluorescence intensity was measured each time of the passage of a predetermined time. Photography was performed at intervals of 15 seconds, and the shutter for the excitation light was opened and closed at each time of photography. The objective lens had a magnification of 10 times, and the exposure time was 1 second. The fluorescence intensity was measured using an image taken at each of the times. The results are shown in FIG. 29.

FIG. 29 indicates that the fluorescence intensity gradually increases within several minutes after the sample was introduced and reaches the maximum about 3 minutes after.

Then, after the passage of a predetermined time from contact between a nucleic acid and copper, changes in fluorescence intensity with changes in temperature were measured. The temperature immediately after photography was kept at room temperature, and a heat block heated to 65 Celsius degrees was gently placed on a Cu sputtered glass 50 seconds after and the heat block was removed 100 seconds after. Photography was performed at intervals of 5 seconds. Measurement was stopped 150 seconds after, and the shutter for the excitation light was closed. Further, measurement was again started 900 seconds after. The results are shown in FIG. 30.

The figure shows that fluorescence intensity gradually attenuates within first 50 seconds. This was considered to be due to fluorescence photobleaching. Then, the disappearance of fluorescence at a rate apparently different from that of photobleaching was observed within next 50 seconds. After the heat block was removed to recover the room temperature condition, fluorescence was gradually recovered. Further, 900 seconds after, the fluorescence intensity was returned to a level determined by subtracting the fluorescence intensity corresponding to photobleaching from the initial fluorescence intensity. These results indicated that fluorescence emitted from a nucleic acid in contact with copper is sensitive to heat, and fluorescence reversibly disappears with increases in temperature.

Example 4

Example 4 showed that fluorescence of cell nuclei can be observed by introducing a sample containing cells on a copper sputtered glass.

<Material and Method>

Dulbecco's Phosphate Buffered Saline, Ca/Mg free (Invitrogen Corporation, CA, USA) was used as PBS.

In an experiment with an onion skin, a commercial onion skin was carefully peeled with a pincette, rinsed by immersion in distilled water, and used. The onion skin was placed on a Cu sputtered glass and covered with a cover glass in a state of being immersed in PBS, followed by observation.

An experiment with a human leukocyte sample was performed using IMMUNO-TROL Cells (Cat. No. 6607077, Beckman Coulter, Inc., Fullerton, Calif., USA) which were treated according to the following procedures. First, 500 microliters of IMMUNO-TROL Cells was taken out and washed with PBS, and then cells were precipitated by a centrifugal separator (1200 rpm, 5 minutes). Then, the supernatant was removed, and the residual pellet was loosened and hemolyzed in water two times to prepare a sample. The sample was diluted with PBS to prepare a leukocyte sample. Hemolysis in water was conducted by, after sufficiently loosening the pellet resulting from centrifugal separation, adding 9 milliliters deionized water to the pellet, mixing them by inversion for 30 seconds, further adding 1 milliliter of 10×PBS Buffer (Nippon Gene Co., Ltd., Tokyo, Japan) to the mixture, sufficiently stirring the mixture, precipitating cells by centrifugal separation (1200 rpm, 5 minutes), and then removing the supernatant. The leukocyte sample was placed on a Cu sputtered glass and covered with a cover glass, followed by observation.

The copper sputtered glass, cover glass, and microscope used were the same in Example 3. The thickness of sputtered Cu was 20, 40, or 100 nm. The Cu sputtered to a thickness of 40 nm was used in the experiment below unless otherwise specified. When Cu was sputtered only on a portion of the surface of the slide glass, sputtering was performed under a condition in which a polyimide tape was applied to the surface of the slide glass excluding a 5-mm square region at the center. Then, the polyimide tape was removed to form the Cu sputtered glass in which a Cu layer was formed only in the 5-mm square region at the center.

Fluorescence of the onion skin was observed using an excitation filter (365/10 nm), a dichroic mirror (400 nm), and a fluorescence filter (590LP). Fluorescence of the leukocyte sample and Jurkat cells was observed using a filter set UV-1A (Ex: 365/10, DM: 400, BA: 400, Nikon).

<Results>

FIGS. 31A to 31E show images taken by fluorescence observation of the onion skin on the copper sputtered glass. FIGS. 31A and B show images observed on the Cu sputtered glass, and FIGS. 31C and D show images observed on the slide glass on which Cu was not sputtered. In addition, FIGS. 31A and C show images observed in a bright field, and FIGS. 31B and D show fluorescence images. The images shown in FIGS. 31A to D were taken using a 10-times objective lens, and the image shown in FIG. 31E was taken using a 40-times objective lens.

As shown in the figures, strong fluorescence specific to cell nuclei was observed with the cells on the Cu sputtered glass. Although slight fluorescence was observed from part of the cell walls, this was considered to be autofluorescence of cell walls because this was also confirmed with the cells on the slide glass on which Cu was not stuttered.

Next, animal cells were observed. FIGS. 32A and 32B show images taken by fluorescence observation of the human leukocyte sample on the copper sputtered glass. FIG. 32A shows an image observed in a bright field, and FIG. 32B shows a fluorescence image. A 40-times objective lens was used.

In the fluorescence image, the formation of segmented nuclei specific to leukocytes such as neutrophiles was clearly recognized.

FIGS. 33A to 33D show images observed using a Cu sputtered glass in which Cu was sputtered only on a portion of a surface of a slide glass. Jurkat cells derived from a human leukocyte strain were placed on the Cu sputtered glass and covered with a cover glass, followed by observation with a 20-times objective lens. Each of the images was taken in a boundary between a Cu-deposited region and a Cu-undeposited region of the Cu sputtered glass. FIGS. 33A and 33C show images observed in a bright field, in each of which a black region occupying a major part was a region not transmitting light because the Cu layer was formed. FIGS. 33B and 33D show fluorescence images.

Strong fluorescence was observed only with the cell nuclei of the cells present in the Cu-deposited region. FIGS. 34A and 34B show results of observation of Jurkat cells using a Cu sputtered glass having a Cu layer formed to a thickness of 20 nm (A) or 100 nm (B) thereon. With any one of the thicknesses, fluorescence was observed from cell nuclei.

<Consideration>

The results in the example indicated that fluorescence can be detected by contact of cell nuclei with copper. This phenomenon obviously resulted from the action of cell nuclei with copper because this was observed only on a copper sputtered glass substrate.

In addition, as a result of fluorescence observation of the onion skin cells and leukocyte cells, a difference in shape between both types of cell nuclei could be clearly observed. This revealed that the detection method for nucleic acids according to the present disclosure is capable of discriminating among the shapes of cell nuclei different according to cell types.

Although not described in the example, in an experiment using a slide glass in which copper was sputtered only on a portion of the surface of the slide glass, a state where fluorescence was observed from only cells present in the Cu-deposited region was recognized, and then the slide glass was inclined to move the cells from the Cu-deposited region to the Cu-undeposited region. As a result, fluorescence was continuously observed after the movement. This revealed that even when a site of contact between copper and cells is provided apart from a site of fluorescence observation of cells, fluorescence can be detected by providing a sample moving device between both sites.

After fluorescence was observed from the cell nuclei present between the Cu sputtered glass and the cover glass, fluorescence rapidly disappeared when the cover glass was removed to expose the solution containing the cells in air. In the experiment using Cu(II) ions and S.A. in Example 1, it was found that fluorescence disappears by exposing the reaction solution in air for a long period of time. The disappearance of fluorescence was considered to be due to oxidation of Cu(I) ions by contact with air. Therefore, contact of the sample solution with air (particularly, exposure to oxygen contained in air) is considered to be an inhibitory factor to the occurrence of fluorescence. Therefore, it was considered that a method for detecting nucleic acids according to an embodiment of the present disclosure is preferably performed in an environment in which for example, a microchip is restricted from being in contact with air.

Example 5

Example 5 confirmed that fluorescence is emitted even by using 2-base length oligo-DNA under the same experimental conditions as in Example 1.

<Material and Method>

A fluorometry experiment was performed for seven types of oligo-DNA purchased from Invitrogen Corporation using the same materials and method as in Example 1. The oligo-DNA sequences used were T(20) (Sequence ID No. 1), T(10) (Sequence ID No. 19), T(6) (Sequence ID No. 10), T(5) (Sequence ID No. 27), T(4) (Sequence ID No. 28), T(3) (Sequence ID No. 12), and T(2) (Sequence ID No. 29). In this experiment, the $CuSO_4$ concentration was 0.4 mM, the S.A. concentration was 4 mM, and NanoDrop 3300 was used for measurement.

<Results>

FIGS. 35A to 35F show the results of measurement of T(20). The oligo-DNA concentration is 100 micromoles (A), 50 micromoles (B), 50 micromoles (C), 25 micromoles (D), 12.5 micromoles (E), or 6.25 micromoles (F). In each of the graphs, the wavelength (nm) is shown in the abscissa, and fluorescence intensity (RFU value) is shown on the ordinate. FIGS. 36A to 41G show the results of measurement of oligo-DNA of T(10), T(6), T(5), T(4), T(3), and T(2). In each of the graphs, a numerical value represents the concentration condition of oligo-DNA.

FIGS. 42 A to 42G show fluorescence spectra measured under the concentration conditions in which oligo-DNA showed the highest fluorescence intensity. The wavelength (nm) is shown on the abscissa, and relative values (1 of peak RFU value) of fluorescence intensity (RFU values) are shown on the ordinate. FIGS. 42A, 42B, 42C, 42D, 42E, 42F, and 42G show fluorescence spectra of T(20), T(10), T(6), T(5), T(4), T(3), and T(2), respectively.

FIGS. 43 A to 43G are each a graph in which the peak RFU values at the respective concentrations of oligo-DNA are plotted. The concentration (micromole) of oligo-DNA is shown on the abscissa, and the peak RFU value (logarithmic value) is shown on the ordinate. FIGS. 43A, 43B, 43C, 43D, 43E, 43F, and 43G show the results of T(20), T(10), T(6), T(5), T(4), T(3), and T(2), respectively.

<Consideration>

The results of this example revealed that even with oligo-DNA having a base sequence containing thymine 2 bases, fluorescence is observed. It was found that although the shape of a fluorescence spectrum is little changed even by changing the concentration of oligo-DNA, the fluorescence peak tends to shift to the short wavelength side as the base length decreases (refer to FIGS. 42A to 42G). In addition, there was observed the tendency that the intensity of a fluorescence spectrum depends on the concentration of oligo-DNA, but the intensity reaches a plateau at a predetermined concentration or more and, conversely, decrease in intensity was observed in some cases (refer to FIGS. 43A to 43G). Further, the phenomenon of decrease in fluorescence intensity at an excessively high DNA concentration was observed in the experiment using the copper powder in Example 2 (Refer to FIGS. 19A and 19B).

Example 6

In Example 6, an experiment was conducted using 3-base length oligo-DNA composed of T and C or T and G under the same experimental conditions as in Example 1.

<Material and Method>

A fluorometry experiment was performed for oligo-DNA purchased from Invitrogen Corporation using the same materials and method as in Example 1. The oligo-DNA sequences used were TTT (Sequence ID No. 12), TTC, TCT, CTT, TCC, CTC, CCT, CCC, TTG, TGT, GTT, TGG, GTG, GGT, and GGG. In this experiment, the $CuSO_4$ concentration was 0.4 mM, the S.A. concentration was 4 mM, the oligo-DNA concentration was 0.5 mM, and NanoDrop 3300 was used for measurement.

<Results>

The results are shown in FIGS. 44A to 45H. FIGS. 44A to 44H show the results of measurement of TTT (Sequence ID No. 12), TTC, TCT, CTT, TCC, CTC, CCT, and CCC, respectively. FIGS. 45A to 45H show the results of measurement of TTT (Sequence ID No. 12), TTG, TGT, GTT, TGG, GTG, GGT, and GGG, respectively. The wavelength (nm) is shown on the abscissa, and the logarithmic value of fluorescence intensity (RFU value) is shown on the ordinate.

With the oligo-DNA having mixed sequences of T and C, highest fluorescence intensity was observed with TTT, CTT, CCT, and TCT were second to TTT, and weak fluorescence was observed with TTC and CTC (refer to FIGS. 44A to 44H). On the other hand, with TCC and CCC, fluorescence with a peak near 600 nm was not observed. In addition, with the oligo-DNA having mixed sequences of T and G, medium fluorescence intensity was observed with TTG, weak fluorescence was observed with GTT, and fluorescence with a peak near 600 nm was not observed with the other sequences (refer to FIGS. 45A to 45H).

<Consideration>

With the oligo-DNA having mixed sequences of T and C, CTT containing T at the second and third positions showed higher fluorescence intensity than TCT and TTC. In addition, TCT and CCT containing T at the third position showed higher fluorescence intensity than TTC and CTC containing T at the second position. It was considered from these results that in the oligo-DNA having mixed sequences of T and C, base T at the third position most contributes to fluorescence, and base T at the second position next contributes to fluorescence.

With the oligo-DNA having mixed sequences of T and G excepting TTG and GTT, fluorescence with a peak near 600 nm was not observed, and as a whole, fluorescence intensity was lower than the oligo-DNA mixed sequences of T and C. It was considered from these results that G has the function of absorbing fluorescence energy and quenching fluorescence.

Example 7

In Example 7, it was confirmed that fluorescence is quenched by a quench dye.

<Material and Method>

A fluorometry experiment was performed for oligo-DNA of T(10) (Sequence ID No. 19) purchased from Invitrogen Corporation and oligo-DNA (T(10)BHQ2) (Sigma Aldrich Inc.) in which the 3' terminal of T(10) was modified with Black Hole Quencher-2 (BHQ2) using the same materials and method as in Example 1. In this experiment, the $CuSO_4$ concentration was 0.4 mM, the S.A. concentration was 4 mM, the oligo-DNA concentration was 0.05 mM, and Nano-Drop 3300 was used for measurement.

<Results>

The results are shown in FIG. 46. In this figure, the wavelength (nm) is shown on the abscissa, and fluorescence intensity (RFU value) is shown on the ordinate. With T(10), fluorescence was clearly observed, but no fluorescence was detected with T(10)BHQ2 modified with the quencher.

<Consideration>

BHQ2 is a quencher that particularly effectively absorbs light at about 560 nm to 650 nm. It was considered that the fluorescence observed with T(10) is not observed with T(10)BHQ2 due to the effect of BHQ2. This result suggested that fluorescence by the action of copper can be combined with FRET (fluorescence resonance energy transfer).

Example 8

In Example 8, as a result of comparison between the fluorescence intensities and spectral shapes of thymine (T) and uracil (U), it was confirmed that both show different intensities but show the same spectral shape. Further, as a result of examination of fluorescence of methylated cytosine (MeC) and inosine (I), it was found that both do not produce fluorescence.

<Material and Method>

A fluorometry experiment was performed for various types of oligo-DNA using the same materials and method as in Example 1. As the oligo-DNA, T(10) (Sequence ID No. 19), U(9)G (Sequence ID No. 20), A(10) (Sequence ID No. 30), and I(9)G (Sequence ID No. 31) purchased from Invitrogen Corporation were used. Also, as the oligo-DNA, C(10) (Sequence ID No. 32) and C(4)MeC(6) (Sequence ID No. 33, MeC is 5-methyl-2-deoxycytidine) purchased from Sigma Aldrich Corporation were used. In this experiment, the $CuSO_4$ concentration was 0.4 mM, the S.A. concentration was 4 mM, the oligo-DNA concentration was 0.05 mM, and NanoDrop 3300 was used for measurement.

<Results>

FIGS. 47A and 47B show the results of three times of measurement using each of T(10) and U(9)G. FIG. 47A is a graph in which the wavelength (nm) is shown on the abscissa, and fluorescence intensity (RFU) is shown on the ordinate, and FIG. 47B is a graph in which a relative value (to 1 of the peak RFU value of each oligo-DNA) of average fluorescence intensity (RFU value) is shown on the ordinate. It was confirmed that the intensity of U(9)G is lower than T(10), but fluorescence with a similar spectral shape is emitted.

FIG. 48 shows the measurement results of T(10), C(10), and C(4)MeC(6). In this figure, the wavelength (nm) is shown on the abscissa, and fluorescence intensity (RFU) is shown on the ordinate. Although significant fluorescence was observed with T(10), no fluorescence was observed with C(10) and C(4)MeC(6).

FIG. 49 shows the measurement results of T(10), A(10), and I(9)G. In this figure, the wavelength (nm) is shown on the abscissa, and fluorescence intensity (RFU) is shown on the ordinate. Although significant fluorescence was observed with T(10) and weak fluorescence was observed with A(10), no fluorescence was observed with I(9)G.

<Consideration>

With a nucleic acid having a sequence composed of uracil, intensity is lower than that with a nucleic acid having a sequence composed of thymine, but both nucleic acids emit fluorescence with similar spectral shapes. This result was confirmed in Example 1. In addition, it was confirmed that a nucleic acid having a sequence composed of cytosine or a sequence composed of cytosine and methylated cytosine does not emit fluorescence.

These results indicated that uracil can be discriminated from cytosine and methylated cytosine by detecting fluorescence using copper. This suggested that a method for detecting nucleic acids according to an embodiment of the present disclosure is capable of analyzing methylation on DNA molecules by detecting bisulfite reaction substitution of cytosine (C) with uracil (U).

The present disclosure contains subject matter related to that disclosed in Japanese Priority Patent Application JP 2012-108719 filed in the Japan Patent Office on May 10, 2012, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

INDUSTRIAL APPLICABILITY

A microchip for nucleic acid analysis according to an embodiment of the present disclosure can be used by a simple operation and can exhibit stable performance even after long-term storage. Therefore, the microchip for nucleic acid analysis according to an embodiment of the present disclosure can be employed for nucleic acid analysis in various fields such as the medical field, the drug discovery field, the clinical examination field, the food field, the agricultural field, the engineering field, the medicolegal field, and the criminal identification field.

It is to be noted that the embodiments may have the following configurations.

(1) A microchip including:
a reaction region; and
a detection region connected to the reaction region by a flow passage, the detection region including copper.

(2) The microchip according to (1), wherein the copper is solid copper, a solid containing copper, or a copper-containing alloy.

(3) The microchip according to (1), wherein the copper is in the form of a solution containing copper.

(4) The microchip according to (1), further including an inlet portion fluidly connected to the reaction region.

(5) The microchip according to (1), wherein the detection region further includes a salt.

(6) The microchip according to (5), wherein the salt is selected from the group consisting of NaCl, KCl and MgCl2.

(7) The microchip according to (5), wherein the salt is disposed as a solution having a concentration of at least 10 mM.

(8) The microchip according to (1), wherein a form of the copper is selected from the group consisting of a powder, fine particles, a rod, a wire, a plate and a foil.

(9) The microchip according to (1), wherein the copper is configured and disposed in the detection region to not prevent an emission of fluorescence upon a reaction of a nucleic acid with the copper.

(10) The microchip according to (1), further including: an inlet;
electrophoretic channels as the reaction region; and
electrodes provided at ends of each of the electrophoretic channels,
wherein at least two of the electrophoretic channels cross at a joint portion.

(11) The microchip according to (10), further including first and second openings that are connected to the detection region, and are configured to enable a flow of a buffer solution through the detection region via the flow passage.

(12) The microchip according to (11), further including a second flow passage including a third opening at one of the ends of said second flow passage, the second flow passage being connected to a position between the detection region and the joint portion in the flow passage.

(13) The microchip according to (12), wherein the third opening and the second flow passage are configured to enable a flow of a salt solution to the detection region.

(14) The microchip according to (11), further including a second flow passage including a salt solution tank at one of the ends of said second flow passage, the second flow passage being connected to a position between the detection region and the joint portion in the flow passage.

(15) The microchip according to (14), wherein the salt solution tank and the second flow passage are configured to enable a flow of a salt solution to the detection region.

(16) The microchip according to (15), further including a waste liquid tank connected to an output of the detection region.

(17) A method of detecting a nucleic acid with a microchip, the method including: moving a reacted nucleic acid from a reaction region of the microchip to a detection region of the microchip; and detecting fluorescence of the reacted nucleic acid after contacting the reacted nucleic acid with copper contained in the detection region.

(18) The method according to (17), further including:
introducing a nucleic acid through an inlet of the microchip;
moving the nucleic acid through a first flow passage to the reaction region; and
performing a nucleic acid reaction on the nucleic acid to form the reacted nucleic acid.

(19) The method according to (18), wherein the nucleic acid reaction is selected from the group consisting of a nucleic acid amplification reaction, electrophoresis, a hybridization reaction, and a bisulfite reaction.

(20) The method according to (17), wherein detecting fluorescence of the reacted nucleic acid includes
mixing a sample solution including the reacted nucleic acid with a salt solution in the detection region,
forming a nucleic acid-copper complex, and
irradiating the nucleic acid-copper complex with excitation light to cause the nucleic acid-copper compound to fluoresce.

(21) A method of manufacturing a microchip, the method including:
providing a reaction region; and
providing a detection region that is connected to the reaction region by a flow passage, the detection region including copper.

(22) The method of manufacturing a microchip according to (21), further including bonding together substrate layers in which an inlet, the reaction region, the detection region, and the flow passage are formed.

(23) The method of manufacturing a microchip according to (22), further including forming the inlet, the reaction region, the detection region and the flow passages by wet etching or dry etching of a silicon or glass substrate layer, nano-imprinting, injection molding, or cutting of a plastic substrate layer.

(24) The method of manufacturing a microchip according to (21), wherein the copper is solid copper, a solid containing copper, or a copper-containing alloy.

(25) The method of manufacturing a microchip according to (21), wherein the copper is in the form of a solution containing copper.

(26) The method of manufacturing a microchip according to (21), wherein a form of the copper is selected from the group consisting of a powder, fine particles, a rod, a wire, a plate and a foil.

(27) The method of manufacturing a microchip according to (21), further including forming an inlet portion that is fluidly connected to the reaction region.

(28) The method of manufacturing a microchip according to (21), wherein the copper is configured and disposed in the detection region to not prevent an emission of fluorescence upon a reaction of a nucleic acid with the copper.

(29) The method of manufacturing a microchip according to (21), further including:
forming an inlet;
forming electrophoretic channels as the reaction region; and
forming electrodes that are provided at ends of each of the electrophoretic channels, wherein at least two of the electrophoretic channels cross at a joint portion.

(30) The method of manufacturing a microchip according to (29), further including forming first and second openings that are connected to the detection region, and are configured to enable a flow of a buffer solution through the detection region via the flow passage.

(31) The method of manufacturing a microchip according to (30), further including forming a second flow passage including a third opening at one of the ends of said second flow passage, the second flow passage being connected to a position between the detection region and the joint portion in the flow passage.

(32) The method of manufacturing a microchip according to (31), wherein the third opening and the second flow passage are configured to enable a flow of a salt solution to the detection region.

(33) The method of manufacturing a microchip according to (32), further including forming a second flow passage including a salt solution tank at one of the ends of said second flow passage, the second flow passage being connected to a position between the detection region and the joint portion in the flow passage.

(34) The method of manufacturing a microchip according to (33), wherein the salt solution tank and the second flow passage are configured to enable a flow of a salt solution to the detection region.

(35) The method of manufacturing a microchip according to (34), further including providing a waste liquid tank that is connected to an output of the detection region.

It is to be noted that the embodiments may also have the following configurations.

(1) A microchip for nucleic acid analysis, the microchip including:
a reaction region; and
a detection region,
wherein the detection region contains copper.

(2) The microchip for nucleic acid analysis according to (1), wherein the copper is solid copper.

(3) The microchip for nucleic acid analysis according to (2), wherein the detection region contains a salt.

(4) The microchip for nucleic acid analysis according to (3), wherein the amount of the salt contained is determined so that a final concentration after a sample solution containing a nucleic acid is introduced into the detection region is 50 mM or more.

(5) The microchip for nucleic acid analysis according to (4), wherein the solid copper is sputtered, deposited, or applied to the detection region.

(6) The microchip for nucleic acid analysis according to (5), wherein the salt is sodium chloride or potassium chloride.

(7) The microchip for nucleic acid analysis according to (6), wherein the reaction region serves as a reaction field of amplification reaction, electrophoresis, hybridization reaction, or bisulfite reaction of the nucleic acid.

(8) The microchip for nucleic acid analysis according to (7), further including: an inlet through which the sample solution is introduced into the reaction region; and a flow passage that connects the reaction region to the detection region.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST 1a, 1b, 1c, 1d: microchip for nucleic acid analysis, 2: inlet, 3: reaction region, 31, 32: electrophoretic channel, 311, 312, 321, 322: electrode, 33, 34: joint portion, 4: detection region, 51, 52: flow passage, 6: copper, 7: salt

The invention claimed is:

1. A microchip comprising:

a reaction region; and a detection region connected to the reaction region by a flow passage, the detection region including a thin film of copper having light transparency, wherein the copper is solid copper, a solid containing copper, or a copper-containing alloy, and wherein the detection region further includes a salt.

2. The microchip according to claim 1, wherein the salt is selected from the group consisting of NaCl, KCl and MgCl$_2$.

3. The microchip according to claim 1, wherein the salt is disposed as a solution having a concentration of at least 10 mM.

4. The microchip according to claim 1, wherein the thin film of copper is disposed on only one inside surface of the detection region and does not extend to any edge of the detection region on the one inside surface, and has a thickness ranging from 10 to 50 nm on the one inside surface of the detection region.

5. The microchip according to claim 1, further comprising an inlet portion fluidly connected to the reaction region.

6. A microchip comprising:

a reaction region;

a detection region connected to the reaction region by a flow passage, the detection region including a thin film of copper having light transparency, wherein the copper is solid copper, a solid containing copper, or a copper-containing alloy;

an inlet;

electrophoretic channels as the reaction region; and electrodes provided at ends of each of the electrophoretic channels, wherein at least two of the electrophoretic channels cross at a joint portion.

7. The microchip according to claim 6, further comprising first and second openings that are connected to the detection region, and are configured to enable a flow of a buffer solution through the detection region via the flow passage.

8. The microchip according to claim 7, further comprising a second flow passage including a third opening at one of the ends of said second flow passage, the second flow passage being connected to a position between the detection region and the joint portion in the flow passage.

9. The microchip according to claim 7, further comprising a second flow passage including a salt solution tank at one of the ends of said second flow passage, the second flow passage being connected to a position between the detection region and the joint portion in the flow passage.

10. The microchip according to claim 1, wherein the copper is formed on the detection region by sputtering, vapor deposition, or coating.

11. The microchip according to claim 6, wherein the copper is formed on the detection region by sputtering, vapor deposition, or coating.

12. The microchip according to claim 6, wherein the thin film of copper is disposed on only one inside surface of the detection region and does not extend to any edge of the detection region on the one inside surface, and has a thickness ranging from 10 to 50 nm on the one inside surface of the detection region.

* * * * *